(12) United States Patent
Mazumdar et al.

(10) Patent No.: US 7,799,554 B2
(45) Date of Patent: Sep. 21, 2010

(54) LATERAL FLOW DEVICES

(75) Inventors: Debapriya Mazumdar, Urbana, IL (US); Juewen Liu, Urbana, IL (US); Yi Lu, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 432 days.

(21) Appl. No.: 11/686,601

(22) Filed: Mar. 15, 2007

(65) Prior Publication Data

US 2007/0269821 A1 Nov. 22, 2007

Related U.S. Application Data

(60) Provisional application No. 60/782,949, filed on Mar. 16, 2006, provisional application No. 60/821,043, filed on Aug. 1, 2006.

(51) Int. Cl.
*C12M 1/00* (2006.01)
*C07H 21/02* (2006.01)

(52) U.S. Cl. .................. 435/283.1; 536/23.1

(58) Field of Classification Search .............. None
See application file for complete search history.

(56) References Cited

U.S. PATENT DOCUMENTS

| | | | |
|---|---|---|---|
| 4,362,603 A | 12/1982 | Presson et al. | |
| 4,703,017 A | 10/1987 | Campbell et al. | |
| 4,746,631 A * | 5/1988 | Clagett | 436/518 |
| 4,855,240 A | 8/1989 | Rosenstein et al. | |
| 4,857,319 A | 8/1989 | Crowe et al. | |
| 5,008,109 A | 4/1991 | Tin | |
| 5,459,040 A | 10/1995 | Hammock et al. | |
| 5,472,881 A | 12/1995 | Beebe et al. | |
| 5,580,967 A | 12/1996 | Joyce | |
| 5,593,835 A | 1/1997 | Rando et al. | |
| 5,631,148 A | 5/1997 | Urdea | |
| 5,663,064 A | 9/1997 | Burke et al. | |
| 5,807,718 A | 9/1998 | Joyce et al. | |
| 5,807,967 A | 9/1998 | Snow et al. | |
| 5,910,408 A | 6/1999 | Szostak et al. | |

(Continued)

FOREIGN PATENT DOCUMENTS

EP          121970          10/1984

(Continued)

OTHER PUBLICATIONS

Abstract of Joyce, G., "Design and catalytic activity of enzyumic DNA molecules"., (1998).

(Continued)

*Primary Examiner*—Samuel Woolwine
(74) *Attorney, Agent, or Firm*—Evan Law Group LLC

(57) ABSTRACT

An analytical test for an analyte comprises (a) a base, having a reaction area and a visualization area, (b) a capture species, on the base in the visualization area, comprising nucleic acid, and (c) analysis chemistry reagents, on the base in the reaction area. The analysis chemistry reagents comprise (i) a substrate comprising nucleic acid and a first label, and (ii) a reactor comprising nucleic acid. The analysis chemistry reagents can react with a sample comprising the analyte and water, to produce a visualization species comprising nucleic acid and the first label, and the capture species can bind the visualization species.

11 Claims, 14 Drawing Sheets

U.S. PATENT DOCUMENTS

| | | | |
|---|---|---|---|
| 5,989,813 | A | 11/1999 | Gerdes |
| 6,040,138 | A | 3/2000 | Lockhart et al. |
| 6,110,462 | A | 8/2000 | Barbas et al. |
| 6,159,347 | A | 12/2000 | Sumner, Jr. et al. |
| 6,287,765 | B1 | 9/2001 | Cubicciotti |
| 6,316,194 | B1 | 11/2001 | Karn et al. |
| 6,326,508 | B1 | 12/2001 | Godbole et al. |
| 6,361,944 | B1 | 3/2002 | Mirkin et al. |
| 6,387,617 | B1 | 5/2002 | Asher et al. |
| 6,426,335 | B1 | 7/2002 | Janjic et al. |
| 6,451,535 | B1 | 9/2002 | Jenne et al. |
| 6,485,982 | B1 | 11/2002 | Charlton |
| 6,541,617 | B1 | 4/2003 | Bamdad et al. |
| 6,630,306 | B1 | 10/2003 | Breaker |
| 6,706,474 | B1 | 3/2004 | Lu et al. |
| 6,818,455 | B2 | 11/2004 | May et al. |
| 6,843,890 | B1 | 1/2005 | Godbole |
| 6,849,414 | B2 | 2/2005 | Guan et al. |
| 6,890,719 | B2 | 5/2005 | Lu et al. |
| 7,109,165 | B2 | 9/2006 | Matulic-Adamic et al. |
| 7,192,708 | B2 | 3/2007 | Lu et al. |
| 7,332,283 | B2 | 2/2008 | Lu et al. |
| 7,612,185 | B2 | 11/2009 | Lu et al. |
| 2003/0215810 | A1 | 11/2003 | Lu et al. |
| 2003/0235611 | A1 | 12/2003 | Ehringer et al. |
| 2004/0018515 | A1 | 1/2004 | Diener et al. |
| 2004/0110167 | A1* | 6/2004 | Gerdes et al. ............ 435/6 |
| 2004/0126882 | A1 | 7/2004 | Ellington et al. |
| 2004/0175693 | A1 | 9/2004 | Lu et al. |
| 2005/0037075 | A1 | 2/2005 | Farokhzad et al. |
| 2005/0136500 | A1 | 6/2005 | Yang et al. |
| 2005/0282186 | A1 | 12/2005 | Lu et al. |
| 2006/0019406 | A1 | 1/2006 | Wei et al. |
| 2006/0040408 | A1* | 2/2006 | Jones et al. ............ 436/518 |
| 2006/0045910 | A1 | 3/2006 | Ehringer |
| 2006/0094026 | A1 | 5/2006 | Lu et al. |
| 2006/0166222 | A1 | 7/2006 | Lu et al. |
| 2007/0037171 | A1 | 2/2007 | Lu et al. |
| 2007/0269821 | A1 | 11/2007 | Mazumdar et al. |
| 2008/0176228 | A1 | 7/2008 | Lu et al. |
| 2009/0011402 | A1 | 1/2009 | Lu et al. |
| 2009/0029874 | A1 | 1/2009 | Lu et al. |
| 2009/0197261 | A1 | 8/2009 | Lu et al. |
| 2010/0105039 | A1 | 4/2010 | Lu et al. |
| 2010/0151579 | A1 | 6/2010 | Wang et al. |
| 2010/0166842 | A1 | 7/2010 | Lu et al. |

FOREIGN PATENT DOCUMENTS

| | | |
|---|---|---|
| EP | 1219708 | 7/2002 |
| EP | 1 312 674 | 5/2003 |
| GB | 2339280 | 1/2000 |
| WO | WO 91/14696 | 10/1991 |
| WO | WO 96/17086 | 6/1996 |
| WO | WO 97/09342 | 3/1997 |
| WO | WO 98/04740 | 2/1998 |
| WO | WO 98/27104 | 6/1998 |
| WO | WO 98/39484 | 9/1998 |
| WO | WO 98/49346 | 11/1998 |
| WO | WO 99/13338 | 3/1999 |
| WO | WO 99/27351 | 6/1999 |
| WO | WO 99/47704 | 9/1999 |
| WO | WO 00/26226 | 5/2000 |
| WO | WO 00/58505 | 10/2000 |
| WO | WO 01/00876 | 1/2001 |
| WO | WO 01/23548 | 4/2001 |
| WO | WO 01/24696 | 4/2001 |
| WO | WO 01/27612 A2 | 4/2001 |
| WO | WO 01/27612 A3 | 4/2001 |
| WO | WO 01/51665 | 7/2001 |
| WO | WO 01/73123 | 10/2001 |
| WO | WO 02/00006 | 1/2002 |
| WO | WO 02/22882 | 3/2002 |
| WO | WO 02/098364 | 12/2002 |
| WO | WO 03/062422 | 7/2003 |
| WO | WO 03/068963 | 8/2003 |
| WO | WO 03/094838 | 11/2003 |
| WO | WO 03/095648 | 11/2003 |
| WO | WO 2004/046687 | 6/2004 |
| WO | 2004/081235 | 9/2004 |
| WO | WO 2005/082922 | 9/2005 |
| WO | WO 2005/095967 | 10/2005 |
| WO | WO 2005/100602 | 10/2005 |
| WO | WO 2006/020768 | 2/2006 |
| WO | WO 2006/048164 | 5/2006 |
| WO | WO 2006/052419 | 5/2006 |
| WO | WO 2006/078660 | 7/2006 |
| WO | WO 2007/106118 | 9/2007 |
| WO | WO 2007/109500 | 9/2007 |
| WO | WO 2008/089248 | 7/2008 |
| WO | WO 2009/012309 | 1/2009 |
| WO | WO 2009/045632 | 4/2009 |

OTHER PUBLICATIONS

Aggarwal, S.K., et al., "Determination of lead in urine and whole blood by stable isotope dilution gas chromatography-mass spectrometry"., Clinical Chemistry, vol. 40, No. 8, pp. 1494-1502, (1994).

Alivisatos, A.P., et al., "Organization of "nanocrystal molecules" using DNA"., Nature, vol. 382, pp. 609-611, (1996).

Allara, D. et al., "Spontaneously organized molecular assemblies. 1.Formation, dynamics and physical properties of n-alkanoic acids adsorbed from solution on an oxidized aluminum surface"., Langmuir, vol. 1, No. 1, pp. 45-52, (1985).

Andreola, M-L., et al., "DNA aptamers selected against the HIV-1 RNase H display in vitro antiviral activity"., Biochemistry, vol. 40, No. 34, pp. 10087-10094, (2001).

Bain, C. D., et al., "Modeling organic surfaces with self-assembled monolayers"., Angew. Chem. Int. Ed. Engl., vol. 28, No. 4, pp. 506-512, (1989).

Bannon, D.I., et al., "Graphite furnace atomic absorption spectroscopic measurement of blood lead in matrix-matched standards"., Clinical Chemistry, vol. 40, No. 9, pp. 1730-1734, (1994).

Been, M.D., et al., "Self-cleaving ribozymes of hepatitis delta virus RNA"., Eur. J. Biochem., vol. 247, pp. 741-753, (1997).

Berens, C., et al., "A tetracycline-binding RNA aptamer"., Bioorganic & Medicinal Chemistry, vol. 9, pp. 2549-2556, (2001).

Biroccio, A., et al., "Selection of RNA aptamers that are specific and high-affinity ligands of the hepatitis C virus RNA-dependent RNA polymerase"., Journal of Virology, vol. 76, No. 8, pp. 3688-3696, (2002).

Blake, D.A., et al., "Antibody-based sensors for heavy metal ions"., Biosensors & Bioelectronics, vol. 16, pp. 799-809, (2001).

Blank, M., et al., "Systematic evolution of a DNA aptamer binding to rat brain tumor microvessels. Selective targeting of endothelial regulatory protein pigpen"., Journal of Biological Chemistry, vol. 276, No. 19, pp. 16464-16468, (2001).

Bock, L.C., et al., "Selection of single-stranded DNA molecules that bind and inhibit human thrombin"., Nature, vol. 355, pp. 564-566, (1992).

Bogden, J.D., et al., "Soil contamination from lead in paint chips"., Bulletin of Environmental Contamination & Toxicology, vol. 14, No. 3, pp. 289-294, (1975).

Boiziau, C., et al., "DNA aptamers selected against the HIV-1 trans-activation-responsive RNA element form RNA-DNA kissing complexes"., Journal of Biological Chemistry, vol. 274, No. 18, pp. 12730-12737, (1999).

Bowins, R.J., et al., "Electrothermal isotope dilution inductively coupled plasma mass spectrometry method for the determination of sub-ng ml$^{-1}$ levels of lead in human plasma"., Journal of Analytical Atomic Spectrometry, vol. 9, pp. 1233-1236, (1994).

Breaker, R.R., "Catalytic DNA: in training and seeking employment"., Nature Biotechnology, vol. 17, pp. 422-423, (1999).

Breaker, R.R., "DNA aptamers and DNA enzymes" Current Opinion in Chemical Biology, vol. 1, pp. 26-31, (1997).
Breaker, R.R., "DNA enzymes"., Nature Biotechnology, vol. 15, pp. 427-431, (1997).
Breaker, R.R., "Molecular Biology: Making Catalytic DNAs"., Science, vol. 290, issue 5499, pp. 2095-2096, (2000).
Breaker, R.R., et al., "A DNA enzyme that cleaves RNA"., Chemistry & Biology, vol. 1, No. 4, pp. 223-229, (1994).
Breaker, R.R., et al., "A DNA enzyme with $Mg^{2+}$-dependent RNA phosphoesterase activity"., Chemistry & Biology, vol. 2, No. 10, pp. 655-660, (1995).
Breaker, R.R., et al., "Engineered allosteric ribozymes as biosensor components"., Current Opinion in Biotechnology, vol. 13, pp. 31-39, (2002).
Brody, E.N., et al., "Aptamers as therapeutic and diagnostic agents"., Reviews in Molecular Biotechnology, vol. 74, pp. 5-13, (2000).
Broude, N.E., "Stem-loop oligonucleotides: a robust tool for molecular biology and biotechnology", Trends in Biotechnology, vol. 20, No. 6, pp. 249-256, (2002).
Brown, A.K., et al., "A lead-dependent DNAzyme with a two-step mechanism"., Biochemistry, vol. 42, No. 23, pp. 7152-7161, (2003).
Bruesehoff, P.J., et al., "Improving metal ion specificity during in Vitro selection of catalytic DNA"., Combinatorial Chemistry & High Throughput Screening, vol. 5, pp. 327-335, (2002).
Bruno, J.G., et al., "In vitro selection of DNA aptamers to anthrax spores with electrochemiluminescence detection"., Biosensors & Bioelectronics, vol. 14, pp. 457-464, (1999).
Bruno, J.G., et al., "Use of magnetic beads in selection and detection of biotoxin aptamers by electrochemiluminescence and enzymatic methods"., BioTechniques, vol. 32, No. 1, pp. 178-180, pp. 182-183, (2002).
Brust, M., et al., "Novel gold-dithiol nano-networks with non-metallic electronic properties"., Advanced Materials, vol. 7, No. 9, pp. 795-797, (1995).
Burdette, S.C., et al., "Fluorescent Sensors for $Zn^{2+}$ Based on a Fluorescein Platform: Synthesis, Properties and Intracellular Distribution"., J. Am. Chem. Soc., vol. 123, No. 32, pp. 7831-7841, (2001).
Burgstaller, P., et al., "Isolation of RNA aptamers for biological cofactors by in vitro selection"., Angew. Chem. Int. Ed. Engl, vol. 33, No. 10, pp. 1084-1087, (1994).
Burgstaller, P., et al., "Structural probing and damage selection of citrulline- and arginine-specific RNA aptamers identify base positions required for binding"., Nucleic Acids Research, vol. 23, No. 23, pp. 4769-4776, (1995).
Burke, D.H., et al., "A Novel Acidophilic RNA Motif That Recognizes Coenzyme A"., Biochemistry, vol. 37, No. 13, pp. 4653-4663, (1998).
Burke, D.H., et al., "RNA aptamers to the adenosine moiety of S-adenosyl methionine: structural inferences from variations on a theme and the reproducibility of SELEX"., Nucleic Acids Research, vol. 25, No. 10, pp. 2020-2024, (1997).
Burke, D.H., et al., "RNA aptamers to the peptidyl transferase inhibitor chloramphenicol"., Chemistry & Biology, vol. 4, No. 11, pp. 833-843, (1997).
Burmeister, J., et al., "Cofactor-assisted self-cleavage in DNA libraries with a 3'- 5'-phosphoramidate bond"., Angew. Chem. Int. Ed. Engl., vol. 36, No. 12, pp. 1321-1324, (1997).
Burwell Jr., R.L., "Modified silica gels as adsorbents and catalysts"., Chemical Technology, 4, pp. 370-377, (1974).
Cadwell, R.C., et al., "Mutagenic PCR"., PCR Methods and Applications, vol. 3, pp. S136-S140, (1994).
Cadwell, R.C., et al., "Randomization of genes by PCR mutagenesis"., PCR Methods and Applications, vol. 2, pp. 28-33, (1992).
Cake, K.M., et al., "In vivo x-ray fluorescence of bone lead in the study of human lead metabolism: serum lead, whole blood lead, bone lead, and cumulative exposure"., Advances in X-Ray Analysis, vol. 38, pp. 601-606, (1995).
Camara Rica, C., et al., "Determination of trace concentrations of lead and nickel in human milk by electrothermal atomisation atomic absorption spectrophotometry and inductively coupled plasma emission spectroscopy"., The Science of the Total Environment, vol. 22, pp. 193-201, (1982).

Cao, Y.W., et al., "DNA-modified core-shell Ag/Au nanoparticles"., J. Am. Chem. Soc., vol. 123, No. 32, pp. 7961-7962, (2001).
Carmi, N., et al., "Cleaving DNA with DNA"., Proc. Natl. Acad. Sci. USA, vol. 95, pp. 2233-2237, (1998).
Carmi, N., et al., "In vitro selection of self-cleaving DNAs"., Chemistry & Biology, vol. 3, No. 12, pp. 1039-1046, (1996).
Cech, T.R., "Structure and mechanism of the large catalytic RNAs: group I and group II introns and ribonuclease P"., The RNA World, pp. 239-269, Cold Spring Harbor Laboratory Press, Cold Spring Harbor, New York, (1993).
Cech, T.R., et al., "Group I ribozymes: substrate recognition, catalytic strategies, and comparative mechanistic analysis"., Nucleic Acids and Molecular Biology, vol. 10, pp. 1-17, (1996).
Chaloin, L., et al., "Endogenous expression of a high-affinity pseudoknot RNA aptamer suppresses replication of HIV-1"., Nucleic Acids Research, vol. 30, No. 18, pp. 4001-4008, (2002).
Chapman, K.B., et al., "In vitro selection of catalytic RNAs"., Current Opinion in Structural Biology, vol. 4, pp. 618-622, (1994).
Chartrand, P., et al., "Effect of structural modifications on the activity of the leadzyme"., Biochemistry, vol. 36, No. 11, pp. 3145-3150, (1997).
Chen, J., et al., "Synthesis from DNA of a molecule with the connectivity of a cube"., Nature, vol. 350, pp. 631-633, (1991).
Chen, C-T., et al., "A highly selective fluorescent chemosensor for lead ions"., J. Am. Chem. Soc., vol. 124, pp. 6246-6247, (2002).
Chen, J-H., et al., "A specific quadrilateral synthesized from DNA branched junctions"., J. Am. Chem. Soc., vol. 111, No. 16, pp. 6402-6407, (1989).
Chen, L., et al., "Crystal structure of a four-stranded intercalated DNA: $d(C_4)$"., Biochemistry, vol. 33, No. 46, pp. 13540-13546, (1994).
Chinnapen, D.J.F., et al., "Hemin-stimulated docking of cytochrome c to a hemin—DNA aptamer complex"., Biochemistry, vol. 41, No. 16, pp. 5202-5212, (2002).
Ciesiolka, J., et al., "Selection of an RNA domain that binds $Zn^{2+}$"., RNA, vol. 1, pp. 538-550, (1995).
Ciesiolka, J., et al., "Small RNA-divalent domains"., RNA, vol. 2, pp. 785-793, (1996).
Conaty, J., et al., "Selected classes of minimised hammerhead ribozyme have very high cleavage rates at low $Mg^{2+}$ concentration"., Nucleic Acids Research, vol. 27, No. 11, pp. 2400-2407, (1999).
Conn, M.M., et al., "Porphyrin Metalation Catalyzed by a Small RNA Molecule"., J. Am. Chem. Soc, vol. 118, No. 29, pp. 7012-7013, (1996).
Connell, G.J., et al., "RNAs with dual specificity and dual RNAs with similar specificity"., Science, New Series, vol. 264, issue 5162, pp. 1137-1141, (1994).
Connell, G.J., et al., "Three small ribooligonucleotides with specific arginine sites"., Biochemistry, vol. 32, No. 21, pp. 5497-5502, (1993).
Cuenoud, B., et al., "A DNA metalloenzyme with DNA ligase activity"., Nature, vol. 375, pp. 611-614, (1995).
Czarnik, A.W., "Desperately seeking sensors"., Chemistry & Biology, vol. 2, No. 7, pp. 423-428, (1995).
Dai, X., et al., "Cleavage of an amide bond by a ribozyme"., Science, New Series, vol. 267, issue 5195, pp. 237-240, (1995).
Davis, J.H., et al., "Isolation of high-affinity GTP aptamers from partially structured RNA libraries"., Proc. Natl. Acad. Sci. USA, vol. 99, No. 18, pp. 11616-11621, (2002).
Davis, K.A., et al., "Staining of cell surface human CD4 with 2'-F-pyrimidine-containing RNA aptamers for flow cytometry"., Nucleic Acids Research, vol. 26, No. 17, pp. 3915-3924, (1998).
Definition of the word "ion" printed from Merriam-Webster online dictionary (www.m-w.com) on Jun. 30, 2004.
Definition of the word "particle" printed from Merriam-Webster online dictionary (www.m-w.com) on Jun. 29, 2004.
Deo, S., et al., "A Selective, Ratiometric Fluorescent Sensor for $Pb^{2+}$"., J. Am. Chem. Soc., vol. 122, No. 1, pp. 174-175, (2000).
Derose, V.J., "Two Decades of RNA Catalysis"., Chemistry & Biology, vol. 9, pp. 961-969, (2002).

Didenko, V.V., "DNA probes using fluorescence resonance energy transfer (FRET): Designs and applications"., BioTechniques, vol. 31, pp. 1106-1121, (2001). We have reference, but we are missing pp. 1119-1121.

Doudna, J.A., et al., "The Chemical Repertoire of Natural Ribozymes"., Nature, vol. 418, pp. 222-228, (2002).

Dubois, L.H., et al., "Synthesis, structure, and properties of model organic surfaces"., Annu. Rev. Phys. Chem., vol. 43, pp. 437-463, (1992).

Earnshaw, D.J., et al., "Modified oligoribonucleotides as site-specific probes of RNA structure and function"., Biopolymers (Nucleic Acid Sciences), vol. 48, pp. 39-55, (1998).

Ekland, E.H., et al., "RNA-catalysed RNA polymerization using nucleoside triphosphates"., Nature, vol. 382, pp. 373-376, (1996).

Ekland, E.H., et al., "Structurally complex and highly active RNA ligases derived from random RNA sequences"., Science, vol. 269, issue 5222, pp. 364-370, (1995).

Elghanian, R., et al., "Selective colorimetric detection of polynucleotides based on the distance-dependent optical properties of gold nanoparticles"., Science, vol. 277, pp. 1078-1081, (1997).

Ellington, A.D., et al., "Aptamers as potential nucleic acid pharmaceuticals"., Biotechnology Annual Review, vol. 1, pp. 185-214, (1995).

Ellington, A.D., et al., "In vitro selection of RNA molecules that bind specific ligands"., Nature, vol. 346, pp. 818-822, (1990).

Ellington, A.D., et al., "Selection in vitro of single-stranded DNA molecules that fold into specific ligand-binding structures"., Nature, vol. 355, pp. 850-852, (1992).

Famulok, M., "Molecular Recognition of Amino Acids by RNA-Aptamers: An L-Citrulline Binding RNA Motif and Its Evolution into an L-Arginine Binder"., J. Am. Chem. Soc., vol. 116, No. 5, pp. 1698-1706, (1994).

Famulok, M., "Oligonucleotide aptamers that recognize small molecules", Current Opinion in Structural Biology, vol. 9, pp. 324-329, (1999).

Famulok, M., et al., "In Vitro Selection Analysis of Neomycin Binding RNAs with a Mutagenized Pool of Variants of the 16S rRNA Decoding Region"., Biochemistry, vol. 35, No. 14, pp. 4265-4270, (1996).

Famulok, M., et al., "Stereospecific recognition of tryptophan agarose by in vitro selected RNA"., J. Am. Chem. Soc., vol. 114, No. 10, pp. 3990-3991, (1992).

Faulhammer, D., et al., "Characterization and Divalent Metal-ion Dependence of in Vitro Selected Deoxyribozymes which Cleave DNA/RNA Chimeric Oligonucleotides"., J. Mol. Biol., vol. 269, pp. 188-202, (1997).

Faulhammer, D., et al., "The $Ca^{2+}$ ion as a cofactor for a novel RNA-cleaving deoxyribozyme"., Angew. Chem., Int. Ed. Engl., vol. 35, No. 23/24, pp. 2837-2841, (1996).

Feldman, B.J., et al., "Determination of lead in blood by square wave anodic stripping voltammetry at a carbon disk ultramicroelectrode"., Analytical Chemistry, vol. 66, No. 13, pp. 1983-1987, (1994).

Ferguson, A., et al., "A novel strategy for selection of allosteric ribozymes yields riboreporter™ sensors for caffeine and aspartame"., Nucleic Acids Research, vol. 32, No. 5, pp. 1756-1766, (2004).

Fodor, S.P.A., et al., "Light-directed, spatially addressable parallel chemical synthesis"., Science, New Series, vol. 251, issue 4995, pp. 767-773, (1991).

Frank, D.N., et al., "In vitro selection for altered divalent metal specificity in the RNase P RNA"., Proc. Natl. Acad. Sci. USA, vol. 94, pp. 14355-14360, (1997).

Frens, G., et al., "Controlled Nucleation for the regulation of the particle size in monodisperse gold suspensions"., Nature Physical Science, vol. 241, pp. 20-22, (1973).

Fukusaki, E-I., et al., "DNA aptamers that bind to chitin"., Bioorganic & Medicinal Chemistry letters, vol. 10, pp. 423-425, (2000).

Geiger, A., et al., "RNA aptamers that bind L-arginine with submicromolar dissociation constants and high enantioselectivity"., Nucleic Acids Research, vol. 24, No. 6, pp. 1029-1036, (1996).

Geyer, C.R., et al., "Evidence for the metal-cofactor independence of an RNA phosphodiester-cleaving DNA enzyme"., Chemistry & Biology, vol. 4, No. 8, pp. 579-593, (1997).

Geyer, C.R., et al., "Lanthanide Probes for a Phosphodiester-cleaving, Lead-dependent, DNAzyme", J. Mol. Biol., vol. 275, pp. 483-489, (1998).

Giver, L., et al., "Selection and design of high-affinity RNA ligands for HIV-1 Rev"., Gene, vol. 137, pp. 19-24, (1993).

Giver, L., et al., "Selective optimization of the Rev-binding element of HIV-1".,Nucleic Acids Research, vol. 21, No. 23, pp. 5509-5516, (1993).

Godwin, H.A., et al., "A Flourescent Zinc Probe Based on Metal-Induced Peptide Folding"., J. Am. Chem. Soc., vol. 118, pp. 6514-6515, (1996).

Grabar, K., et al., "Preparation and characterization of Au colloid Monolayers"., Analytical chemistry, vol. 67, No. 4, pp. 735-743, (1995).

Granadillo, V.A., et al., "The influence of the blood levels of lead, aluminum and vanadium upon the arterial hypertension"., Clinica Chimica Acta, vol. 233, pp. 47-59, (1995).

Grate, D., et al., "Laser-mediated, site-specific inactivation of RNA transcripts"., Proc. Natl. Acad. Sci. USA, vol. 96, pp. 6131-6136, (1999).

Guschin, D., et al., "Manual manufacturing of oligonucleotide, DNA, and protein microchips"., Analytical Biochemistry, vol. 250, pp. 203-211, (1997).

Haller, A.A., et al., "In vitro selection of a 7-methyl-guanosine binding RNA that inhibits translation of capped mRNA molecules"., Proc. Natl. Acad. Sci. USA, vol. 94, pp. 8521-8526, (1997).

Harada, K., et al., "Identification of two novel arginine binding DNAs"., The EMBO Journal, vol. 14, No. 23, pp. 5798-5811, (1995).

Hartig, J.S., et al., "Reporter ribozymes for real-time analysis of domain-specific interactions in biomolecules: HIV-1 reverse transcriptase and the primer-template complex"., Angew. Chem. Int. Ed., vol. 41, No. 22, pp. 4263-4266, (2002).

He, X-x., et al., "Bioconjugated nanoparticles for DNA protection from cleavage"., J. Am. Chem. Soc., vol. 125, No. 24, pp. 7168-7169, (2003).

Hennrich, G., et al., "Redox switchable fluorescent probe selective for either Hg(II) or Cd(II) and Zn(II)" J. Am. Chem. Soc., vol. 121, No. 21, pp. 5073-5074, (1999).

Hesselberth, J., et al., "In vitro selection of nucleic acids for diagnostic applications"., Reviews in Molecular Biotechnology, vol. 74, pp. 15-25, (2000).

Hesselberth, J.R., et al., "Simultaneous detection of diverse analytes with an aptazyme ligase array", Analytical Biochemistry vol. 312, pp. 106-112, (2003).

Ho, H-A., et al., "Optical sensors based on hybrid aptamer/conjugated polymer complexes"., J. Am. Chem. Soc., vol. 126, No. 5, pp. 1384-1387, (2004).

Hock, B., "Antibodies for immunosensors, A review"., Analytica Chimica Acta, vol. 347, pp. 177-186, (1997).

Hofmann, H.P., et al., "$Ni^{2+}$-binding RNA motifs with an asymmetric purine-rich internal loop and a G-A base pair"., RNA, vol. 3, pp. 1289-1300, (1997).

Holeman, L.A., et al., "Isolation and characterization of fluorophore-binding RNA aptamers"., Folding & Design, vol. 3, pp. 423-431, (1998).

Hoogstraten, C.G., et al., "NMR solution structure of the lead-dependent ribozyme: Evidence for dynamics in RNA catalysis"., J. Mol. Biol., vol. 284, pp. 337-350, (1998).

Hoogstraten, C.G., et al., "Structural analysis of metal ion ligation to nucleotides and nucleic acids using pulsed EPR spectroscopy"., J. Am. Chem. Soc., vol. 124, No. 5, pp. 834-842, (2002).

Huizenga, D.E., et al., "A DNA aptamer that binds adenosine and ATP"., Biochemistry, vol. 34, No. 2, pp. 656-665, (1995).

Iler, R.K., "The Chemistry of Silica: Solubility, Polymerization, Colloid and Surface Properties, and Biochemistry, Chapter 6, The surface chemistry of silica"., pp. 622-729, A Wiley-Interscience Publication, New York, (1979).

Illangasekare, M., et al., "Small-molecule-substrate interactions with a self-aminoacylating ribozyme"., J. Mol. Biol., vol. 268, pp. 631-639, (1997).

Imperiali, B., et al., "Peptide platforms for metal ion sensing"., Proc. SPIE-The international society for optical engineering, vol. 3858, pp. 135-143, (1999).

International Search Report dated Jan. 15, 2003 for PCT application No. PCT/US01/20557.

International Search Report dated Aug. 1, 2003 for PCT application No. PCT/US03/08483.

Iqbal, S.S., et al., "A review of molecular recognition technologies for detection of biological threat agents"., Biosensors & Bioelectronics, vol. 15, pp. 549-578, (2000).

Abstract of: Iwasaki, K., Mizota, T., Kenkyu Hokoku—Kanagawa-ken Kogyo Shikensho 1991, 62, 57.

Jagner, D., et al., "Determination of lead in microliter amounts of whole blood by stripping potentiometry"., Electroanalysis, vol. 6, pp. 285-291, (1994).

Jayasena, S.D., "Aptamers: an emerging class of molecules that rival antibodies in diagnostics"., Clinical Chemistry, vol. 45, No. 9, pp. 1628-1650, (1999).

Jenison, R., et al., "Interference-based detection of nucleic acid targets on optically coated silicon", Nature Biotechnology, vol. 19, pp. 62-65, (2001).

Jenison, R.D., et al., "High-resolution molecular discrimination by RNA"., Science, vol. 263, pp. 1425-1429, (1994).

Jenne, A., et al., "Rapid Identification and Characterization of Hammerhead-Ribozyme Inhibitors Using Fluorescence-Based Technology"., Nature Biotechnology, vol. 19, pp. 56-61, (2001).

Jenne, A., et al., "Real-time Characterization of Ribozymes by Fluorescence Resonance Energy Transfer (FRET)"., Angewandte Chemie. International Edition, vol. 38, No. 9, pp. 1300-1303, (1999).

Jhaveri, S., et al., "In vitro selection of signaling aptamers"., Nature Biotechnology, vol. 18, pp. 1293-1297, (2000).

Jhaveri, S.D., et al., "Designed signaling aptamers that transduce molecular recognition to changes in fluorescence intensity"., J. Am. Chem. Soc., vol. 122, No. 11, pp. 2469-2473, (2000).

Jin, R., et al., "What controls the melting properties of DNA-linked gold nanoparticle assemblies?"., J. Am. Chem. Soc., vol. 125, No. 6, pp. 1643-1654, (2003).

Joos, B., et al., "Covalent attachment of hybridizable oligonucleotides to glass supports"., Analytical Biochemistry, vol. 247, pp. 96-101, (1997).

Josephson, L., et al., "Magnetic nanosensors for the detection of oligonucleotide sequences"., Angewandte Chemie. International Edition, vol. 40, No. 17, pp. 3204-3206, (2001).

Joyce, G.F., "Appendix 3: Reactions Catalyzed by RNA and DNA Enzymes". The RNA World, vol. 37, pp. 687-690, Cold Spring Harbor Laboratory Press, Cold Spring Harbor, New York, (1999).

Joyce, G.F., "In vitro evolution of nucleic acids"., Current Opinion in Structural Biology, vol. 4, pp. 331-336, (1994).

Katahira, M., et al., "Two metal-binding sites in a lead ribozyme bound to competitively by $Pb^{2+}$ and $Mg^{2+}$: Induced structural changes as revealed by NMR"., European Journal of Biochemistry, vol. 255, pp. 727-733, (1998).

Kato, T., et al., "In vitro selection of DNA aptamers which bind to cholic acid"., Biochimica et Biophysica Acta, vol. 1493, pp. 12-18, (2000).

Kawakami, J., et al., "In vitro selection of aptamers that act with $Zn^{2+}$"., Journal of Inorganic Biochemistry, vol. 82, pp. 197-206, (2000).

Khan, R., et al., "Interaction of retroviral nucleocapsid proteins with transfer $RNA^{Phe}$: a lead ribozyme and $^1H$ NMR study"., Nucleic Acids Research, vol. 24, No. 18, pp. 3568-3575, (1996).

Khosraviani, M., et al., "Detection of heavy metals by immunoassay: Optimization and validation of a rapid, portable assay for ionic cadmium"., Environ. Sci. Technol., vol. 32, No. 1, pp. 137-142, (1998).

Kiga, D., et al., "An RNA aptamer to the xanthine/guanine base with a distinctive mode of purine recognition"., Nucleic Acids Research, vol. 26, No. 7, pp. 1755-1760, (1998).

Kim, M.H., et al., "Activation and repression of the activity of a lead ribozyme by the combination of $Pb^{2+}$ and $Mg^{2+ 1}$"., J. Biochem., vol. 122, No. 5, pp. 1062-1067, (1997).

Klußmann, S., et al., "Mirror-image RNA that binds D-adenosine"., Nature Biotechnology, vol. 14, pp. 1112-1115, (1996).

Kohama, T., et al., "Molecular Cloning and Functional Characterization of Murine Sphingosine Kinase", The Journal of Biological Chemistry, vol. 273, No. 37, pp. 23722-23728, (1998).

Koizumi, M., et al., "Allosteric selection of ribozymes that respond to the second messengers cGMP and cAMP"., Nature Structural Biology, vol. 6, No. 11, pp. 1062-1071, (1999).

Koizumi, M., et al., "Molecular Recognition of cAMP by an RNA Aptamer"., Biochemistry, vol. 39, No. 30, pp. 8983-8992, (2000).

Koizumi, M., et al., "Allosteric ribozymes sensitive to the second messengers cAMP and cGMP"., Nucleic Acids Symposium Series, No. 42, pp. 275-276, (1999).

Kruger, K., et al., "Self-splicing RNA: autoexcision and autocyclization of the ribosomal RNA intervening sequence of the Tetrahymena"., Cell, vol. 31, pp. 147-157, (1982).

Lato, S.M., et al., "In vitro selection of RNA lectins: Using combinatorial chemistry to interpret ribozyme evolution"., Chemistry & Biology, vol. 2, No. 5, pp. 291-303, (1995).

Lauhon, C.T., et al., "RNA aptamers that bind flavin and nicotinamide redox cofactors"., J. Am. Chem. Soc., vol. 117, No. 4, pp. 1246-1257, (1995).

Lebruska, L.L., "Selection and Characterization of an RNA Decoy for Transcription Factor NF-κB"., Biochemistry, vol. 38, No. 10, pp. 3168-3174, (1999).

Lee, M., et al., "A fiber-optic microarray biosensor using aptamers as receptors"., Analytical Biochemistry, vol. 282, pp. 142-146, (2000).

Lee, S-W., et al., "Ordering of quantum dots using genetically engineered viruses"., Science, vol. 296, pp. 892-895, (2002).

Legault, P., et al., "Order, dynamics and metal-binding in the lead-dependent ribozyme"., J. Mol. Biol., vol. 284, pp. 325-335, (1998).

Lehman, N., et al., "Evolution in vitro of an RNA enzyme with altered metal dependence"., Nature, vol. 361, pp. 182-185, (1993).

Lemieux, S., et al., "Modeling active RNA structures using the intersection of conformational space: application to the lead-activated ribozyme"., RNA, vol. 4, pp. 739-749, (1998).

Levy, M., et al., "ATP-Dependent Allosteric DNA Enzymes"., Chemistry & Biology, vol. 9, pp. 417-426, (2002).

Li, J., et al., "A highly sensitive and selective catalytic DNA biosensor for lead ions"., J. Am. Chem. Soc., vol. 122, No. 42, pp. 10466-10467, (2000).

Li, J., et al., "In vitro selection and characterization of a highly efficient Zn(II)-dependent RNA-cleaving deoxyribozyme"., Nucleic Acids Research, vol. 28, No. 2, pp. 481-488, (2000).

Li, J.J., et al., "Using molecular beacons as a sensitive fluorescence assay for enzymatic cleavage of single-stranded DNA"., Nucleic Acids Research, vol. 28, No. 11, e52, pp. i-vi, (2000).

Li, Y., et al., "A catalytic DNA for porphyrin metallation"., Nature Structural Biology, vol. 3, No. 9, pp. 743-747, (1996).

Li, Y., et al., "Capping DNA with DNA"., Biochemistry, vol. 19, No. 11, pp. 3106-3114, (2000).

Li, Y., et al., "Deoxyribozymes: new players in the ancient game of biocatalysis"., Current Opinion in Structural Biology, vol. 9, pp. 315-323, (1999).

Li, Y., et al., "Phosphorylating DNA with DNA"., Proc. Natl. Acad. Sci. USA, vol. 96, pp. 2746-2751, (1999).

Link, S., et al., "Alloy formation of gold-silver nanoparticles and the dependence of the plasmon absorption on their composition"., J. Phys. Chem. B, vol. 103, No. 18, pp. 3529-3533, (1999).

Liu, H-W., et al., "Determination of cadmium, mercury and lead in seawater by electrothermal vaporization isotope dilution inductively coupled plasma mass spectrometry"., Spectrochimica Acta Part B Atomic Spectroscopy 54, pp. 1367-1375, (1999).

Liu, J., et al., "A colorimetric lead biosensor using DNAzyme-directed assembly of gold nanoparticles", J. Am. Chem. Soc., vol. 125, No. 22, pp. 6642-6643, (2003).

Liu, J., et al., "Accelerated color change of gold nanoparticles assembled by DNAzymes for simple and fast colorimetric $Pb^{2+}$ detection"., J. Am. Chem. Soc., vol. 126, No. 39, pp. 12298-12305, (2004).

Liu, J., et al., "Adenosine-dependent assembly of aptazyme-functionalized gold nanoparticles and its application as a colorimetric biosensor"., Analytical Chemistry, vol. 76, No. 6, pp. 1627-1632, (2004).

Liu, J., et al., "Colorimetric biosensors based on DNAzyme-assembled gold nanoparticles"., Journal of Fluorescence, vol. 14, No. 4, pp. 343-354, (2004).

Liu, J., et al., "Highly dispersible molecular sieve carbon nanoparticles"., Chem. Mater., vol. 16, No. 22, pp. 4205-4207, (2004).

Liu, X., et al., "A fiber-optic evanescent wave DNA biosensor based on novel molecular beacons"., Analytical Chemistry, vol. 71, No. 22, pp. 5054-5059, (1999).

Liu, Z., et al., "Assemblage of signaling DNA enzymes with intriguing metal-ion specificities and pH dependences"., J. Am. Chem. Soc., vol. 125, No. 25, pp. 7539-7545, (2003).

Lohse, P.A., et al., "Ribozyme-catalysed amino-acid transfer reactions"., Nature, vol. 381, pp. 442-444, (1996).

Lorsch, J.R., et al., "In vitro evolution of new ribozymes with polynucleotide kinase activity"., Nature, vol. 371, pp. 31-36, (1994).

Lorsch, J.R., et al., "In vitro selection of RNA aptamers specific for cyanocobalamin"., Biochemistry, vol. 33, No. 4, pp. 973-982, (1994).

Lott, W.B., et al., "A two-metal ion mechanism operates in the hammerhead ribozyme-mediated cleavage of an RNA substrate"., Proc. Natl. Acad. Sci. USA, vol. 95, pp. 542-547, (1998).

Lu, Y., "New transition-metal-dependent DNAzymes as efficient endonucleases and as selective metal biosensors"., Chem. Eur. J., vol. 8, No. 20, pp. 4589-4596, (2002).

Lu, Y., et al., "New fluorescent and colorimetric DNAzyme biosensors for metal ions", Journal of Inorganic Biochemistry, vol. 96, issue 1, pp. 30, Abstract of the 11$^{th}$ International Conference on Biological Inorganic Chemistry; (Jul. 15, 2003).

Majerfeld, I., et al., "An RNA pocket for an aliphatic hydrophobe"., Structural Biology, vol. 1, No. 5, pp. 287-292, (1994).

Majerfeld, I., et al., "Isoleucine:RNA sites with associated coding sequences"., RNA, vol. 4, pp. 471-478, (1998).

Mannironi, C., et al., "In vitro selection of dopamine RNA ligands"., Biochemistry, vol. 36, No. 32, pp. 9726-9734, (1997).

Maoz, R., et al., "Penetration-controlled reactions in organized monolayer assemblies. 1. Aqueous permanganate interaction with monolayer and multilayer films of long-chain surfactants"., Langmuir, vol. 3, No. 6, pp. 1034-1044, (1987).

Marcus, A.H., et al., "Estimating the contribution of lead based paint to soil lead, dust lead, and childhood blood lead"., American Society for Testing and Materials Spec. STP 1226, pp. 12-23, (1995).

Marsh, T.C., et al., "A new DNA nanostructure, the G-wire, imaged by scanning probe microscopy"., Nucleic Acids Research, vol. 23, No. 4, pp. 696-700, (1995).

Matteucci, M.D., et al., "Synthesis of Deoxyoligonucleotides on a polymer support"., J. Am. Chem. Soc., vol. 103, No. 11, pp. 3185-3191, (1981).

Mecklenburg, M., et al., "A strategy for the broad range detection of compounds with affinity for nucleic acids"., Analytica Chimica Acta, vol. 347, pp. 79-86, (1997).

Mei, S.H.J., et al., "An efficient RNA-cleaving DNA enzyme that synchronizes catalysis with fluorescence signaling"., J. Am. Chem. Soc., vol. 125, No. 2, pp. 412-420, (2003).

Meli, M., et al., "Adenine-aptamer complexes: A bipartite RNA site that binds the adenine nucleic base"., The Journal of Biological Chemistry, vol. 277, No. 3, pp. 2104-2111, (2002).

Mirkin, C.A., et al., "A DNA-based method for rationally assembling nanoparticles into macroscopic materials"., Nature, vol. 382, pp. 607-609, (1996).

Mirkin, S.M., et al., "H-DNA and related structures"., Annu. Rev. Biophys. Biomol. Struct., vol. 23, pp. 541-576, (1994).

Miyawaki, A., et al. "Fluorescent indicators for $Ca^{2+}$ based on green fluorescent proteins and calmodulin"., Nature, vol. 388, pp. 882-887, (1997).

Mucic, R.C., et al., "Synthesis and characterization of DNA with ferrocenyl groups attached to their 5'-termini: electrochemical characterization of a redox-active nucleotide monolayer"., Chem. Commun., pp. 555-557, (1996).

Mullah, B., et al., "Automated synthesis of double dye-labeled oligonucleotides using tetramethylrhodamine (TAMRA) solid supports"., Tetrahedron Letters, vol. 38, No. 33, pp. 5751-5754, (1997).

Nazarenko, I.A., et al., "A closed tube format for amplification and detection of DNA based on energy transfer"., Nucleic Acids Research, vol. 26, No. 12, pp. 2516-2521, (1997).

Nazarenko, I.A., et al., "Defining a Smaller RNA Substrate for Elongation Factor Tu"., Biochemistry, vol. 34, No. 8, pp. 2545-2552, (1995).

Niemeyer, C.M., "Nanoparticles, proteins, and nucleic acids: Biotechnology meets materials science"., Angew. Chem. Int. Edition, vol. 40, pp. 4128-4158, (2001).

Nieuwlandt, D., et al., "In Vitro Selection of RNA Ligands to Substance P"., Biochemistry, vol. 34, No. 16, pp. 5651-5659, (1995).

Nissen, P., et al., "The structural basis of ribosome activity in peptide bond synthesis"., Science, vol. 289, pp. 920-930, (2000).

Nolte, A., et al., "Mirror-design of L-oligonucleotide ligands binding to L-arginine"., Nature Biotechnology, vol. 14, pp. 1116-1119, (1996).

Nutiu, R., et al., "Structure-switching signaling aptamers"., J. Am. Chem. Soc., vol. 125, No. 16, pp. 4771-4778, (2003).

Nuzzo, R.G., et al., "Spontaneously organized molecular assemblies. 3. Preparation and properties of solution adsorbed monolayers of organic disulfides on gold surfaces"., J. Am. Chem. Soc., vol. 109, No. 8, pp. 2358-2368, (1987).

O'Donnell, M.J., et al., "High-Density, Covalent Attachment of DNA to Silicon Wafers for Analysis by MALDI-TOF Mass Spectrometry"., Analytical Chemistry, vol. 69, No. 13, pp. 2438-2443, (1997).

Oehme, I., et al., "Optical sensors for determination of heavy metal ions"., Mikrochim. Acta, vol. 126, pp. 177-192, (1997).

Ohmichi, T., et al., "Role of $Nd^{3+}$ and $Pb^{2+}$ on the RNA cleavage reaction by a small ribozyme"., Biochemistry, vol. 36, No. 12, pp. 3514-3521, (1997).

Ohmichi, T., et al., "Effect of substrate RNA sequence on the cleavage reaction by a short ribozyme"., Nucleic Acids Research, vol. 26, No. 24, pp. 5655-5661, (1998).

Okazawa, A., et al., "In vitro selection of hematoporphyrin binding DNA aptamers"., Bioorganic & Medicinal Chemistry, Letters 10, pp. 2653-2656, (2000).

Ota, N., et al., "Effects of helical structures formed by the binding arms of DNAzymes and their substrates on catalytic activity"., Nucleic Acids Research, vol. 26, No. 14, pp. 3385-3391, (1998).

Pan, T., et al., "A small metalloribozyme with a two-step mechanism"., Nature, vol. 358, pp. 560-563, (1992).

Pan, T., et al., "In vitro selection of RNAs that undergo autolytic cleavage with $Pb^{2+}$"., Biochemistry, vol. 31, No. 16, pp. 3887-3895, (1992).

Pan, T., et al., "Properties of an in vitro selected $Pb^{2+}$ cleavage motif"., Biochemistry, vol. 33, No. 32, pp. 9561-9565, (1994).

Pan, W., et al., "Isolation of virus-neutralizing RNAs from a large pool of random sequences"., Proc. Natl. Acad. Sci. USA, vol. 92, pp. 11509-11513, (1995).

Park, S-J., et al., "Array-based electrical detection of DNA with nanoparticle probes"., Science, vol. 295, pp. 1503-1506, (2002).

Parsons, P.J., et al., "A rapid Zeeman graphite furnace atomic absorption spectrometric method for the determination of lead in blood"., Spectrochimica Acta, vol. 48B, No. 6/7, pp. 925-939, (1993).

Pavlov, A.R., et al., "Determination of lead in environmental water samples by a rapid and portable immunoassay"., Anyl, Book of Abstracts, 219th ACS National Meeting, San Francisco, CA, Mar. 26-30, 2000.

Pavlov, V., et al., "Aptamer-functionalized Au nanoparticles for the amplified optical detection of thrombin"., J. Am. Chem. Soc., vol. 126, No. 38, pp. 11768-11769, (2004).

Pearce, D.A., et al., "Peptidyl chemosensors incorporating a FRET mechanism for detection of Ni(II)"., Bioorganic & Medicinal Chemistry, Letters 8, pp. 1963-1968, (1998).

Pease, A.C., et al., "Light-generated oligonucleotide arrays for rapid DNA sequence analysis"., Proc. Natl. Acad. Sci. USA, vol. 91, pp. 5022-5026, (1994).

Piccirilli, J.A., et al., "Aminoacyl esterase activity of the tetrahymena ribozyme"., Science, New Series, vol. 256, issue 5062, pp. 1420-1424, (1992).

Pley, H.W., et al., "Three-dimensional structure of a hammerhead ribozyme"., Nature, vol. 372, pp. 68-74, (1994).

Potyrailo, R.A., et al., "Adapting selected nucleic acid ligands (aptamers) to biosensors"., Analytical Chemistry, vol. 70, No. 16, pp. 3419-3425, (1998).

Prudent, J.R., et al., "Expanding the scope of RNA catalysis"., Science, New Series, vol. 264, issue 5167, pp. 1924-1927, (1994).

Qiao, H., et al., "Transferability of blood lead determinations by furnace atomic absorption spectrophotometry and continuum background correction"., Clinical Chemistry, vol. 41, No. 10, pp. 1451-1454, (1995).

Rabinowitz, M., et al., "Home refinishing, lead paint, and infant blood lead levels"., American Journal of Public Health, vol. 75, No. 4, pp. 403-404, (1985).

Rajendran, M., et al., "Selecting nucleic acids for biosensor applications"., Combinatorial Chemistry and High Throughput Screening, vol. 5, No. 4, pp. 263-270, (2002).

Rakow, N.A., et al., "A colorimetric sensor array for odour visualization"., Nature, vol. 406, pp. 710-713, (2000).

Rink, S.M., et al., "Creation of RNA molecules that recognize the oxidative lesion 7,8-dihydro-8-hydroxy-2'-deoxyguanosine (8-oxodG) in DNA"., Proc. Natl. Acad. Sci. USA, vol. 95, pp. 11619-11624, (1998).

Robertson, M.P., et al., "Design and optimization of effector-activated ribozyme ligases"., Nucleic Acids Research, vol. 28, No. 8, pp. 1751-1759, (2000).

Robertson, M.P., et al., "In vitro selection of an allosteric ribozyme that transduces analytes to amplicons"., Nature Biotechnology, vol. 17, pp. 62-66, (1999).

Roth, A., et al., "An amino acid as a cofactor for a catalytic polynucleotide"., Proc. Natl. Acad. Sci. USA, vol. 95, pp. 6027-6031, (1998).

Roychowdhury-Saha, M., et al., "Flavin Recognition by an RNA Aptamer Targeted toward FAD"., Biochemistry, vol. 41, No. 8, pp. 2492-2499, (2002).

Ruckman, J., et al., "2'-Fluoropyrimidine RNA-based aptamers to the 165-amino acid form of vascular endothelial growth factor ($VEGF_{165}$) Inhibition of receptor binding and VEGF-induced vascular permeability through interactions requiring the exon 7-encoded domain"., The Journal of Biological Chemistry, vol. 273, No. 32, pp. 20556-20567, (1998).

Rurack, K., et al., "A selective and sensitive fluoroionophore for $Hg^{II}$, $Ag^{I}$, and $Cu^{II}$ with virtually decoupled fluorophore and receptor units"., J. Am. Chem. Soc., vol. 122, No. 5, pp. 968-969, (2000).

Rusconi, C.P., et al., "RNA aptamers as reversible antagonists of coagulation factor Ixa"., Nature, vol. 419, pp. 90-94, (2002).

Sabanayagam, C.R., et al., "Oligonucleotide immobilization on micropatterened streptavidin surfaces"., Nucleic Acids Research, vol. 28, No. 8, e33, pp. i-iv, (2000).

Santoro, S.W. et al., "Mechanism and utility of an RNA-cleaving DNA enzyme"., Biochemistry, vol. 37, No. 38, pp. 13330-13342, (1998).

Santoro, S.W., et al., "A general purpose RNA-cleaving DNA enzyme"., Proc. Natl. Acad. Sci. USA, vol. 94, pp. 4262-4266, (1997).

Santoro, S.W., et al., "RNA Cleavage by a DNA Enzyme with Extended Chemical Functionality"., J. Am. Chem. Soc., vol. 122, No. 11, pp. 2433-2439, (2000).

Sassanfar, M., et al., "An RNA motif that binds ATP"., Nature, vol. 364, pp. 550-553, (1993).

Schwartz, J., et al., "The risk of lead toxicity in homes with lead paint hazard"., Environmental Research, vol. 54, No. 1, pp. 1-7, (1991).

Scott, W.G., et al., "The crystal structure of an all-RNA hammerhead ribozyme: A proposed mechanism for RNA catalytic cleavage"., Cell, vol. 81, pp. 991-1002, (1995).

Scott, W.G., "RNA catalysis"., Current Opinion in Structural Biology, vol. 8, pp. 720-726, (1998).

Search results of key word search of medline, Mar. 26, 2000.

Search results of key word search on Chemical Abstracts, Mar. 24, 2000.

Search results of key word search from various databases, Mar. 24, 2000.

Seeman, N.C., et al., "Synthetic DNA knots and catenanes"., New Journal of Chemistry, vol. 17, pp. 739-755, (1993).

Seeman, N.C., et al., "Emulating biology: Building nanostructures from the bottom up"., Proc. Natl. Acad. Sci., vol. 99, suppl. 2, pp. 6451-6455, (2002).

Seeman, N.C., "DNA in a material world"., Nature, vol. 421, pp. 427-431, (2003).

Seetharaman, S., et al., "Immobilized RNA switches for the analysis of complex chemical and biological mixtures"., Nature Biotechnology, vol. 19, pp. 336-341, (2001).

Sen, D., et al., "DNA enzymes"., Current Opinion in Chemical Biology, vol. 2, pp. 680-687, (1998).

Shaiu, W-L., et al., "Atomic force microscopy of oriented linear DNA molecules labeled with 5nm gold spheres"., Nucleic Acids Research, vol. 21, No. 1, pp. 99-103, (1993).

Shaw, S.Y., et al., "Knotting of a DNA chain during ring closure"., Science, New Series, vol. 260, issue 5107, pp. 533-536, (1993).

Shekhtman, E.M., et al., "Stereostructure of replicative DNA catenanes from eukaryotic cells"., New Journal of Chemistry, vol. 17, pp. 757-763, (1993).

Sigurdsson, S.T., et al., "Small ribozymes"., RNA Structure and Function, Cold Spring Harbor Laboratory Press (Monograph 35), pp. 339-375, (1998).

Singh, K.K., et al., "Fluorescence Polarization for Monitoring Ribozyme Reactions in Real-Time"., Biotechniques, vol. 29, No. 2, pp. 344-351, (2000).

Smith, F.W., et al., "Quadruplex structure of oxytricha telomeric DNA oligonucleotides"., Nature, vol. 356, pp. 164-168, (1992).

Smith, J.O., et al., "Molecular recognition of PNA-containing hybrids: Spontaneous assembly of helical cyanine dye aggregates on PNA templates"., J. Am. Chem. Soc., vol. 121, No. 12, pp. 2686-2695, (1999).

Soriaga, M.P., et al., "Determination of the orientation of aromatic molecules adsorbed on platinum electrodes: The effect of solute concentration"., J. Am. Chem. Soc., vol. 104, No. 14, pp. 3937-3945, (1982).

Soukup, G.A., et al., "Engineering precision RNA molecular switches"., Proc. Natl. Acad. Sci. USA, vol. 96, pp. 3584-3589, (1999).

Soukup, G.A., et al., "Allosteric nucleic acid catalysts"., Current Opinion in Structural Biology, vol. 10, pp. 318-325, (2000).

Srisawat, C., et al., "Sephadex-binding RNA ligands: rapid affinity purification of RNA from complex RNA mixtures"., Nucleic Acids Research, vol. 29, No. 2 e4, pp. 1-5, (2001).

Stage-Zimmermann, T.K., et al., "Hammerhead ribozyme kinetics"., RNA, vol. 4, pp. 875-889, (1998).

Stojanovic, M.N., et al., "Aptamer-based colorimetric probe for cocaine"., J. Am. Chem. Soc., vol. 124, No. 33, pp. 9678-9679, (2002).

Stojanovic, M.N., et al., "Aptamer-based folding fluorescent sensor for cocaine"., Journal of the American Chemical Society, vol. 123, No. 21, pp. 4928-4931, (2001).

Stojanovic, M.N., et al., "Fluorescent sensors based on aptamer self-assembly"., Journal of the American Chemical Society, vol. 122, No. 46, pp. 11547-11548, (2000).

Storhoff, J.J., et al., "Programmed materials synthesis with DNA"., Chem. Rev., vol. 99, No. 7, pp. 1849-1862, (1999).

Storhoff, J.J., et al., "Facile colorimetric detection of polynucleotides based on gold nanoparticle probes"., Proceedings of the 1998 ERDEC Scientific Conference on Chemical and Biological Defense Research, Nov. 17-20, 1998, Aberdeen Proving Ground, pp. 221-226, (1999).

Storhoff, J.J., et al., "What Controls the Optical Properties of DNA-Linked Gold Nanoparticle Assemblies?"., J. Am. Chem. Soc., vol. 122, No. 19, pp. 4640-4650, (2000).

Storhoff, J.J., et al., "One-pot colorimetric differentiation of polynucleotides with single base imperfections using gold nanoparticle probes"., Journal of the American Chemical Society, vol. 120, No. 9, pp. 1959-1964, (1998).

Streicher, B., et al., "Lead cleavage site in the core structure of group I intron-RNA"., Nucleic Acids Research, vol. 21, No. 2, pp. 311-317, (1993).

Sugimoto, N., et al., "Site-specific cleavage reaction catalyzed by leadzyme is enhanced by combined effect of lead and rare earth ions"., FEBS Letters, vol. 393, pp. 97-100, (1996).

Sun, L.Q., et al., "Catalytic nucleic acids: From lab to applications"., Pharmacological Reviews, vol. 52, pp. 325-347, (2000).

Tahan, J.E., et al., "Electrothermal atomic absorption spectrometric determination of Al, Cu, Ge, Pb, V and Zn in clinical samples and in certified environmental reference materials"., Analytica Chimica Acta, vol. 295, pp, 187-197, (1994).

Takagi, Y., et al., "Survey and Summary: Recent advances in the elucidation of the mechanisms of action of ribozymes"., Nucleic Acids Research, vol. 29, No. 9, pp. 1815-1834, (2001).

Tang, J., et al., "Rational design of allosteric ribozymes"., Chemistry & Biology, vol. 4, No. 6, pp. 453-459, (1997).

Tang, J., et al., "Structural diversity of self-cleaving ribozymes"., Proc. Natl. Acad. Sci. USA, vol. 97, No. 11, pp. 5784-5789, (2000).

Tanner, N.K., "Biochemistry of hepatitis delta virus catalytic RNAs"., Ribozymes in the Gene Therapy of Cancer, Chapter 3, pp. 23-38, (1998).

Tao, J., et al., "Arginine-Binding RNAs Resembling TAR Identified by in Vitro Selection".,Biochemistry, vol. 35, No. 7, pp. 2229-2238, (1996).

Tarasow, T.M., et al., "RNA-catalysed carbon-carbon bond formation"., Nature, vol. 389, pp. 54-57, (1997).

Telting-Diaz, M., et al., "Mass-produced ionophore-based fluorescent microspheres for trace level determination of lead ions"., Analytical Chemistry, vol. 74, No. 20, pp. 5251-5256, (2002).

Thompson, R.B., et al., "Determination of Picomolar Concentrations of Metal Ions Using Fluorescence Anisotropy: Biosensing with a "Reagentless" Enzyme Transducer"., Analytical Chemistry, vol. 70, No. 22, pp. 4717-4723, (1998).

Timmons, C.O., et al., "Investigation of Fatty Acid Monolayers on Metals by Contact Potential Measurements", Journal of Physical Chemistry, vol. 69, No. 3, pp. 984-990, (1965).

Tompkins, H.G., et al., "The study of the gas-solid interaction of acetic acid with a cuprous oxide surface using reflection-absorption spectroscopy"., Journal of Colloid and Interface Science, vol. 49, No. 3, pp. 410-421, (1974).

Travascio, P., et al., "A ribozyme and a catalytic DNA with peroxidase activity: active sites versus cofactor-binding sites"., Chemistry & Biology, vol. 6, No. 11, pp. 779-787, (1999).

Tsang, J., et al., "In vitro evolution of randomized ribozymes"., Methods in Enzymology, vol. 267, pp. 410-426, (1996).

Tsien, R.Y., "Fluorescent and photochemical probes of dynamic biochemical signals inside living cells"., Fluorescent Chemosensors for Ion and Molecule Recognition, (ed. Czarnik, A. W.), chapter 9, pp. 130-146, American Chemical Society, (1993).

Tuerk, C., et al., "RNA pseudoknots that inhibit human immunodeficiency virus type 1 reverse transcriptase"., Proc. Natl. Acad. Sci. USA, vol. 89, pp. 6988-6992, (1992).

Tuerk, C., et al., "Systematic evolution of ligands by exponential enrichment: RNA ligands to bacteriophage T4 DNA polymerase"., Science, New Series, vol. 249, issue 4968, pp. 505-510, (1990).

Tyagi, S., et al., "Molecular Beacons: Probes that fluoresce upon hybridization"., Nature Biotechnology, vol. 14, pp. 303-308, (1996).

Tyagi, S., et al., "Multicolor molecular beacons for allele discrimination"., Nature Biotechnology, vol. 16, pp. 49-53, (1998).

Tyagi, S., et al., "Wavelength-shifting molecular beacons"., Nature Biotechnology, vol. 18, pp. 1191-1196, (2000).

Ueyama, H., "A novel potassium sensing in aqueous media with a synthetic oligonucleotide derivative. Fluorescence resonance energy transfer associated with guanine quartet-potassium ion complex formation"., J. Am. Chem. Soc., vol. 124, No. 48, pp. 14286-14287, (2002).

Uphoff, K.W., et al., "In vitro selection of aptamers: the dearth of pure reason"., Current Opinion in Structural Biology, vol. 6, pp. 281-288, (1996).

Vaish, N.K., et al., "In vitro selection of a purine nucleotide-specific hammerhead-like ribozyme"., Proc. Natl. Acad. Sci. USA, vol. 95, pp. 2158-2162, (1998).

Valadkhan, S., et al., "Splicing-related catalysis by protein-free snRNAs"., Nature, vol. 413, pp. 701-707, (2001).

Vianini, E., et al., "In vitro selection of DNA aptamers that bind L-tyrosinamide"., Bioorganic & Medicinal Chemistry, vol. 9, pp. 2543-2548, (2001).

Walkup, G.K., et al., "Design and Evaluation of a Peptidyl Fluorescent Chemosensor for Divalent Zinc"., J. Am. Chem. Soc., vol. 118, No. 12, pp. 3053-3054, (1996).

Wallace, S.T., et al., In vitro selection and characterization of streptomycin-binding RNAs: recognition discrimination between antibiotics. RNA, vol. 4, pp. 112-123, (1998).

Wallis, M.G., et al., "A novel RNA motif for neomycin recognition"., Chemistry & Biology, vol. 2, No. 8, pp. 543-552, (1995).

Wallis, M.G., et al., "In vitro selection of a viomycin-binding RNA pseudoknot"., Chemistry & Biology, vol. 4, No. 5, pp. 357-366, (1997).

Walter, F., et al., "Folding of the four-way RNA junction of the hairpin ribozyme"., Biochemistry, vol. 37, No. 50, pp. 17629-17636, (1998).

Walter, N.G., et al., "The hairpin ribozyme: structure, assembly and catalysis"., Current Opinion in Chemical Biology, vol. 2, pp. 24-30, (1998).

Wang, D.Y., et al., "A general strategy for effector-mediated control of RNA-cleaving ribozymes and DNA enzymes"., J. Mol. Biol., vol. 318, pp. 33-43, (2002).

Wang, F., et al., "Sphingosine-1-phosphate Inhibits Motility of Human Breast Cancer Cells Independently of Cell Surface Receptors"., Cancer Research, vol. 59, pp. 6185-6191, (1999).

Wang, J., "Survey and Summary: From DNA biosensors to gene chips"., Nucleic Acids Research, vol. 28, No. 16, pp. 3011-3016, (2000).

Wang, K.Y., et al., "A DNA aptamer which binds to and inhibits thrombin exhibits a new structural motif for DNA"., Biochemistry, vol. 32, No. 8, pp. 1899-1904, (1993).

Wang, Y., et al., "Assembly and characterization of five-arm and six-arm DNA branched junctions"., Biochemistry, vol. 30, pp. 5667-5674, (1991).

Wang, Y., et al., "RNA molecules that specifically and stoichiometrically bind aminoglycoside antibiotics with high affinities"., Biochemistry, vol. 35, No. 38, pp. 12338-12346, (1996).

Wecker, M., et al., "In vitro selection of a novel catalytic RNA: characterization of a sulfur alkylation reaction and interaction with a small peptide"., RNA, vol. 2, pp. 982-994, (1996).

Wedekind, J.E., et al., "Crystal structure of a lead-dependent ribozyme revealing metal binding sites relevant to catalysis"., Nature Structural Biology, vol. 6, No. 3, pp. 261-268, (1999).

Wedekind, J.E., et al., "Crystal structure of the leadzyme at 1.8 Å Resolution: Metal ion binding and the implications for catalytic mechanism and allo site ion regulation"., Biochemistry, vol. 42, No. 32, pp. 9554-9563, (2003).

Wells, R.D., "Unusual DNA structures"., Journal of Biological Chemistry, vol. 263, No. 3, pp. 1095-1098, (1988).

Werstuck, G., et al., "Controlling gene expression in living cells through small molecule-RNA interactions"., Science, vol. 282, pp. 296-298, (1998).

Whaley, S.R., et al., "Selection of peptides with semiconductor binding specificity for directed nanocrystal assembly"., Nature, vol. 405, pp. 665-668, (2000).

Whitesides, G.M., et al., "Self-assembled monolayers and lithography"., Proceedings of the Robert A. Welch Foundation 39th Conference on Chemical Research on Nanophase Chemistry, pp. 109-121, Houston, TX, Oct. 23-24, 1995.

Wiegand, T.W., et al., "High-affinity oligonucleotide ligands to human IgE inhibit binding to Fc epsilon receptor I"., The Journal of Immunology, vol. 157, pp. 221-230, (1996).

Wiegand, T.W., et al., "Selection of RNA amide synthases"., Chemistry & Biology, vol. 4, No. 9, pp. 675-683, (1997).

Williams, K.P., et al., "Bioactive and nuclease-resistant L-DNA ligand of vasopressin"., Proc. Natl. Acad. Sci. USA, vol. 94, pp. 11285-11290, (1997).

Williams, K.P., et al., "Selection of novel $Mg^{2+}$-dependent self-cleaving ribozymes" The EMBO Journal, vol. 14, No. 18, pp. 4551-4557, (1995).

Wilson, C., et al., "Functional requirements for specific ligand recognition by a biotin-binding RNA Pseudoknot"., Biochemistry, vol. 37, No. 41, pp. 14410-14419, (1998).

Wilson, C., et al., "In vitro evolution of a self-alkylating ribozyme"., Nature, vol. 374, pp. 777-782, (1995).

Wilson, C., et al., "Isolation of a fluorophore-specific DNA aptamer with weak redox activity"., Chemistry & Biology, vol. 5, No. 11, pp. 609-617, (1998).
Wilson, D.S., et al., "In vitro selection of functional nucleic acids"., Annu. Rev. Biochem. vol. 68, pp. 611-647, (1999).
Winkler, J.D., et al., "Photodynamic Fluorescent Metal Ion Sensors with Parts per Billion Sensitivity"., J. Am. Chem. Soc., vol. 120, No. 13, pp. 3237-3242, (1998).
Wittmann, C., et al.,"Microbial and Enzyme sensors for environmental monitoring"., Handbook of Biosensors and Electronic Noses: Medicine, Food, and the Environment, pp. 299-332, (1997).
Xia, P., et al., "Activation of Sphingosine Kinase by Tumor Necrosis Factor-α Inhibits Apoptosis in Human Endothelial Cells"., Journal of Biological Chemistry, vol. 274, No. 48, pp. 34499-34505, (1999).
Yan, H., et al., "DNA-Templated self-assembly of protein arrays and highly conductive nanowires"., Science, vol. 301, pp. 1882-1884, (2003).
Yang, Q., et al., "DNA ligands that bind tightly and selectively to cellobiose"., Proc. Natl. Acad. Sci. USA, vol. 95, pp. 5462-5467, (1998).
English Translation of Yang, Y., et al., "Measurement of lead and magnesium in distilled spirits using inductively coupled plasma optical emission spectrometry viewed from the end"., Analytical Chemistry (Fenxi Huaxue), Chinese Journal of Analytical Chemistry, vol. 25, No. 9, pp. 1114-1117, (1997).
Yurke, B., et al., "A DNA-fuelled molecular machine made of DNA"., Nature, vol. 406, pp. 605-608, (2000).
Zhang, B., et al., "Peptide bond formation by in vitro selected ribozymes"., Nature, vol. 390, pp. 96-100, (1997).
Zhang, P., et al., "Design of a molecular beacon DNA probe with two fluorophores"., Angewandte Chemie International Edition, vol. 40, No. 2, pp. 402-405, (2001).
Zillmann, M., et al., "In vitro optimization of truncated stem-loop II variants of the hammerhead ribozyme for cleavage in low concentrations of magnesium under non-turnover conditions"., RNA, vol. 3, pp. 734-747, (1997).
Zimmerman, J.M., et al., "In vivo selection of spectinomycin-binding RNAs"., Nucleic Acids Research, vol. 30, No. 24, pp. 5425-5435, (2002).
Zimmermann, G.R., et al., "Molecular interactions and metal binding in the theophylline-binding core of an RNA aptamer"., RNA, vol. 6, pp. 659-667, (2000).
International Search Report dated Nov. 21, 2005 for PCT application No. PCT/US2005/001060.
Supplemental International Search Report dated Jan. 10, 2006 for PCT application No. PCT/US2005/001060.
Liu, J., et al., "Size control, metal substitution, and catalytic application of cryptomelane nanomaterials prepared using cross-linking reagents"., Chem. Mater., vol. 16, No. 2, pp. 276-285, (2004).
Cake, K.M., et al., "Partition of circulating lead between serum and red cells is different for internal and external sources of lead"., American Journal of Industrial Medicine, vol. 29, pp. 440-445, (1996).
International Search Report dated Aug. 31, 2004 for PCT application No. PCT/US2004/002946.
Hazarika, P., et al., "Reversible switching of DNA-Gold nanoparticle aggregation"., Angewandte Chemie International Edition, vol. 43, No. 47, pp. 6469-6471, (2004).
International Search Report dated May 29, 2006 for PCT application No. PCT/US2005/037896.
Liu, J., et al., "Improving fluorescent DNAzyme biosensors by combining Inter- and Intramolecular quenchers"., Analytical Chemistry, vol. 75, No. 23, pp. 6666-6672, (2003).
Liu, J., et al., "Stimuli-responsive disassembly of nanoparticle aggregates for light-up colorimetric sensing"., Journal of the American Chemical Society, vol. 127, No. 36, pp. 12677-12683, (2005).
European Search Report dated Jul. 10, 2006 for PCT application No. PCT/US2003/12576.
Tanner, F.C., et al., "Transfection of human endothelial cells"., Cardiovascular research, vol. 35, pp. 522-528, (1997).
International Search Report dated Nov. 17, 2006 for PCT application No. PCT/US2006/001627.

Liu, J., et al., "DNAzyme-directed assembly of gold nanoparticles as colorimetric sensor for a broad range of analytes", pp. 1-3, located at http://ieeenano2003.arc.nasa.gov/THM@.pdf, (2003).
Wang, D.Y., et al., "A general approach for the use of oligonucleotide effectors to regulate the catalysis of RNA-cleaving ribozymes and DNAzymes", Nucleic Acids Research, vol. 30, No. 8, pp. 1735-1742, (2002).
Levy, M., et al., "Exponential growth by cross-catalytic cleavage of deoxyribozymogens",PNAS, vol. 100, No. 11, pp. 6416-6421, (2003).
Beyer, S., et al., "A modular DNA signal translator for the controlled release of a protein by an aptamer", Nucleic Acids Research, vol. 34, No. 5, pp. 1581-1587, (2006).
Frauendorf, C., et al., "Detection of small organic analytes by fluorescing molecular switches", Bioorganic & Medicinal Chemistry, vol. 9, pp. 2521-2524, (2001).
Glynou, K., et al., "Oligonucleotide-functionalized gold nanoparticles as probes in a dry-reagent strip biosensor for DNA analysis by hybridization", Anal. Chem, vol. 75, No. 16, pp. 4155-4160, (2003).
Liu, J., et al., "Optimization of a $Pb^{2+}$-directed gold nanoparticle/DNAzyme assembly and its application as a colorimetric biosensor for $Pb^{2+}$", Chem. Mater., vol. 16, No. 17, pp. 3231-3238, (2004).
Jones, K.D., et al., "Anniversary Essays, 3. Assay development, Changes in the development of rapid assays since 1995", Medical Devicelink, found at: http://www.devicelink.com/ivdt/archive/05/04/005.html, 3 pages, (2005).
Product Description: Pall Corporation, "Immunochromatographic, lateral flow or strip tests development ideas", found at: http://www.pall.com/34445_4154.asp, 7 pages, (1998).
Liu, J., et al., "Fast colorimetric sensing of adenosine and cocaine based on a general sensor design involving aptamers and nanoparticles", Angew. Chem. Int. Ed., vol. 45, pp. 90-94, (2006).
Liu, J., et al., "A simple and sensitive "dipstick" test in serum based on lateral flow separation of aptamer-linked nanostructures", Angewandte Chemie International Edition, vol. 45, pp. 7955-7959, (2006).
Liu, J. et al., "Colorimetric Cu2+ detection with a ligation DNAzyme and nanoparticles", Chemical Communications, Advance Articles, DOI: 10.1039/b712421j, 6 pages, Oct. 24, 2007.
Liu, J. et al., "Non-Base pairing DNA provides a new dimension for controlling aptamer-linked nanoparticles and sensors", Journal of the American Chemical Society, vol. 129, No. 27, pp. 8634-8643, (2007).
Liu, J. et al., "Supporting Information for Colorimetric Cu2+ detection with a ligation DNAzyme and nanoparticles", Chemical Communications, Advance Articles, 4 pages, Oct. 24, 2007.
Stratagene Catolog, "Gene Characterization Kits", 2 pages, (1988).
Jiang, P. et al., "Fluorescent detection of zinc in biological systems: recent development on the design of chemosensors and biosensors", Coordination Chemistry Reviews, vol. 248, pp. 205-229, (2004).
Lim, M.H. et al., "Metal-based turn-on fluorescent probes for sensing nitric oxide", Accounts of Chemical Research, vol. 40, No. 1, pp. 41-51, (2007).
Yoon, S. et al., "Screening mercury levels in fish with a selective fluorescent chemosensor", Journal of the American Chemical Society, vol. 127, pp. 16030-16031, (2005).
Yang, L. et al., "Imaging of the intracellular topography of copper with a fluorescent sensor and by synchrotron x-ray fluorescence microscopy", Proceedings of the National Academy of Science, vol. 102, No. 32, pp. 11179-11184, (2005).
He, Q. et al., "A selective fluorescent sensor for detecting lead in living cells", Journal of the American Chemical Society, vol. 128, pp. 9316-9317, (2006).
Zeng, L. et al., "A selective turn-on fluorescent sensor for imaging copper in living cells", Journal of the American Chemical Society, vol. 128, pp. 10-11, (2006).
Wegner, S.V. et al., "Design of an emission ratiometric biosensor from MerR family proteins: A sensitive and selective sensor for $Hg^{2+}$", Journal of the American Chemical Society, vol. 129, pp. 3474-3475, (2007).

Nolan, E.M. et al., "Turn-on and ratiometric mercury sensing in water with a red-emitting probe", Journal of the American Chemical Society, vol. 129, pp. 5910-5918, (2007).

Sasaki, D.Y. et al., "Metal-induced dispersion of lipid aggregates: A simple, selective, and sensitive fluorescent metal ion sensor", Angew. Chem. Int. Ed. England, vol. 34, No. 8, pp. 905-907, (1995).

Torrado, A. et al., "Exploiting polypeptide motifs for the design of selective Cu(II) ion chemosensors" Journal of the American Chemical Society, vol. 120, pp. 609-610, (1998).

Grandini, P. et al., "Exploiting the self-assembly strategy for the design of selective $Cu^{II}$ ion chemosensors", Angew. Chem. Int. Ed, vol. 38, No. 20, pp. 3061-3064, (1999).

Klein, G. et al., "A fluorescent metal sensor based on macrocyclic chelation", Chem. Comm., pp. 561-562, (2001).

Zheng, Y. et al., "A new fluorescent chemosensor for copper ions based on tripeptide glycyl-histidyl-lysine (GHK)", Organic Letters, vol. 3, No. 21, pp. 3277-3280, (2001).

Boiocchi, M. et al., "A two-channel molecular dosimeter for the optical detection of copper(II)" Chem. Comm, pp. 1812-1813, (2003).

Zheng, Y. et al., "Peptidyl fluorescent chemosensors for the detection of divalent copper", Analytical Chemistry, vol. 75, No. 7, pp. 1706-1712, (2003).

Zheng, Y. et al., "Development of fluorescent film sensors for the detection of divalent copper", Journal of the American Chemical Society, vol. 125, pp. 2680-2686, (2003).

Roy, B.C. et al., "Synthesis of new, pyrene-containing metal-chelating lipids and sensing of cupric ions", Organic Letters, vol. 5, No. 1, pp. 11-14, (2003).

Kaur, S. et al., "Photoactive chemosensors 4: a $Cu^{2+}$ protein cavity mimicking fluorescent chemosensor for selective $Cu^{2+}$ recognition", Tetrahedron Letters, vol. 45, pp. 5081-5085, (2004).

Mei, Y. et al., "A selective and sensitive chemosensor for $Cu^{2+}$ based on 8-hydroxyquinoline", Tetrahedron Letters, vol. 47, pp. 2447-2449, (2006).

Zhang, X-B. et al., "A highly selective fluorescent sensor for $Cu^{2+}$ based on 2-(2'-hydroxyphenyl)benzoxazole in a poly(vinyl chloride) matrix", Analytica Chimica Acta, vol. 567, pp. 189-195, (2006).

Comba, P. et al., "Synthesis of new phenanthroline-based heteroditopic ligands—highly efficient and selective fluorescence sensors for copper (II) ions", European Journal of Inorganic Chemistry, pp. 4442-4448, (2006).

Kim, S. H. et al., "$Hg^{2+}$-selective off-on and $Cu^{2+}$-selective on-off type fluoroionophore based upon cyclam", Organic Letters, vol. 8, No. 3, pp. 371-374, (2006).

White, B. R. et al., "Fluorescent peptide sensor for the selective detection of $Cu^{2+}$", Talanta, vol. 71, pp. 2015-2020, (2007).

Oter, O. et al., "Spectral characterization of a newly synthesized fluorescent semicarbazone derivative and its usage as a selective fiber optic sensor for copper(II)", Analytica Chimica Acta, vol. 584, pp. 308-314, (2007).

Dujols, V. et al., "A long-wavelength fluorescent chemodosimeter selective for Cu(II) ion in water", Journal of the American Chemical Society, vol. 119, pp. 7386-7387, (1997).

Yang, J-S. et al., "$Cu^{2+}$-induced blue shift of the pyrene excimer emission: a new signal transduction mode of pyrene probes", Organic Letters, vol. 3, No. 6, pp. 889-892, (2001).

Kaur, S. et al., "Photoactive chemosensors 3: a unique case of fluorescence enhancement with Cu(II)", Chem. Comm., pp. 2840-2841, (2002).

Wu, Q. et al., "Catalytic signal amplification using a heck reaction. An example in the fluorescence sensing of Cu(II)", Journal of the American Chemical Society, vol. 126, pp. 14682-14683, (2004).

Royzen, M. et al., "Ratiometric displacement approach to Cu(II) sensing by fluorescence", Journal of the American Chemical Society, vol. 127, pp. 1612-1613, (2005).

Xu, Z. et al., "Ratiometric and selective fluorescent sensor for $Cu^{II}$ based on internal charge transfer (ICT)", Organic Letters, vol. 7, No. 5, pp. 889-892, (2005).

Wen, Z-C. et al., "A highly selective charge transfer fluoroionophore for $Cu^{2+}$", Chem. Commun., pp. 106-108, (2006).

Yang, H. et al., "Highly selective ratiometric fluorescent sensor for Cu(II) with two urea groups", Tetrahedron Letters, vol. 47, pp. 2911-2914, (2006).

Martinez, R. et al., "2-aza-1,3-butadiene derivatives featuring an anthracene or pyrene unit: highly selective colorimetric and fluorescent signaling of $Cu^{2+}$ cation", Organic Letters, vol. 8, No. 15, pp. 3235-3238, (2006).

Navani, N.K. et al., "Nucleic acid aptamers and enzymes as sensors", Current Opinion in Chemical Biology, vol. 10, pp. 272-281, (2006).

Liu, J. et al., "A catalytic beacon sensor for uranium with parts-per-trillion sensitivity and millionfold selectivity", Proceedings of the National Academy of Science, vol. 104, No. 7, pp. 2056-2061, (2007).

Georgopoulos, P.G. et al., "Environmental copper: its dynamics and human exposure issues", Journal of Toxicology and Environmental Health, Part B, vol. 4, pp. 341-394, (2001).

Hertzberg, R.P. et al., "Cleavage of DNA with methidiumpropyl-EDTA-iron(II): reaction conditions and product analyses", Biochemistry, vol. 23, pp. 3934-3945, (1984).

Yazzie, M. et al., "Uranyl acetate causes DNA single strand breaks in vitro in the presence of ascorbate (Vitamin C)", Chem. Res. Toxicol., vol. 16, pp. 524-530, (2003).

Bolletta, F. et al., "A [$Ru^{II}$ (bipy)3]-[1,9-diamino-3,7-diazanonane-4,6-dione] two-component system as an efficient on-off luminescent chemosensor for $Ni^{2+}$ and $Cu^{2+}$ in water, based on an ET (energy transfer) mechanism", Journal of the Chemical Society, Dalton Transactions, pp. 1381-1385, (1999).

Carmi, N. et al., "Characterization of a DNA-cleaving deoxyribozyme", Bioorganic & Medicinal Chemistry, vol. 9, issue 10, pp. 2589-2600, (2001).

Liu, J. et al., "A DNAzyme catalytic beacon sensor for paramagnetic $Cu^{2+}$ ions in aqueous solution with high sensitivity and selectivity", Journal of the American Chemical Society, 2 pages, (2007), ASAP Web Release Date: Jul. 24, 2007.

Tanaka, K. et al., "Programmable self-assembly of metal ions inside artificial DNA duplexes", Nature Nanotechnology, vol. 1, pp. 190-194, (2006).

Achenbach, J.C. et al., "DNAzymes: From creation in vitro to application in vivo", Current Pharmaceutical Biotechnology, vol. 5, pp. 321-336, (2004).

Balaji, T. et al., "Optical sensor for the visual detection of mercury using mesoporous silica anchoring porphyrin moiety", The Analyst, vol. 130, pp. 1162-1167, (2005).

Caballero, A. et al., "Highly selective chromogenic and redox or fluorescent sensors of $Hg^{2+}$ in aqueous environment based on 1,4-disubstituted azines", Journal of the American Chemical Society, vol. 127, pp. 15666-15667, (2005).

Chan, W.H. et al., "Development of a mercury ion-selective optical sensor based on fluorescence quenching of 5,10,15, 20-tetraphenylporphyrin", Analytica Chimica Acta, vol. 444, pp. 261-269, (2001).

Chen, P. et al., "A general strategy to convert the merR family proteins into highly sensitive and selective fluorescent biosensors for metal ions", Journal of the American Chemical Society, vol. 126, pp. 728-729, (2004).

Chiuman, W. et al., "Efficient signaling platforms built from a small catalytic DNA and doubly labeled fluorogenic substrates", Nucleic Acids Research, vol. 35, No. 2, pp. 401-405, (2007).

Cruz, R.P.G. et al., "Dinucleotide junction cleavage versatility of 8-17 deoxyribozyme", Chemistry & Biology, vol. 11, pp. 57-67, (2004).

Frasco, M.F. et al., "Mechanisms of cholinesterase inhibition by inorganic mercury", the FEBS Journal, vol. 274, pp. 1849-1861, (2007).

Guo, X. et al., "A highly selective and sensitive fluorescent chemosensor for $Hg^{2+}$ in neutral buffer aqueous solution", The Jouranl of the American Chemical Society, vol. 126, pp. 2272-2273, (2004).

Harris, H.H. et al., "The chemical form of mercury in fish", Science, vol. 301, pp. 1203, (2003).

Ha-Thi, M-H. et al., "Highly selective and sensitive phosphane sulfide derivative for the detection of $Hg^{2+}$ in an organoaqueous medium", Organic Letters, vol. 9, No. 6, pp. 1133-1136, (2007).

Joyce, G.F. et al., "Directed evolution of nucleic acid enzymes", Annual Review Biochem., vol. 73, pp. 791-836, (2004).

Ko, S-K. et al., "In vivo monitoring of mercury ions using a rhodamine-based molecular probe", Journal of the American Chemical Society, vol. 128, pp. 14150-14155, (2006).

Kuswandi, B. et al., "Capillary optode: determination of mercury(II) in aqueous solution", Analytical Letters, vol. 32, No. 9. 4, pp. 649-664, (1999).

Kuswandi, B. et al., "Selective pool optode for mercury ion sensing in aqueous solution", Sensors and Actuators B, vol. 74, pp. 131-137, (2001).

Lee, J-S. et al., "Colorimetric detection of mercuric ion ($Hg^{2+}$) in aqueous media using DNA-functionalized gold nanoparticles", Angewandte Chemie International Edition, vol. 46, pp. 4093-4096, (2007).

Liu, B. et al., "A selective fluorescent ratiometric chemodosimeter for mercury ion", Chem. Communications, pp. 3156-3158, (2005).

Liu, J. et al., "Fluorescent DNAzyme biosensors for metal ions based on catalytic molecular beacons", Methods in Molecular Biology, vol. 335, pp. 275-288, (2006).

Matsushita, M. et al., "A blue fluorescent antibody-cofactor sensor for mercury", Organic Letters, vol. 7, No. 22, pp. 4943-4946, (2005).

Miyake, Y. et al., "$Mercury^{II}$-mediated formation of thymine-$Hg^{II}$-thymine base pairs in DNA duplexes", Journal of the American Chemical Society, vol. 128, No. 7, pp. 2172-2173, (2006).

Nolan, E.M. et al., "A "turn-on" fluorescent sensor for the selective detection of mercuric ion in aqueous media", Journal of the American Chemical Society, vol. 125, pp. 14270-14271, (2003).

Ono, A. et al., "highly selective oligonucleotide-based sensor for mercury (II) in aqueous solutions", Angew. Chem. Int. Ed., vol. 43, pp. 4300-4302, (2004).

Ostatna, V. et al., "Self-assembled monolayers of thiol-end-labeled DNA at mercury electrodes", Langmuir, vol. 22, pp. 6481-6484, (2006).

Prodi, L. et al., "An effective fluorescent achemosensor for mercury ions", Journal of the American Chemical Society, vol. 122, No. 28, pp. 6769-6770, (2000).

Silverman, S.K., "Survey and Summary: In vitro selection, characterization, and application of deoxyribozymes that cleave RNA", Nucleic Acids Research, vol. 33, No. 19, pp. 6151-6163, (2005).

Song, K.C. et al., "Fluorogenic $Hg^{2+}$-selective chemodosimeter derived from 8-hydroxyquinoline", Organic Letters, vol. 8, No. 16, pp. 3413-3416, (2006).

Szurdoki, F. et al., "A combinatorial approach to discover new chelators for optical metal ion sensing", Analytical Chemistry, vol. 72, No. 21, pp. 5250-5257, (2000).

Tanaka, Y. et al., "$^{15}N$-$^{15}N$ J-coupling across $Hg^{II}$: Direct observation of $Hg^{II}$-mediated T-T base pairs in a DNA duplex" Journal of the American Chemical Society, vol. 129, No. 2, pp. 244-245, (2007).

Jacoby, M. "Mercury Sensor—Analytical Chemistry: Colorimetric method is sensitive and selective", Chemical & Engineering News, pp. 15, May 7, 2007.

Vannela, R. et al., "In vitro selection of Hg (II) and as (V)-dependent RNA-cleaving DNAzymes", Environmental Engineering Science, vol. 24, No. 1, pp. 73-84, (2007).

Vaughan, A.A. et al., "Optical fibre reflectance sensors for the detection of heavy metal ions based on immobilized Br-PADAP", Snesors and Actuators B, vol. 51, pp. 368-376, (1998).

Virta, M. et al., "A luminescence-based mercury biosensor", Analytical Chemistry, vol. 67, No. 3, pp. 667-669, (1995).

Wang, J. et al., "Detecting $Hg^{2+}$ ions with an ICT fluorescent sensor molecule: Remarkable emission spectra shift and unique selectivity", Journal of Organic Chemistry, vol. 71, pp. 4308-4311, (2006).

Wang, J. et al., "A series of polyamide receptor based PET fluorescent sensor molecules: Positively cooperative $Hg^{2+}$ ion binding with high sensitivity", Organic Letters, vol. 8, No. 17, pp. 3721-3724, (2006).

Widmann, A. et al., "Mercury detection in seawater using a mercaptoacetic acid modified gold microwire electrode", Electroanalysis, vol. 17, No. 10, pp. 825-831, (2005).

Xiao, Y. et al., "Electrochemical detection of parts-per-billion lead via an electrode-bound DNAzyme assembly", Journal of the American Chemical Society, vol. 129, pp. 262-263, (2007).

Yang, W. et al., "Solid phase extraction and spectrophotometric determination of mercury in tobacco and tobacco additives with 5-(p-aminobenzylidene)-thiothiorhodanine", Journal of the Brazilian Chemical Society, vol. 17, No. 5, pp. 1039-1044, (2006).

Yang, Y-K. et al., "A rhodamine-based fluorescent and colorimetric chemodosimeter for the rapid detection of Hg2+ ions in aqueous media", Journal of the American Chemical Society, vol. 127, pp. 16760-16761, (2005).

Zhang, X-B. et al "An optical fiber chemical sensor for mercury ions based on a porphyrin dimmer", Analytical Chemistry, vol. 74, No. 4, pp. 821-825, (2002).

Zhao, Y. et al., "A "turn-on" fluorescent sensor for selective Hg(II) detection in aqueous media based on metal-induced dye formation", Inorganic Chemistry, vol. 45, No. 25, pp. 10013-10015, (2006).

Zhao, Y. et al., "Tuning the sensitivity of a foldamer-based mercury sensor by its folding energy", Journal of the American Chemical Society, vol. 128, No. 31, pp. 9988-9989, (2006).

Zhao, Y. et al., "Detection of Hg2+ in aqueous solutions with a foldamer-based fluorescent sensor modulated by surgactant micelles", Organic Letters, vol. 8, No. 21, pp. 4715-4717, (2006).

Zuker, M., "Mfold web server for nucleic acid folding and hybridization prediction", Nucleic Acids Research, vol. 31, No. 13, pp. 3406-3415, (2003).

International Search Report dated May 10, 2007 for PCT application No. PCT/US2006/030617.

Liu, J. et al., "Adenosine-dependent assembly of aptazyme-functionalized gold nanoparticles and its application as a colorimetric biosensor", Analytical Chemistry, vol. 76, No. 6, pp. 1627-1632, (2004).

Liu, J. et al., "Smart nanomaterials responsive to multiple chemical stimuli with controllable cooperativity", Advanced Materials, vol. 18, No. 13, pp. 1667-1671, (2006).

Nutiu, R. et al., "Signaling aptamers for monitoring enzymatic activity and for inhibitor screening", Chembiochem—A European Journal of Chemical Biology, vol. 5, No. 8, pp. 1139-1144, (2004).

Nutiu, R. et al., "Structure-switching signaling aptamers: Transducing molecular recognition into fluorescence signaling", Chemistry—A European Journal, vol. 10, No. 8, pp. 1868-1876, (2004).

International Search Report dated Jul. 31, 2007 for PCT application No. PCT/US2007/064055.

Ahern, H., "Biochemical, reagent kits offer scientists good return on investment", The Scientist, vol. 9, No. 15, pp. 20-22, (1995).

Homann, M. et al., "Dissociation of long-chain duplex RNA can occur via strand displacement in vitro: biological implication", Nucleic Acids Research, vol. 24, no. 22, pp. 4395-4400, (1996).

Alivisatos, A.P. et al., "Quantum dots as cellular probes", Annual Review Biomed. Eng, vol. 7, pp. 55-76, (2005).

Dyadyusha, L. et al., "Quenching of CdSe quantum dot emission, a new approach for biosensing", Chemical Communication, pp. 3201-3203, (2005).

Ellington, A.D. et al., "In vitro selection of RNA molecules that bind specific ligands", Nature, vol. 346, pp. 818-822, (1990).

Gerion, D. et al., "Room-temperature single-nucleotide polymorphism and multiallele DNA detection using fluorescent nanocrystals and microarrays", Analytical Chemistry, vol. 75, No. 18, pp. 4766-4772, (2003).

Goldman, E.R. et al., "Multiplexed toxin analysis using four colors of quantum dot fluororeagents", Analytical Chemistry, vol. 76, No. 3, pp. 684-688, (2004).

Gueroui, Z. et al., "Single-molecule measurements of gold-quenched quantum dots", Physical Review Letters, vol. 93, No. 16, pp. 166108/1-166108/4, (2004).

Han, M. et al., "Quantum-dot-tagged microbeads for multiplexed optical coding of biomolecules", Nature Biotechnology, vol. 19, pp. 631-635, (2001).

Hansen, J.A. et al., "Quantum-dot/Aptamer-based ultrasensitive multi-analyte electrochemical biosensor", Journal of the American Chemical Society, vol. 128, No. 7, pp. 2228-2229, (2006).

Hartig, J.S. et al., "Protein-dependent ribozymes report molecular interactions in real time", Nature Biotechnology, vol. 20, pp. 717-722, (2002).

Herman, T. et al., "Adaptive recognition by nucleic acid aptamers", Science, vol. 287, pp. 820-825, (2000).

Kurreck, J., "Antisense technologies Improvement through novel chemical modifications", Eur. J. Biochem, vol. 270, pp. 1628-1644, (2003).

Lee, J.F. et al., "Aptamer database", Nucleic Acids Research, vol. 32, Database Issue, pp. D95-D100, (2004).

Levy, M. et al., "Quantum-dot aptamer beacons for the detection of proteins", ChemBioChem, vol. 6, pp. 2163-2166, (2005).

Liu, J. et al., "Smart nanomaterials responsive to multiple chemical stimuli with controllable cooperativity", Advanced Materials, vol. 18, pp. 1667-1671, (2006).

Liu, J. et al., "Preparation of aptamer-linked gold nanoparticle purple aggregates for colorimetric sensing of analytes", Nature Protocols, vol. 1, No. 1, pp. 246-252, (2006).

Medintz, I.L. et al., "Quantum dot bioconjugates for imaging, labeling and sensing", Nature Materials, vol. 4, pp. 435-446, (2005).

Miduturu, C. V. et al., "Modulation of DNA constraints that control macromolecular folding", Angew. Chem. Int. Ed., vol. 45, pp. 1918-1921, (2006).

Mitchell, G.P. et al., "Programmed assembly of DNA functionalized quantum dots", Journal of the American Chemical Society, vol. 121, no. 35, pp. 8122-8123, (1999).

Nutiu, R. et al., "Structure-switching signaling aptamers: Transducing molecular recognition into fluorescence signaling", Chem. Eur. J., vol. 10, pp. 1868-1876, (2004).

Oh, E. et al., "Inhibition assay of biomolecules based on fluorescence resonance energy transfer (FRET) between quantum dots and gold nanoparticles", Journal of the American Chemical Society, vol. 127, No. 10, pp. 3270-3271, (2005).

Rajendran, M. et al., "In vitro selection of molecular beacons", Nucleic Acids Research, vol. 31, No. 19, pp. 5700-5713, (2003).

Vet, J.A.M. et al., "Multiplex detection of four pathogenic retroviruses using molecular beacons", Proceedings of the National Academy of Science, USA., vol. 96, pp. 6394-6399, (1999).

Wargnier, R. et al., "Energy transfer in aqueous solutions of oppositely charged CdSe/ZnS core/shell quantum dot-nanogold assemblies", Nano Letters, vol. 4, No. 3, pp. 451-457, (2004).

Wilson, R. et al., "Encoded microcarriers for high-throughput multiplexed detection", Angewandte Chemie International Edition, vol. 45, pp. 6104-6117, (2006).

Winkler, W.C. et al., "Regulation of bacterial gene expression by riboswitches", The Annual Review of Microbiology, vol. 59, pp. 487-517, (2005).

Yang, C.J. et al., "Light-switching excimer probes for rapid protein monitoring in complex biological fluids", PNAS, vol. 102, No. 48, pp. 17278-17283, (2005).

Liu, J. et al., "Quantum dot encoding of aptamer-linked nanostructures for one-pot simultaneous detection of multiple analytes", Analytical Chemistry, vol. 79, No. 11, pp. 4120-4125, (2007).

Lu, Y. et al., "Smart nanomaterials inspired by biology: Dynamic assembly of error-free nanomaterials in response to multiple chemical and biological stimuli", Accounts of Chemical Research, vol. 40, No. 5, pp. 315-323, (2007).

Allen, M.J. et al., "Magnetic resonance contrast agents for medical and molecular imaging", Met. Ions Biol. Syst., vol. 42, pp. 1-38, (2004).

Artemov, D. et al., "MR molecular imaging of the Her-2/neu receptor in breast cancer cells using targeted iron oxide nanoparticles", Magnetic Resonance in Medicine, vol. 49, pp. 403-408, (2003).

Buerger, C. et al., "Sequence-specific peptide aptamers, interacting with the intracellular domain of the epidermal growth factor receptor, interfere with stat3 activation and inhibit the growth of tumor cells", The Journal of Biological Chemistry, vol. 278, No. 39, pp. 37610-37621, (2003).

Buerger, C. et al., "Bifunctional recombinant proteins in cancer therapy: cell penetrating peptide aptamers as inhibitors of growth factor signaling", J. Cancer Research Clin. Oncol., vol. 129, pp. 669-675, (2003).

Carr, D.H. et al., "Gadolinium-DTPA as a contrast agent in MRI: initial clinical experience in 20 patients", American Journal of Roentfenol., vol. 143, pp. 215-224, (1984).

Chen, Y. et al., "An autonomous DNA nanomotor powered by a DNA enzyme", Angew. Chem. Int. Ed., vol. 43, pp. 3554-3557, (2004).

Corot, C. et al., "Macrophage imaging in central nervous system and in carotid atherosclerotic plaque using ultrasmall superparamagnetic iron oxide in magnetic resonance imaging", Investigative Radiology, vol. 39, No. 10, pp. 619-625, (2004).

Dodd, C.H. et al., "Normal T-cell response and in vivo magnetic resonance imaging of T cells loaded with HIV transactivator-peptide-derived superparamagnetic nanoparticles", Journal of Immunological Methods, vol. 256, pp. 89-105, (2001).

Drolet, D.W. et al., "An enzyme-linked oligonucleotide assay", Nature Biotechnology, vol. 14, pp. 1021-1025, (1996).

Enochs, W.S. et al., "Improved delineation of human brain tumors on MR images using a long-circulating, superparamagnetic iron oxide agent", Journal of Magnetic Resonance Imaging, vol. 9, pp. 228-232, (1999).

Famulok, M. et al., "Nucleic acid aptamers-from selection in vitro to applications in vivo", Accounts of Chemical research, vol. 33, No. 9, pp. 591-599, (2000).

Fang, X. et al., "Molecular aptamer for real-time oncoprotein platelet-derived growth factor monitoring by fluorescence anisotropy", Analytical Chemistry, vol. 73, No. 23, pp. 5752-5757, (2001).

Frullano, L. et al., "Synthesis and characterization of a doxorubicin-Gd(III) contrast agent conjugate: A new approach toward prodrug-procontrast complexes", Inorganic Chemistry, vol. 45, No. 21, pp. 8489-8491, (2006).

Hamaguchi, N. et al., "Aptamer beacons for the direct detection of proteins", Analytical Biochemistry, vol. 294, pp. 126-131, (2001).

Harisinghani, M.G. et al., "Noninvasive detection of clinically occult lymph-node metastases in prostate cancer", The New England Journal of Medicine, vol. 348, No. 25, pp. 2491-2499, (2003).

Hermann, T. et al., "Adaptive recognition by nucleic acid aptamers", Science, vol. 287, pp. 820-825, (2000).

Hoppe-Seyler, F. et al., "Peptide aptamers: Specific inhibitors of protein function", Current Molecular Medicine, vol. 4, pp. 529-538, (2004).

Huang, C-C. et al., "Aptamer-modified gold nanoparticles for colorimetric determination of platelet-derived growth factors and their receptors", Analytical Chemistry, vol. 77, No. 17, pp. 5735-5741, (2005).

Josephson, L. et al., "High-efficiency intracellular magnetic labeling with novel superparamagnetic-tat peptide conjugates", Bioconjugate Chem., vol. 10, No. 2, pp. 186-191, (1999).

Josephson, L. et al., "The effects of iron oxides on proton relaxivity", Magnetic Resonance Imaging, vol. 6, pp. 647-653, (1988).

Josephson, L. et al., "Magnetic nanosensors for the detection of oligonucleotide sequences", Angew. Chem. Int. Ed., vol. 40, No. 17, pp. 3204-3206, (2001).

Kabalka, G. et al., "Gadolinium-labeled liposomes: Targeted MR contrast agents for the liver and spleen", Radiology, vol. 163, pp. 255-258, (1987).

Kooi, M.E. et al., "Accumulation of ultrasmall superparamagnetic particles of iron oxide in human atherosclerotic plaques can be detected by in vivo magnetic resonance imaging", Circulation, vol. 107, pp. 2453-2458, (2003).

Kresse, M. et al., "Targeting of ultrasmall superparamagnetic iron oxide (USPIO) particles to tumor cells in vivo by using transferring receptor pathways", Magn. Reson. Med., vol. 40, pp. 236-242, (1998).

Lee, J. et al., "A steroid-conjugated contrast agent for magnetic resonance imaging of cell signaling", Journal of American Chemical Society, vol. 127, No. 38, pp. 13164-13166, (2005).

Lewin, M. et al., "Tat peptide-derivatized magnetic nanoparticles allow in vivo tracking and recovery of progenitor cells", Nature Biotechnology, vol. 18, pp. 410-414, (2000).

Li, J.J. et al., "Molecular aptamer beacons for real-time protein recognition", Biochemical and Biophysical Research Communications, vol. 292, No. 1, pp. 31-40, (2002).

Li, W-H. et al., "A calcium-sensitive magnetic resonance imaging contrast agent", Journal of the American Chemical Society, vol. 121, No. 6, pp. 1413-1414, (1999).

Lin, C.H. et al., "Structural basis of DNA folding and recognition in an AMP-DNA aptamer complex: distinct architectures but common recognition motifs for DNA and RNA aptamers complexed to AMP", Chemistry and Biology, vol. 4, pp. 817-832, (1997).

Liss, M. et al., "An aptamer-based quartz crystal protein biosensor", Analytical Chemistry, vol. 74, No. 17, pp. 4488-4495, (2002).

Liu, Y. et al., "Aptamer-directed self-assembly of protein arrays on a DNA nanostructure", Angew. Chem. Int. Ed., vol. 44, pp. 4333-4338, (2005).

Macaya, R.F. et al., "Thrombin-binding DNA aptamer forms a unimolecular quadruplex structure in solution", Proceedings of the National Academy of Science USA, vol. 90, pp. 3745-3749, (1993).

Nagel-Wolfrum, K. et al., "The interaction of specific peptide aptamers with the DNA binding domain and the dimerization domain of the transcription factor stat3 inhibits transactivation and induces apoptosis in tumor cells", Molecular Cancer Research, vol. 2, pp. 170-182, (2004).

Nitin, N. et al., "Functionalization and pepride-based delivery of magnetic nanoparticles as an intracellular MRI contrast agent", J. Biol. Inorg. Chem., vol. 9, pp. 706-712, (2004).

Nutiu, R. et al., "Engineering DNA aptamers and DNA enzymes with fluorescence-signaling properties", Pure Appl. Chem., vol. 76, Nos. 7-8, pp. 1547-1561, (2004).

Nutiu, R. et al., "Structure-switching signaling aptamers: Transducing molecular recognition into fluorescence signaling", Chem. Eur. J., vol. 10, pp. 1868-1876, (2004).

Padmanabhan, K. et al., "The structure of a-thrombin inhibited by a 15-mer single-stranded DNA aptamer", The Journal of Biological Chemistry, vol. 268, No. 24, pp. 17651-17654, (1993).

Pavlov, V. et al., "Aptamer-functionalized au nanoparticles for the amplified optical detection of thrombin", The Journal of the American Chemical Society, vol. 126, No. 38, pp. 11768-11769, (2004).

Pendergrast, P.S. et al., "Nucleic acid aptamers for target validation and therapeutic applications", Journal of Biomolecular Techniques, vol. 16, issue 3, pp. 224-234, (2005).

Perez, J.M. et al., "Use of magnetic nanoparticles as nanosensors to probe for molecular interactions", ChemBioChem, vol. 5, pp. 261-264, (2004).

Perez, J.M. et al., "Viral-induced self-assembly of magnetic nanoparticles allows the detection of viral particles in biological media", Journal of the American Chemical Society, vol. 125, No. 34, pp. 10192-10193, (2003).

Radi, A-E. et al., "Reagentless, reusable, ultrasensitive electrochemical molecular beacon aptasensor", Journal of the American Chemical Society, vol. 128, No. 1, pp. 117-124, (2006).

Saeed, M. et al., "Occlusive and reperfused myocardial infarcts: differentiation with Mn-DPDP-enhanced MR imaging", Radiology, vol. 172, pp. 59-64, (1989).

Shen, T. et al., "Monocrystalline iron oxide nanocompounds (MION): Physicochemical properties", Magn. Reson. Med., vol. 29, pp. 599-604, (1993).

Soriaga, M.P. et al., "Determination of the orientation of adsorbed molecules at solid-liquid interfaces by thin-layer electrochemistry: Aromatic compounds at platinum electrodes", Journal of the American Chemical Society, vol. 104, pp. 2735-2742, (1982).

Soriaga, M.P. et al., "Determination of the orientation of aromatic molecules adsorbed on platinum electrodes: The influence of iodide a surface-active anion", Journal of the American Chemical Society, vol. 104, pp. 2742-2747, (1982).

Soriaga, M.P. et al., "Determination of the orientation of aromatic molecules adsorbed on platinum electrodes: The effect of solute concentration", Journal of the American Chemical Society, vol. 104, pp. 3937-3945, (1982).

Sosnovik, D.E. et al., "Emerging concepts in molecular MRI", Current Opinion in Biotechnology, vol. 18, pp. 4-10, (2007).

Taboada, E. et al., "Relaxometric and magnetic characterization of ultrasmall iron oxide nanoparticles with high magnetization. Evaluation as potential $T_1$ magnetic resonance imaging contrast agents for molecular imaging", Langmuir, vol. 23, No. 8, pp. 4583-4588, (2007).

Tasset, D.M. et al., "Oligonucleotide inhibitors of human thrombin that bind distinct epitopes", J. Mol. Biol., vol. 272, pp. 688-698, (1997).

Tian, Y. et al., "DNAzyme amplification of molecular beacon signal", Talanta, vol. 67, pp. 532-537, (2005).

Tompkins, H.G. et al., "The study of the gas-solid interaction of acetic acid with a cuprous oxide surface using reflection-absorption spectroscopy", Journal of colloid and interface science, vol. 49, No. 3, pp. 410-421, (1974).

Tsourkas, A. et al., "Magnetic relaxation switch immunosensors detect enantiomeric impurities", Angew. Chem. Int. Ed., vol. 43, pp. 2395-2399, (2004).

Wang, S. et al., "Core/shell quantum dots with high relaxivity and photoluminescence for multi modality imaging", Journal of the American Chemical Society, vol. 129, No. 13, pp. 3848-3856, (2007).

Weissleder, R. et al., "MR imaging of splenic metastases: Ferrite-enhanced detection in rats", American Journal Roentgenol., vol. 149, pp. 723-726, (1987).

Xiao, Y. et al., "Label-free electronic detection of thrombin in blood serum by using an aptamer-based sensor", Angew. Chem. Int. Ed., vol. 44, pp. 5456-5459, (2005).

Xiao, Y. et al., "A reagentless signal-on architecture for electronic, aptamer-based sensors via target-induced strand displacement", Journal of the American Chemical Society, vol. 127, No. 51, pp. 17990-17991, (2005).

Xu, D. et al., "Label-free electrochemical detection for aptamer-based array electrodes", Analytical Chemistry, vol. 77, No. 16, pp. 6218-6224, (2005).

Yamamoto, R. et al., "Molecular beacon aptamer fluoresces in the presence of Tat protein of HIV-1", Genes to Cells, vol. 5, pp. 389-396, (2000).

Zhao, M. et al., "Magnetic sensors for protease assays", Angew. Chem. Int. Ed., vol. 42, No. 12, pp. 1375-1378, (2003).

Zhao, M. et al., "Differential conjugation of tat peptide to superparamagnetic nanoparticles and its effect on cellular uptake", Bioconjugate Chem., vol. 13, pp. 840-844, (2002).

Fahlman, R.P. et al., "DNA conformational switches as sensitive electronic sensors of analytes", Journal of the American Chemical Society, vol. 124, 4610-4616, (2002).

Mayer, G. et al., "High-throughput-compatible assay for glmS riboswitch metabolite dependence", ChemBioChem, vol. 7, pp. 602-604, (2006).

Elowe, N., et al., "Small-molecule screening made simple for a difficult target with a signaling nucleic acid aptamer that reports on deaminase activity", Angew. Chem. Int. Ed., vol. 45, pp. 5648-5652, (2006).

Yigit, M. et al., "Smart "turn-on" magnetic resonance contrast agents based on aptamer-functionalized superparamagnetic iron oxide nanoparticles", ChemBioChem, vol. 8, pp. 1675-1678, (2007).

Xu, D. et al., "Label-free electrochemical detection for aptamer-based array electrodes", Analytical Chemistry, vol. 77, No. 16, pp. 5107-5113, (2005).

Yigit, M et al., "MRI detection of thrombin with aptamer functionalized superparamagnetic iron oxide nanoparticles", Bioconjugate Chem., vol. 19, pp. 412-417, (2008).

International Search Report dated Mar. 4, 2009 for PCT application No. PCT/US2008/070177.

International Search Report dated Apr. 17, 2009 for PCT application No. PCT/US2008/051185.

International Search Report dated Aug. 13, 2009 for PCT application No. PCT/US2008/072327.

Liu, J. et al., "Rational design of turn-on allosteric DNAzyme catalytic beacons for aqueous mercury ions with ultrahigh sensitivity and selectivity", Angewandte Chemmie. International Edition, vol. 46, No. 40, pp. 7587-7590, (2007).

Stadler, B. et al., "Micropatterning of DNA-tagged vesicles", Langmuir, vol. 20, No. 26, pp. 11348-11354, (2004).

Pfeiffer, I. et al., "Bivalent cholesterol-Based coupling of oligonucleotides to lipid membrane assemblies", Journal of the American Chemical Society, vol. 126, No. 33, pp. 10224-10225, (2004).

Shin, J. et al., "Acid-triggered release via dePEGylation of DOPE liposomes containing acid-labile vinyl ether PEG-lipids", Journal of Controlled Release, vol. 91, issues 1-2, pp. 187-200, (2003).

Cram, D.J. et al., "Organic Chemistry", Mcgraw-Hill, pp. 560-569, (1959).

Rusconi, C.P. et al., "Antidote-mediated control of an anticoagulant aptamer in vivo", Nature Biotechnology Letters, vol. 22, No. 11, pp. 1423-1428, (2004).

Willis M.C. et al., "Liposome-anchored vascular endothelial growth factor aptamers", Bioconjugate Chem., vol. 9, No. 5, pp. 573-582, (1998).

Healy, J.M. et al., "Pharmacokinetics and biodistribution of novel aptamer compositions", Pharm. Research, vol. 21, No. 12, pp. 2234-2246, (2004).

Farokhzad, O.C. et al., "Targeted nanoparticle-aptamer bioconjugates for cancer chemotherapy in vivo", Proceedings of the National Academy of Science, vol. 103, No. 16, pp. 6315-6320, (2006).

Farokhzad, O.C. et al., "Nanopartide-aptamer bioconjugates: A new approach for targeting prostate cancer cells", Cancer Research, vol. 64, pp. 7668-7672, (2004).

American Cancer Society Statistics for 2006. http://www.cancer.org/docroot/stt/stt_0.asp 2006.

Eifel, P. et al., "National Institutes of Health Consensus Development Panel, National Institutes of Health Consensus Development Conference statement: Adjuvant therapy for breast cancer, Nov. 1-3, 2000", Journal of the National Cancer Institute, vol. 93, No. 13, pp. 979-989, (2001).

Park, J.W. et al., "Tumor targeting using anti-her2 immunoliposomes", Journal of Controlled Release, vol. 74, pp. 95-113, (2001).

Kallab, V. et al., "HER2/EGFR internalization: a novel biomarker for ErbB-targeted therapeutics", Breast Cancer Research Treat., vol. 88, pp. S126-S127, (2004).

Wilson, K.S. et al., "Differential gene expression patterns in HER2/neu-positive and -negative breast cancer cell lines and tissues", American Journal of Pathology, vol. 161, No. 4, pp. 1171-1185, (2002).

Weigelt, B. et al., "Breast cancer metastasis: Markers and models", Nature Reviews, Cancer, vol. 5, pp. 591-602, (2005).

Pegram, M.D. et al., "Rational combinations of trastuzumab with chemotherapeutic drugs used in the treatment of breast cancer", Journal of the National Cancer Institute, vol. 96, No. 10, pp. 739-749, (2004).

Kirpotin, D.B. et al., "Antibody targeting of long-circulating lipidic nanoparticles does not increase tumor localization but does increase internalization in animal models", Cancer Research, vol. 66, No. 13, pp. 6732-6740, (2006).

Cheng, C. et al., "Formulation of Functionalized PLGA-PEG Nanoparticles for in Vivo Targeted Drug Delivery", Biomaterials, vol. 28, issue 5, pp. 869-876, (2007).

Bass, B.L. et al., "Specific interaction between the self-splicing RNA of Tetrahymena and its guanosine substrate: implications for biological catalysis by RNA", Nature, vol. 308, pp. 820-826, (1984).

Ellington, A.D. et al., "Combinatorial methods: aptamers and aptazymes", Part of the SPIE Conference on Advanced Materials and Opitical Systems for Chemical and Biological Detection, SPIE, vol. 3858, pp. 126-134, (1999).

Robertson, M.P. et al., "Aptazymes as generalized signal transducers", Nucleic Acids Symp. Ser., vol. 41, pp. 1-3, (1999).

Pagratis, N.C. et al., "Potent 2'-amino-, and 2'-fluoro-2'-deoxyribonucleotide RNA inhibitors of keratinocyte growth factor", Nature Biotechnology, vol. 15, pp. 68-73, (1997).

Lupold, S.E. et al., "Identification and characterization of nuclease-stabilized RNA molecules that bind human prostate cancer cells via the prostate-specific membrane antigen", Cancer research, vol. 62, pp. 4029-4033, (2002).

Jenison, R.D. et al., "Oligonucleotide inhibitors of P-selectin-dependent neutrophil-platelet adhesion", Antisense Nucleic Acid Drug Dev., vol. 8, pp. 265-279, (1998).

Hicke, B.J. et al., "DNA aptamers block L-selectin function in vivo. Inhibition of human lymphocyte trafficking in SCID mice", J. Clinical Invest., vol. 98, No. 12, pp. 2688-2692, (1996).

O'Connell, D. et al., "Calcium-dependent oligonucleotide antagonists specific for L-selectin", Proceedings of the National Academy of Science, U.S.A., vol. 93, pp. 5883-5887, (1996).

Soukup, G.A. et al., "Design of allosteric hammerhead ribozymes activated by ligand-induced structure stabilization", Structure, vol. 7, pp. 783-791, (1999).

Straubinger, R.M. et al., "Preparation and characterization of taxane-containing liposomes", Methods in Enzymology, vol. 391, pp. 97-117, (2005).

Rivera, E. "Liposomal anthracyclines in metastatic breast cancer: Clinical update", The Oncologist, vol. 8, supplement 2, pp. 3-9, (2003).

Kornblith, P. et al., "Breast cancer—Response rates to chemotherapeutic agents studied in vitro", Anticancer Research, vol. 23, pp. 3405-3411, (2003).

Pei, J. et al., "Combination with liposome-entrapped, ends-modified raf antisense oligonucleotide (LErafAON) improves the anti-tumor efficacies of cisplatin, epirubicin, mitoxantrone, docetaxel and gemcitabine", Anti-Cancer Drugs, vol. 15, pp. 243-253, (2004).

Allen, T.M. et al., "Therapeutic opportunities for targeted liposomal drug delivery", Advanced Drug Delivery Reviews, vol. 21, pp. 117-133, (1996).

Hofheinz, R.D. et al., "Liposomal encapsulated anti-cancer drugs", Anti-Cancer Drugs, vol. 16, pp. 691-707, (2005).

Schluep, T. et al., "Preclinical efficacy of the camptothecin-polymer conjugate IT-101 in multiple cancer models", Clinical Cancer Research, vol. 12, No. 5, pp. 1606-1614, (2006).

Schluep, T. et al., "Pharmacokinetics and biodistribution of the camptothecin-polymer conjugate IT-101 in rats and tumor-bearing mice", Cancer Chemoth. Pharm., vol. 57, pp. 654-662, (2006).

Cheng, J. et al., "Antitumor Activity of beta-Cyclodextrin Polymer-Camptothecin Conjugates", Molecular Pharmaceutics, vol. 1, No. 3, pp. 183-193, (2004).

Cheng, J. et al., "Synthesis of linear, beta-cyclodextrin-based polymers and their camptothecin conjugates", Bioconjugate Chem., vol. 14, pp. 1007-1017, (2003).

Guo, X. et al., "Steric stabilization of fusogenic liposomes by a low-pH sensitive PEG-diortho ester-lipid conjugate", Bioconjugate Chem., vol. 12, pp. 291-300, (2001).

Gerasimov, O.V. et al., "Cytosolic drug delivery using pH- and light-sensitive liposomes", Advanced Drug Delivery Reviews., vol. 38, pp. 317-338, (1999).

Rovira-Bru, M. et al., "Size and structure of spontaneously forming liposomes in lipid/PEG-lipid mixtures", Biophysical Journal, vol. 83, pp. 2419-2439, (2002).

Liu, J. et al., "Proofreading and error removal in a nanomaterial assembly", Angewandte Chemie, International Edition, vol. 44, pp. 7290-7293, (2005).

Liu, J. et al., "Design of asymmetric DNAzymes for dynamic control of nanoparticle aggregation states in response to chemical stimuli", Organic & Biomolecular Chemistry, vol. 4, pp. 3435-3441, (2006).

Cho, H.S. et al., "Structure of the extracellular region of HER2 alone and in complex with the Herceptin Fab", Nature, vol. 421, pp. 756-760, (2003).

Leahy, D.J. et al., "A Mammalian Expression Vector for Expression and Purification of Secreted Proteins for Structural Studies", Protein Expression and Purification, vol. 20, pp. 500-506, (2000).

Bartel, D.P. et al., "Isolation of new ribozymes from a large pool of random sequences", Science, vol. 261, pp. 1411-1418, (1993).

Jellinek, D. et al., "Inhibition of receptor binding by high-affinity RNA ligands to vascular endothelial growth factor", Biochemistry, vol. 33, pp. 10450-10456, (1994).

Jellinek, D. et al., "Potent 2'-Amino-2'-deoxypyrimidine RNA Inhibitors of Basic Fibroblast Growth Factor", Biochemistry, vol. 34, pp. 11363-11372, (1995).

Green, L.S. et al., "Inhibitory DNA Ligands to Platelet-Derived Growth Factor B-Chain", Biochemistry, vol. 35, pp. 14413-14424, (1996).

Lee, T.C. et al., "Overexpression of RRE-derived sequences inhibits HIV-1 replication in CEM cells", New Biologist, vol. 4, p. 66, (1992).

Lupold, S.E. et al., "Identification and characterization of nuclease-stabilized RNA molecules that bind human prostate cancer cells via the prostate-specific membrane antigen", Cancer Research, vol. 62, pp. 4029-4033, (2002).

Andresen, T.L. et al., "Advanced strategies in liposomal cancer therapy: Problems and prospects of active and tumor specific drug release", Progress in Lipid Research, vol. 44, pp. 68-97, (2005).

Woodle, M.C. et al., "Sterically Stabilized Liposomes—Reduction in electrophoretic mobility but not electrostatic surface potential", Biophysical Journal, vol. 61, pp. 902-910, (1992).

Zalipsky, S. et al., "Long Circulating, Cationic Liposomes Containing Amino-Peg-Phosphatidylethanolamine", FEBS Letters, vol. 353, pp. 71-74, (1994).

Morrison, W., "A fast, simple and reliable method for the microdetermination of phosphorus in biological materials", Analytical Biochemistry, vol. 7, issue 2, pp. 218-224, (1964).

Kirpotin, D. et al., "Sterically Stabilized Anti-HER2 Immunoliposomes: Design and Targeting to Human Breast Cancer Cells in Vitro", Biochemistry, vol. 36, pp. 66-75, (1997).

Klibanov, A.L. et al., "Activity of Amphipathic Poly(Ethylene Glycol)-5000 to Prolong the Circulation Time of Liposomes Depends on the Liposome Size and Is Unfavorable for Immunoliposome Binding to Target", Biochim. Biophys. Acta, vol. 1062, pp. 142-148, (1991).

Park, J.W. et al., "Development of Anti-P185$^{HER2}$ Immunoliposomes for Cancer-Therapy", Proceedings of the National Academy of Sciences U.S.A., vol. 92, pp. 1327-1331, (1995).

Zalipsky, S. "Synthesis of an End-Group Functionalized Polyethylene Glycol-Lipid Conjugate for Preparation of Polymer-Grafted Liposomes", Bioconjugate Chem., vol. 4, pp. 296-299, (1993).

Allen, T.M. et al., "A New Strategy for Attachment of Antibodies to Sterically Stabilized Liposomes Resulting in Efficient Targeting to Cancer-Cells", Biochimica et Biophysica Acta, vol. 1237, pp. 99-108, (1995).

Gillies, E.R. et al., "A new approach towards acid sensitive copolymer micelles for drug delivery", Chemical Communications, Issue 14, pp. 1640-1641, (2003).

Joensuu, O.I., "Fossil Fuels as a Source of Mercury Pollution", Science, vol. 172, No. 3987, pp. 1027-1028, (1971).

Malm, O., "Gold mining as a source of mercury exposure in the Brazilian Amazon", Environmental Research, vol. 77, No. 2, pp. 73-78, (1998).

Tchounwou, P.B. et al., "Environmental exposure to mercury and its toxicopathologic implications for public health", Environmental Toxicology, vol. 18, No. 3, pp. 149-175, (2003).

Yoon, S. et al., "A bright and specific fluorescent sensor for mercury in water, cells, and tissue", Angewandte Chemie International Edition, vol. 46, No. 35, pp. 6658-6661, (2007).

Liu, X.F. et al., "Optical detection of mercury(II) in aqueous solutions by using conjugated polymers and label-free oligonucleotides", Advanced Materials, vol. 19, No. 11, p. 1471, (2007).

Chiang, C.K. et al., "Oligonucleotide-based fluorescence probe for sensitive and selective detection of mercury (II) in aqueous solution", Analytical Chemistry, vol. 80, No. 10, pp. 3716-3721, (2008).

Yamini, Y. et al., "Solid phase extraction and determination of ultra trace amounts of mercury(II) using octadecyl silica membrane disks modified by hexathia-18-crown-6-tetraone and cold vapour atomic absorption spectrometry", Analytica Chimica Acta, vol. 355, issue 1, pp. 69-74, (1997).

Darbha, G.K. et al., "Gold nanoparticle-based miniaturized nanomaterial surface energy transfer probe for rapid and ultrasensitive detection of mercury in soil, water, and fish", Acs Nano, vol. 1, No. 3, pp. 208-214, (2007).

Li, D. et al., "Optical analysis of Hg2+ ions by oligonucleotide-gold-nanoparticle hybrids and DNA-based machines", Angewandte Chemie International Edition, vol. 47, No. 21, pp. 3927-3931, (2008).

Liu, C.W. et al., "Detection of mercury(II) based on Hg2+ -DNA complexes inducing the aggregation of gold nanoparticles", Chemical Communications, vol. 19, pp. 2242-2244, (2008).

Xue, X. et al., "One-step, room temperature, colorimetric detection of mercury (Hg2+) using DNA/nanoparticle conjugates", Journal of the American Chemical Society, vol. 130, No. 11, pp. 3244-3245, (2008).

Wang, L. et al., "Gold nanoparticle-based optical probes for target-responsive DNA structures", Gold Bulletin, vol. 41, No. 1, pp. 37-41, (2008).

Clarkson, T.W. et al., "Mercury—Major Issues in Environmental-Health", Environmental Health Perspectives, vol. 100, pp. 31-38, (1993).

Wren, C.D. "A Review of Metal Accumulation and Toxicity in Wild Mammals, 1 Mercury", Environmental Research, vol. 40, No. 1, pp. 210-244, (1986).

Koos, B.J. et al., "Mercury Toxicity in Pregnant Woman, Fetus, and Newborn-Infant -Review", American Journal of Obstetrics and Gynecology, vol. 126, No. 3, pp. 390-409, (1976).

Yu, Y. et al., "p-dimethylaminobenzaldehyde thiosemicarbazone: A simple novel selective and sensitive fluorescent sensor for mercury(II) in aqueous solution", Talanta, vol. 69, No. 1, pp. 103-106, (2006).

Braman, R.S., "Membrane Probe—Spectral Emission Type Detection System for Mercury in Water", Analytical Chemistry, vol. 43, No. 11, pp. 1462-1467, (1971).

Wernette, D.P. et al., "Surface immobilization of catalytic beacons based on ratiometric fluorescent DNAzyme sensors: a systematic study", Langmuir, vol. 23, No. 18, pp. 9513-9521, (2007).

Wang, Z. et al., "Highly sensitive "turn-on" fluorescent sensor for Hg2+ in aqueous solution based on structure-switching DNA", Chemical Communications, pp. 6005-6007, (2008).

Lu, Y. "New catalytic DNA fluorescent and colorimetric sensors for on-sit and real-time monitoring of industrial and drinking water", ISTC Reports, Illinois Sustainable Technology Center Institute of Natural Resource Sustainability, University of Illinois at Urbana-Champaign, http://www.istc.illinois.edu/info/library_docs/RR/RR-114.pdf, pp. i-ix, and 1-30, (2009).

Turner, A. P. F., "Biochemistry: Biosensors—Sense and Sensitivity", Science, vol. 290, No. 5495, pp. 1315-1317, (2000).

Abbasi, S. A., "Atomic absorption spectrometric and spectrophotometric trace analysis of uranium in environmental samples with n-p-methoxyphenyl-2-4-(2-pyridylazo) resorcinol", Int. J. Environ. Anal. Chem., vol. 36, pp. 163-172, (1989).

Arnez, J. G. et al., "Crystal structure of unmodified tRNA$^{Gln}$ complexed with glutaminyl-tRNA synthetase and ATP suggests a possible role for pseudo-uridines in stabilization of RNA structure", Biochemistry, vol. 33, pp. 7560-7567, (1994).

Blake, R. C., II, et al., "Novel monoclonal antibodies with specificity for chelated uranium (VI): isolation and binding properties", Bioconjug. Chem., vol. 15, pp. 1125-1136, (2004).

Boomer, D. W., et al, "Determination of uranium in environmental samples using inductively coupled plasma mass spectrometry", Anal. Chem., vol. 59, pp. 2810-2813, (1987).

Breaker, R. R., "Natural and engineered nucleic acids as tools to explore biology", Nature, vol. 432, pp. 838-845, (2004).

Brina, R. et al., "Direct detection of trace levels of uranium by laser-induced kinetic phosphorimetry", Anal. Chem., vol. 64, pp. 1413-1418, (1992).

Chung N. et al., "Selective extraction of gold(III) in the presences of Pd(II) and Pt(IV) by saltin-out of the mixture of 2-propanol and water", Talanta, vol. 58, pp. 927-933, (2002).

Craft, E. et al., "Depleted and natural uranium: chemistry and toxicological effects", J. Toxicol. Environ. Health, Part B, vol. 7, pp. 297-317, (2004).

Demers, L. M. et al., "Thermal desorption behavior and binding properties of DNA bases and nucleosides on gold", J. Am. Chem. Soc. vol. 124, pp. 11248-11249, (2002).

Frankforter G. et al., "Equilibria in the systems of the higher alcohols, water and salts", J. Am. Chem. Soc., vol. 37, pp. 2697-2716 (1915).

Frankforter G., et al., "Equilibria in the systems, water, acetone and inorganic salts", J. Am. Chem. Soc., vol. 36, pp. 1103-1134, (1914).

Frankforter G., et al., "Equilibria in systems containing alcohols, salts and water, including a new method of alcohol analysis", J. Phys. Chem., vol. 17, pp. 402-473, (1913).

Ginnings, P. et al., "Ternary systems: water, tertiary butanol and salts at 30° C.", J. Am. Chem. Soc., vol. 52, pp. 2282-2286, (1930).

Gongalsky, K., "Impact of pollution caused by uranium production on soil macrofauna", Environ. Monit. Assess., vol. 89, pp. 197-219, (2003).

Homola, J. et al., "Surface Plasmon Resonance (SPR) Sensors", Springer Series on Chemical Sensors and Biosensors, vol. 4, pp. 45-67, (2006).

US EPA, "Drinking water contaminants", found at http://www.epa.gov/safewater/contaminants/index.html, pp. 1-17, printed on Nov. 23, 2009.

Jones, L. A., et al., "Extraction of phenol and its metabolites from aqueous solution", J. Agric. Food Chem., vol. 41, pp. 735-741, (1993).

Katz, E. et al., "Integrated nanoparticle-biomolecule hybrid systems: sythesis, properties, and applications", Angew. Chem. Int. Ed., vol. 43, pp. 6042-6108, (2004).

Kobe, K. A. et al., "The ternary systems ethylene glycol-potassium carbonate-water and dioxane-potassium carbonate-water", J. Phys. Chem., vol. 446, pp. 629-633, (1940).

Laromaine, A. et al., "Protease-triggered dispersion of nanoparticle assemblies", J. Am. Chem. Soc., vol. 129, pp. 4156-4157, (2007).

Lazarova, Z. et al., "Solvent extraction of lactic acid from aqueous solution", Journal of Biotechnology, vol. 32, pp. 75-82, (1994).

Lee, J. H. et al., "Site-specific control of distances between gold nanoparticles using phosphorothioate anchors on DNA and a short bifunctional molecular fastener", Angew. Chem. Int. Ed., vol. 46, pp. 9006-9010, (2007).

Leggett, D. C. et al., "Salting-out solvent extraction for preconcentration of neutral polar organic solutes from water", Anal. Chem., vol. 62, pp. 1355-1356, (1990).

Leinonen, H., "Stress corrosion cracking and life prediction evaluation of austenitic stainless steels in calcium chloride solution", Corrosion Science, vol. 52, No. 5, pp. 337-346, (1996).

Li, D. et al., "Amplified electrochemical detection of DNA through the aggregation of Au nanoparticles on elctrodes and the incorporation of methylene blue into the DNA-crosslinked structure", Chem. Comm., pp. 3544-3546, (2007).

Li, H. et al., "Detection of specific sequences in rna using differential adsorption of single-stranded oligonucleotides on gold nanoparticles", Anal. Chem., vol. 77 No. 19, pp. 6229-6233, (2005).

Li, H. et al., "Colorimetric detection of dna sequences based on electrostatic interactions with unmodified gold nanoparticles", Proc. Natl. Acad. Sci. U.S.A., vol. 101, pp. 14036-14039, (2004).

Li, H. et al., "Label-free colorimetric detection of specific sequences in genomic dna amplified by the polymerase chain reaction", J. Am. Chem. Soc., vol. 126, pp. 10958-10961, (2004).

Likidis, Z. et al., "Recovery of penicillin G from fermentation broth with reactive extraction in a mixer-settler", Biotechnology Letters, vol. 9, No. 4, pp. 229-232, (1987).

Lim, I. et al., "Homocysteine-mediated reactivity and assembly of gold nanoparticles", Langmuir, vol. 23, pp. 826-833, (2007).

Lu, Y. et al., "Functional DNA nanotechnology:emerging applications of DNAzymes and aptamers", Curr. Opion. Biotech., vol. 17, pp. 580-588, (2006).

Long, F. A., et al., "Activity coefficients of nonelectrolyte solutes in aqueous salt solutions", Chem. Rev., vol. 51, pp. 119-169, (1952).

Lu, X. et al., "Salting-out separation and liquid-liquid equilibrium of tertiary butanol aqueous solution", Chemical Engineering Journal, vol. 78, pp. 165-171, (2000).

Lu, Y. et al., "Smart nanomaterials inspired by biology: dynamic assembly of error-free nanomaterials in response to multiple chemical and biological stimuli", Accounts of Chemical Research, vol. 40, pp. 315-323, (2007).

Mlakar, M. et al., "Stripping voltammetric determination of trace levels of uranium by synergic adsorptions", Analytica Chimica Acta, vol. 221, pp. 279-287, (1989).

Nishihama, S., "Review of advanced liquid-liquid extraction systems for the separation of metal ions by a combination of conversion of the metal species with chemical reaction", Ind. Eng. Chem. Res., vol. 40, pp. 3085-3091, (2001).

Pierotti, R. A., "A scaled particle theory of aqueous and nonaqueous solutions", Chemical Reviews, vol. 76, No. 6, pp. 717-726, (1976).

Centers for Disease Control, "Preventing lead poisoning in young children", U.S. Department of Health and Human Services, Public Health Service, Centers for Disease Control: Atlanta, GA, (1991).

Public Law 102-550; Residential Lead-Based Paint Hazard Reduction Act of the housing and Community Development Act of 1992; 28 pages, (1992).

Qiang, Z. et al., "Potentiometric determination of acid dissociation constants ($pK_a$) for human and veterinary antibiotics", Water Research, vol. 38, pp. 2874-2890, (2004).

Rohwer, H. et al., "Interactions of uranium and thorium with arsenazo III in an aqueous medium", Analytica Chimica Acta, vol. 341, pp. 263-268, (1997).

Safavi, A. et al., "A novel optical sensor for uranium determination", Analytica Chimica Acta vol. 530, pp. 55-60, (2005).

Sato, K. et al., "Rapid aggregation of gold nanoparticles induced by non-cross-linking DNA hybridization", J. Am. Chem. Soc., vol. 125, pp. 8102-8103, (2003).

Schenk, F. J. et. al., "Comparison of magnesium sulfate and sodium sulfate for removal of water from pesticide extracts of foods", J. AOAC International, vol. 85, No. 5, pp. 1177-1180, (2002).

Sessler, J. L. et al., "Hexaphyrin (1.0.1.0.0.0). a new colorimetric actinide sensor", Tetrahedron, vol. 60, pp. 11089-11097, (2004).

Shafer-Peltier, K. E. et al., "Toward a glucose biosensor based on surface-enhanced raman scattering", J. Am. Chem. Soc., vol. 125, pp. 588-593, (2003).

Sharma, J. et al., "DNA-templated self-assembly of two-dimensional and periodical gold nanoparticle arrays", Angew. Chem. Int. Ed., vol. 45, pp. 730-735, (2006).

Si, S. et al., "pH-controlled reversible assembly of peptide-functionalized gold nanoparticles", Langmuir, vol. 23, pp. 190-195, (2007).

Simard, J. et al., "Formation and pH-controlled assembly of amphiphilic gold nanoparticles", Chemical Commun., pp. 1943-1944, (2000).

Singleton, V. L., "An extraction technique for recovery of flavors, pigments, and other constituents from wines and other aqueous solutions", Am. J. Enol. Vitic., vol. 12, pp. 1-8, (1961).

Rao, C.V.S.R. et al., "Extraction of acetonitrile from aqueous solutions. 1. Ternary liquid equilibria", Journal of Chemical and Engineering Data, vol. 23, No. 1, pp. 23-25, (1978).

Rao, D.S. et al., "Extraction of acetonitrile from aqueous solutions. 2. ternary liquid equilibria", Journal of Chemical and Engineering Data, vol. 24, No. 3, pp. 241-244, (1979).

Tabata, M. et al., "Ion-pair extraction of metalloporphyrins into acetonitrile for determination of copper(II)", Analytical Chemistry, vol. 68, No. 5, pp. 758-762, (1996).

Tabata, M. et al., "Chemical properties of water-miscible solvents separated by salting-out and their application to solvent extraction", Analytical sciences, vol. 10, pp. 383-388, (1994).

Van der Wal, Sj., "Low viscosity organic modifiers in reversed-phase HPLC", Chromatographia, vol. 20, No. 5, pp. 274-278, (1985).

Wang, J. et al., "A gold nanoparticle-based aptamer target binding readout for ATP assay", Adv. Mater., vol. 19, pp. 3943-3946, (2007).

Wang, L. et al., "Unmodified gold nanoparticles as a colorimetric probe for potassium DNA aptamers", Chem. Comm., vol. 36, 3780-3782, (2006).

Wang, Z. et al., "Label-free colorimetric detection of lead ions with a nanomolar detection limit and tunable dynamic range by using gold nanoparticles and DNAzyme", Advanced Materials, vol. 20, pp. 3263-3267. (2008).

Warren, K. W., Reduction of corrosion through improvements in desalting, Benelux Refinery Symposium, Lanaken, Belgium, 11 pages, (1995).

Wei, H. et al., "Simple and sensitive aptamer-based colorimetric sensing of protein using unmodified gold nanoparticle probes", Chem. Comm., vol. 36, pp. 3735-3737, (2007).

Wernette, D. P. et al., "Surface immobilization of catalytic beacons based on ratiometric fluorescent DNAzyme sensors: A systematic study", Langmuir, vol. 23, pp. 9513-9521, (2007).

Willner, I. et al., "Electronic aptamer-based sensors", Angew. Chem., Int. Ed., vol. 46, pp. 6408-6418, (2007).

Wu, Y. G., et al., "An extended Johnson-Furter equation to salting-out phase separation of aqueous solution of water-miscible organic solvents", Fluid Phase Equilibria, vol. 192, pp. 1-12, (2001).

Yan, H., "Nucleic acid nanotechnology", Science, vol. 306, pp. 2048-2049, (2004).

Yang, W. H. et al., "Discrete dipole approximation for calculating extinction and raman intensities for small particles with arbitrary shapes", J. Chem. Phys., vol. 103, pp. 869-875, (1995).

Deng, Z. et al., "DNA-Encoded self-assembly of gold nanoparticles into one-dimensional arrays", Angew. Chem. Int. Ed., vol. 44, pp. 3582-3585, (2005).

Zhao, W. et al., "Simple and rapid colorimetric biosensors based on DNA aptamer and noncrosslinking gold naoparticle aggregation", ChemBioChem, vol. 8, pp. 727-731, (2007).

Zhao, W. et al., "Highly stabilized nucleotide-capped small gold nanoparticles with tunable size", Advanced Materials, vol. 19, pp. 1766-1771, (2007).

Zhao, W. et al., "DNA polymerization on gold nanoparticles through rolling circle amplification: towards novel scaffolds for three-dimensional periodic nanoassemblies", Angew. Chem. Int. Ed., vol. 45, pp. 2409-2413, (2006).

Zhao, W. et al., "DNA aptamer folding on gold nanoparticles: from colloid chemistry to bionsenors", J. Am. Chem. Soc., vol. 130, (11), pp. 3610-3618, (2008).

Zhou, P. et al., "Extraction of oxidized and reduced forms of uranium from contaminated soils: effects of carbonate concentration pH", Environmental Science Technology, vol. 39, No. 12, pp. 4435-4440, (2005).

Jacoby, M., "Sensitive, selective mercury sensor nanoparticle-based colorimetric method detects part-per-billion levels of mercury", Chemical & Engineering News, pp. 1-3, May 2, 2007.

Cruz, R.P.G. et al., supplemental to "Dinucleotide junction cleavage versatility of 8-17 deoxyribozyme", Chemistry & Biology, vol. 11, pp. 57-67, (pp. 1-8) (2004).

Saleh, O. A. et al., "Direct detection of antibody-antigen binding using an on-chip artificial pore", Proceedings of the National Academy of Science, vol. 100, No. 3, pp. 820-824, 2003.

Han, C. et al., "Highly selective and sensitive colorimetric probes for $Yb^{3+}$ions based on supramolecular aggregates assembled from B-cyclodextrin-4,4'-dipyridine inclusion complex modified silver nanoparticles", Chem. Commun., pp. 3545-3547, (2009).

Aldaye, F.A., et al., "Sequential Self-Assembly of a DNA Hexagon as a Template for the Organization of Gold Nanoparticles", Angew. Chem. Int. Ed., 45, pp. 2204-2209, 2006.

Loweth, C.J. et al., "DNA-Based Assembly of Gold Nanocrystals", Angew. Chem. Int. Ed., 38, No. 12, pp. 1808-1812, 1999.

Carbone, A., et al., "Circuits and programmable self-assembling DNA structures", Proceedings of the National Academy of Sciences of the United States of America, vol. 99, No. 20, pp. 12577-12582, 2002.

Chelyapov, N., et al., "DNA Triangles and Self-Assembled Hexagonal Tilings", J. Am. Chem. Soc., 126, pp. 13924-13925, 2004.

Conway, N.E., et al., "The Covalent Attachment of Multiple Fluorophores to DNA Containing Phosphorothioate Diesters Results in Highly Sensitive Detection of Single-Stranded DNA", Bioconjugate Chem, 2, pp. 452-457, 1991.

Ding, B., et al., "Pseudohexagonal 2D DNA Crystals from Double Crossover Cohesion", J. Am. Chem. Soc., 126, pp. 10230-10231, 2004.

Endo, M., et al., "DNA Tube Structures Controlled by a Four-Way-Branched DNA Connector", Angew. Chem. Int. Ed., 44, pp. 6074-6077, 2005.

Fidanza, J.A, et al. "Site-Specific Labeling of DNA Sequences Containing Phosphorothioate Diesters", J. Am. Chem. Soc., 114, pp. 5509-5517, 1992.

Goodman, R.P., et al., "Rapid Chiral Assembly of Rigid DNA Building Blocks for Molecular Nanofabrication", Science, 310, pp. 1661-1665, 2005.

Hagleitner, C., et al., "Smart single-chip gas sensor microsystem", Nature, vol. 414, pp. 293-296, 2001.

He, Y., et al., "Sequence Symmetry as a Tool for Designing DNA Nanostructures", Angew. Chem. Int. Ed., 44, pp. 6694-6696, 2005.

Heath, J.R., et al., "A Defect-Tolerant Computer Architecture: Opportunities for Nanotechnology", Science, vol. 280, pp. 1716-1719, 1998.

Holloway, G., et al., "An Organometallic Route to Oligonucleotides Containing Phosphoroselenoate", ChemBioChem, 3, pp. 1061-1065, 2002.

Li, H., et al., "DNA-Templated Self-Assembly of Protein and Nanoparticle Linear Arrays," J. Am. Chem. Soc., 126, pp. 418-419, 2004.

Cunningham, L., et al., "Spectroscopic Evidence for Inner-Sphere Coordination of Metal Ions to the Active Site of a Hammerhead Ribozyme", J. Am. Chem. Soc., 120, pp. 4518-4519, 1998.

Luduena, R.F., et al., N,N-Bis(α-iodoacetyl)-2,2'-dithiobis(ethylamine), a Reversible Crosslinking Reagent for Protein Sulfhydryl Groups, Analytical Biochemistry, 117. pp. 76-80, 1981.

Lund, K., et al., "Self-Assembling a Molecular Pegboard", J. Am. Chem. Soc., 127, pp. 17606-17607, 2005.

Mathieu, F., et al. "Six-Helix Bundles Designed from DNA", Nano Letters, vol. 5, No. 4, pp. 661-665, 2005.

Liu, H., et al, "Approaching the Limit: Can One DNA Oligonucleotide Assemble into Large Nanostructures?", Angew. Chem., 118, pp. 1976-1979, 2006.

Fidanza, J. et al, "Introduction of Reporter Groups at Specific Sites in DNA Containing Phosphorothioate Diesters", J. Am. Chem. Soc., 111, pp. 9117-9119, 1989.

Nakao, H., et al, "Highly Ordered Assemblies of Au Nanoparticles Organized on DNA", Nano Letters, vol. 3, No. 10, pp. 1391-1394, 2003.

Patolsky, F., et al,, "Au-Nanoparticle Nanowires Based on DNA and Polylysine Templates", Angew. Chem. Int. Ed., 41, No. 13, pp. 2323-2327, 2002.

Pinto, Y., et al., "Sequence-Encoded Self-Assembly of Multiple-Nanocomponent Arrays by 2D DNA Scaffolding", Nano Letters, vol. 5, No. 12, pp. 2399-2402, 2005.

Rothemund, P., "Folding DNA to create nanoscale shapes and patterns", Nature, vol. 440, pp. 297-302, 2006.

Yang, X., et al, "Ligation of DNA Triangles Containing Double Crossover Molecules", J. Am. Chem. Soc., 120, pp. 9779-9786, 1998.

Seeman, N.C., "Nucleic Acid Nanostructures and Topology", Angew. Chem. Int. Ed., 37, pp. 3220-3238, 1998.

Seeman, N. C., "At the Crossroads of Chemistry, Biology, and Materials: Structural DNA Nanotechnology", Chemistry & Biology, vol. 10, pp. 1151-1159, 2003.

Le, J.D., et al., "DNA-Templated Self-Assembly of Metallic Nanocomponent Arrays on a Surface", Nano Letters, vol. 4, No. 12, pp. 2343-2347, 2004.

Seeman, N.C., et al. "Nucleic acid nanostructures: bottom-up control of geometry on the nanoscale", Reports on Progress in Physics, 68, pp. 237-270, 2005.

Warner, M.G., et al., "Linear assemblies of nanoparticles electrostatically organized on DNA scaffolds", Nature Materials, vol. 2, pp. 272-277, 2003.

Winfree, E., et al., "Design and self-assembly of two-dimensional DNA crystals", Nature, vol. 394, pp. 539-544, 1998.

Woehrle, G.H., et al., "Molecular-Level Control of Feature Separation in One-Dimensional Nanostructure Assemblies Formed by Biomolecular Nanolithography", Langmuir, 20, pp. 5982-5988, 2004.

Zhang, J., et al, "Periodic Square-Like Gold Nanoparticle Arrays Templated by Self-Assembled 2D DNA Nanogrids on a Surface", Nano Letters, vol. 6, No. 2, pp. 248-251, 2006.

Yang, T. et al. "Tunneling Phase Logic Cellular Nonlinear Networks", International Journal of Bifurcation and Chaos, vol. 11, No. 12, pp. 2895-2911, 2001.

Liu, Z., et al., "Imaging DNA Molecules on Mica Surface by Atomic Force Microscopy in Air and in Liquid", Microscopy Research and Technique, 66, pp. 179-185, 2005.

Niemeyer, C.M., et al., "Covalent DNA-Streptavidin Conjugates as Building Blocks for Novel Biometallic Nanostructures", Angew. Chem. Int. Ed., 37, No. 16, pp. 2265-2268, 1998.

* cited by examiner

Normal membrane    Geometrically modified membrane

LATERAL FLOW DEVICES

REFERENCE TO RELATED APPLICATIONS

This application claims the benefit of U.S. Provisional Application No. 60/782,949 entitled "Lateral Flow Devices" filed Mar. 16, 2006 and U.S. Provisional Application No. 60/821,043 entitled "Lateral Flow Devices" filed Aug. 1, 2006, which are incorporated by reference in their entirety.

FEDERALLY SPONSORED RESEARCH OR DEVELOPMENT

The subject matter of this application may have been funded in part under the following research grants and contracts: Contract Numbers DMR-0117792 and CTS-0120978 awarded by the National Science Foundation, Contract Number DEFG02-01ER63179 awarded by United States Department of Energy, and Contract Number DAAD19-03-1-0227 awarded by the Department of Defense. The U.S. Government may certain have rights in this invention.

BACKGROUND

The ability to determine the presence of an analyte in a sample is of significant benefit. For example, many metals and metal ions, such as lead, mercury, cadmium, chromium, and arsenic, pose significant health risks when present in drinking water supplies. To prevent the contamination of drinking and other water supplies, it is common to test industrial waste-streams before their release to the water treatment plant. Biological fluids, such as blood and those originating from body tissues, also may be tested for a variety of analytes to determine if the body has been exposed to harmful agents or if a disease state exists. There is also a need to test for other toxins, for example detection of trace amounts of anthrax in a variety of samples has recently emerged.

While many analyses are performed in solution, some have been adapted to lateral flow devices. Lateral flow devices may provide multiple advantages over solution methods, such as the ability to provide the reagents in a dry or nearly dry state. Lateral flow devices also may provide the user with a simple "all in one" kit, which has a long shelf life. However, conventional lateral flow devices are typically limited to detecting specific biological analytes.

Commonly available lateral flow devices include pregnancy test kits, which test for the presence of the hCG hormone. The analysis chemistry of these devices relies on a dye labeled antibody that binds to the hCG hormone, which is then trapped by a second antibody in a visualization zone. A disadvantage of this method is the need to isolate and synthesize an antibody specific to the analyte. Another conventional calorimetric lateral flow device detects a DNA analyte by hybridization with gold nanoparticles functionalized with complementary DNA (Glynou, K., et al., *Anal. Chem.*, 75, 4155-60 (2003)). A disadvantage of this method is that the analyte must be a bio-molecule capable of DNA hybridization.

SUMMARY

In a first aspect, the present invention is an analytical test for an analyte, comprising (a) a base, having a reaction area and a visualization area, (b) a capture species, on the base in the visualization area, comprising nucleic acid, and (c) analysis chemistry reagents, on the base in the reaction area. The analysis chemistry reagents comprise (i) a substrate comprising nucleic acid and a first label, and (ii) a reactor comprising nucleic acid. The analysis chemistry reagents can react with a sample comprising the analyte and water, to produce a visualization species comprising nucleic acid and the first label, and the capture species can bind the visualization species.

In a second aspect, the present invention is an analytical test for an analyte, comprising (a) a base, having a reaction area and a visualization area, (b) a capture species, on the base in the visualization area, and (c) analysis chemistry reagents, on the base in the reaction area. The analysis chemistry reagents can react with a sample comprising the analyte and water, to produce a visualization species comprising a first label, the capture species can bind the visualization species, and the visualization species does not comprise the analyte.

In a third aspect, the present invention is an analytical test for an analyte, comprising (a) a base, having a reaction area and a visualization area, (b) a capture species, on the base in the visualization area, and (c) analysis chemistry reagents, on the base in the reaction area. The analysis chemistry reagents can react with a sample comprising the analyte and water, to produce a visualization species comprising a first label, the capture species can bind the visualization species, and the capture species cannot specifically bind the analyte.

In a fourth aspect the present invention is a lateral flow device for an analytical test for an analyte, comprising (a) a base, having a reaction area and a visualization area, (b) a capture species, on the base in the visualization area, comprising nucleic acid, and (c) at least one reagent, on the base in the reaction area. The at least one reagent comprises a substrate comprising nucleic acid and a first label. The at least one reagent can react with a reactor and a sample comprising the analyte and water, to produce a visualization species comprising nucleic acid and the first label, and the capture species can bind the visualization species.

The following definitions are included to provide a clear and consistent understanding of the specification and claims.

The term "sample" is defined as a composition suspected of containing the analyte of interest that will be subjected to analysis. Typically, a sample for analysis is in liquid form, or can be converted into liquid form, and preferably the sample is an aqueous composition. A sample may be from any source, such as an industrial sample from a waste stream, or a biological sample such as blood, urine or saliva. A sample may be treated, such as by extract, dilution or filtration, or it may be a reconstituted precipitate from an industrial or biological source.

The term "analyte" is defined as one or more substances potentially present in a sample, for which the analysis tests. An analysis for an analyte determines the presence, quantity or concentration, of the analyte in the sample.

The term "analysis chemistry reagents" refers to one or more reagents, that when reacted with a sample containing an analyte, produce a visualization species. Preferably, the visualization species is produced in proportion to the amount or concentration of the analyte. Analysis chemistry reagents preferably include a reactor and a substrate. The "reactor" is at least one compound, moiety and/or material; the "substrate" is also at least one compound, moiety and/or material. When the reactor and the substrate are mixed with the analyte, they will react to produce a visualization species. As used herein, the term "produce" includes forming by chemical reaction, as well as releasing from being bound or attached to something else. Preferably, the reactor is specific for an analyte, and the substrate is specific for a reactor. Preferably, the substrate includes a label. The reactor and the substrate may be attached, for example covalently or by hydrogen bonding (hybridization).

The term "visualization species" is a compound, moiety or material that can be detected, such as a colored compound, a fluorescent compound, a magnetic material, a radioactive material, and the like. A visualization species includes a label, which is that part of the visualization species that allows for detection, for example a colored label (such as a dye or a colored particle, including semiconductor nanoparticles (quantum dots)), a fluorescent label (such as fluorescent compound), or a magnetic label (such as a magnetic particle). Preferably, the label of the visualization species originated as the label of the substrate. It is possible for the visualization species and the substrate to be the same.

The term "capture species" refers to a compound, moiety or material that will bind the visualization species. Optionally, the capture species specifically binds the visualization species. Preferably, the capture species does not substantially bind the verification species. Preferably, the capture species does not specifically bind the analyte, more preferably the capture species does substantially bind the analyte. The capture species may form part of the visualization species, for the visualization species may not be formed until after binding the capture species.

The term "verification species" means a compound, moiety or material that can be detected, such as a colored compound, a fluorescent compound, a magnetic material, a radioactive material, and the like. A verification species includes a label. The verification species is preferably different from the visualization species. Preferably, the verification species may be detected in the same manner as the visualization species.

The term "trapping species" refers to a compound, moiety or material that will bind the verification species. Optionally, the trapping species specifically binds the verification species. Preferably, the trapping species does not substantially bind the visualization species. The trapping species may form part of the verification species, for example the verification species may not be formed until after binding by the trapping species.

The term "specifically bind" means that binding between the two things is more favored binding, as compared to most other members of the same class or genus. For example, the binding between an antibody specific for an antigen, and the antigen; and hybridization between two complementary strands of DNA; are both examples of specific binding.

The term "calorimetric" is defined as an analysis where the reagent or reagents constituting the sensor system produce a color change in the presence or absence of an analyte, for example when the visualization species is colored.

The term "aptamer" refers to nucleic acid that specifically binds a target compound or moiety. The term "nucleic acid enzyme" (NAE) refers to nucleic acid that catalyses a chemical reaction (such as cleavage of a substrate) when it binds a specific cofactor (such as a divalent metal ion). Both an aptamer and a nucleic acid enzyme are examples of reactors.

The term "conformational change" refers to the process by which a nucleic acid, such as an aptamer, adopts a different secondary or tertiary structure. The term "fold" may be substituted for conformational change.

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention. In the figures, like referenced numerals designate corresponding parts throughout the different views.

DETAILED DESCRIPTION

The present invention includes lateral flow devices that include analysis chemistry reagents, which preferably include aptamers or nucleic acid enzymes, allowing for adaptation of the device to many different analytes. Unlike conventional lateral flow devices, which rely on the analyte to bind specifically to a labeled species and travel to a visualization area where the analyte (now labeled) binds specifically to a capture species, the analysis chemistry of the present invention does not require specific binding of the analyte for binding of the visualization species by the capture species. Instead, the analyte reacts with the analysis chemistry reagents to produce a visualization species. Furthermore, the analysis chemistry reagents may be applied at any time prior to use, allowing for the manufacture of a large number of lateral flow devices, which can be used to analyze for any one of a large variety of analytes; the remaining analysis chemistry reagent or reagents that are specific for the analyte of interest can be applied to the lateral flow device just prior to sale or use, or may be added to the sample by the user.

Preferred methods of activating the release of the visualization species rely on the disaggregation of an aggregate, the cleavage of a substrate by a NAE, or a conformational change of a nucleic acid. Because the analyte triggers the release of the visualization species, the visualization species does not depend on the analyte for its chemical nature, i.e. there is more than one visualization species that may be chosen, by selection of analysis chemistry reagents, for a given analyte. The lateral flow device may be designed to operate with only a single visualization species even for analyses of different analytes by changing analysis chemistry reagents; the device may be rapidly adapted to a different analyte by modifying the analysis chemistry reagents.

Figure 1A:
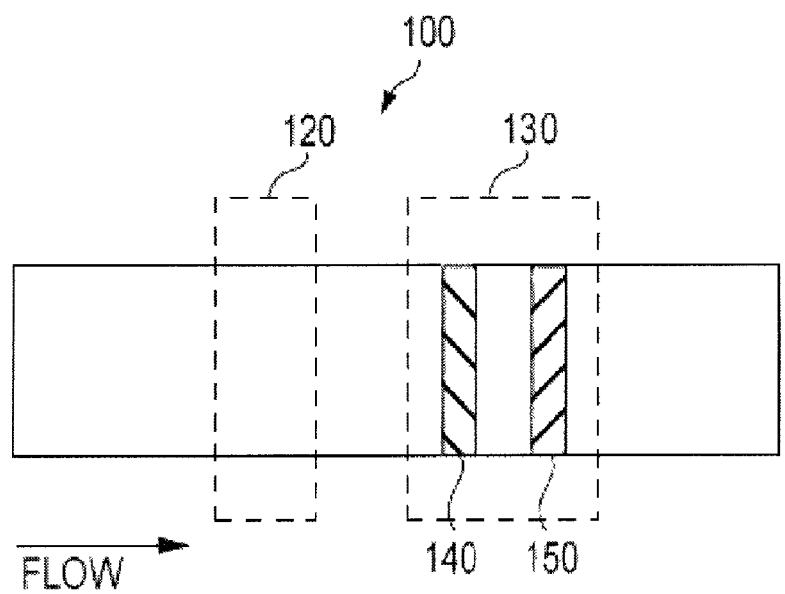
FIG. 1A represents a lateral flow device having reaction and visualization areas.
Figure 1B:
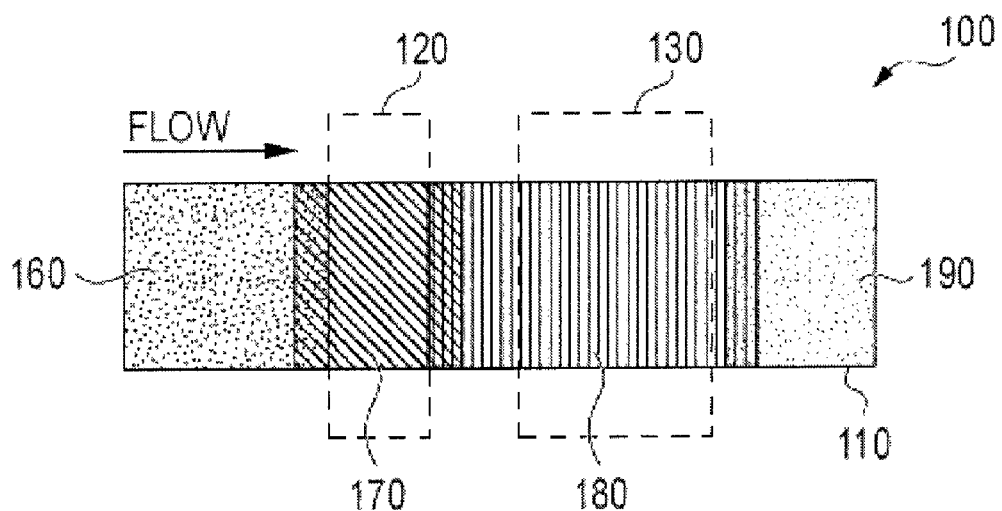
FIG. 1B represents a lateral flow device including a membrane and wicking, conjugate, and absorption pads.

FIGS. 1A-1B depict a lateral flow device 100 that includes a base 110, a reaction area 120, and a visualization area 130. The visualization area 130 may include a first visualization zone 140 and optionally a second visualization zone 150.

The base 110 may be made from any material that is compatible with the analysis chemistry and allows visualization species 135 (not shown) to travel from the reaction area 120 to the visualization area 130. As depicted in FIG. 1B, the base 110 may include a wicking pad 160, a conjugate pad 170, a membrane 180, and an absorption pad 190 on a plastic backing (not shown). In one aspect, the membrane 180 may be present under one or more of the pads.

The reaction area 120 is where the analysis chemistry occurs (a chemical reaction between the analysis chemistry reagents and any analyte in the sample), and thus may include at least a portion of the conjugate pad 170 to provide a potential attachment site for some of the analysis chemistry reagents. The visualization area 130 is where the visualization species 135 are observed to determine the results of the analysis. In one aspect, the visualization area 130 includes at least a portion of the membrane 180. The visualization area 130 may include one or more capture species that bind the visualization species 135 released from the reaction area 120 during the analysis. In a preferred aspect, the visualization area 130 includes at least two agents, a capture species and optionally a trapping species.

Figure 2:
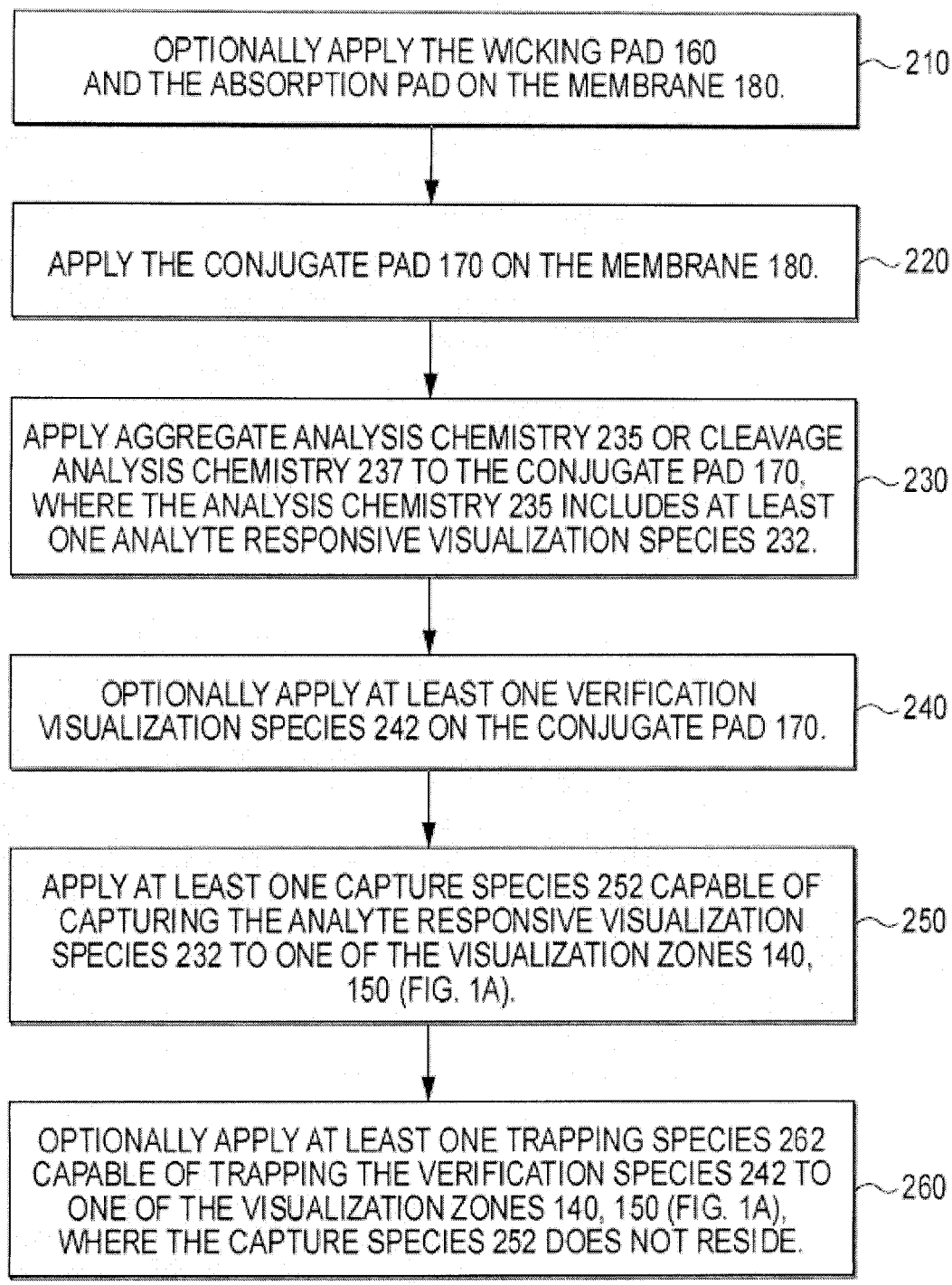
FIG. 2 represents a method of making a lateral flow device.

FIG. 2 represents a method 200 of making a lateral flow device, such as the lateral flow device 100 of FIG. 1B. In 210, the wicking pad 160 and the absorption pad 190 are optionally applied on the membrane 180. In 220, the conjugate pad 170 is applied on the membrane 180. Depending on the analysis chemistry used with the device 100, the composition of the conjugate pad 170 may be altered.

In 230, the analysis chemistry reagents 235 that react with the analyte, to form a visualization species 232, may be applied to the conjugate pad 170. Optionally, in addition to the visualization species 232, at least one verification species 242, or reagents that will form at least one verification species, may be applied on the conjugate pad 170 in 240.

The optional verification species 242 provides a species that is similar to the visualization species 232 that will travel from the reaction area 120 to the visualization area 130 of FIGS. 1A-1B, regardless of the presence of the analyte. Thus, in one aspect, if the verification species 242 is not detected in the visualization area 130 during the analysis, the analysis has failed and the result should be discarded.

In 250, preferably at least one capture species 252 is applied to one of the visualization zones 140, 150 of FIG. 1A. As depicted in FIGS. 1A-1B, the visualization zones 140, 150 may be present on the membrane 180. Thus, if the visualization species 232 includes a gold nanoparticle functionalized with DNA (a colored species), the capture species 252 may be DNA complimentary to the DNA of the nanoparticle, which would specifically bind this visualization species. Nitrocellulose may be used as the capture species, which does not specifically bind this visualization species.

In 260, preferably at least one trapping species 262 may be applied to one of the visualization zones 140, 150 (FIG. 1A), where the capture species 252 does not reside. Thus, if the first visualization zone 140 includes the trapping species 262, then the second visualization zone 150 includes the capture species 252 and vice versa. For example, if the verification species 242 includes a gold nanoparticle functionalized with DNA and biotin, the trapping species 262 may be streptavidin, which specifically binds this verification species.

Figure 3:
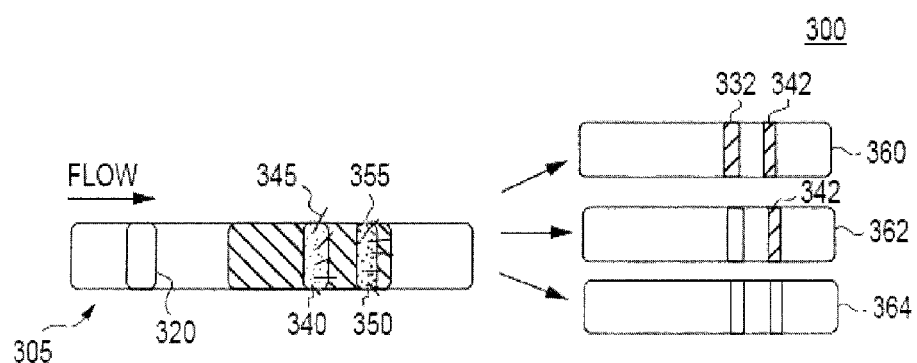
FIG. 3 represents an analysis using a lateral flow device.

FIG. 3 represents an analysis 300 for determining the presence of an analyte 302 (not shown) with a lateral flow device, such as the device 305. The lateral flow device 305 is depicted with a reaction area 320, and first and second visualization zones 340, 350, respectively. The first visualization zone 340 is prepared with second DNA as the capture species 345, while the second visualization zone 350 was treated with streptavidin 355 to serve as the trapping species.

The reaction area 320 is treated with analysis chemistry reagents that released gold nanoparticles functionalized with a first DNA complementary to a second DNA, in the presence of the analyte 302. The reaction area 320 also is treated with verification species 342 in the form of gold nanoparticles functionalized with third DNA and biotin, capable of being bound by the streptavidin 355 (the trapping species) present in the second visualization zone 350. The third DNA is not complementary to the second DNA 345 present in the first visualization zone 340.

To begin the analysis 300, a sample 301 (not shown) suspected of contain the analyte 302 is deposited on the reaction zone 320. A liquid eluent, such as water including a buffer, is then applied to the left side of the device 305. The eluent may be any liquid that does not interfere with the analysis chemistry and that has the ability to move the visualization species from the reaction area 320 to the visualization zones 340, 350. Preferably, the eluent is an aqueous solution. As the liquid travels through the reaction zone 320 and through the visualization zones 340, 350, three scenarios are possible, illustrated from the top down on the right side of FIG. 3.

Post analysis lateral flow device 364 depicts a failed test where neither the analyte responsive species 332, nor the verification species 342 reaches the visualization zones 340, 350. The failure of the verification species 342 to reach the visualization zone 350 may mean that the sample 301 was incompatible with the analysis chemistry or that the liquid eluent failed to transport the verification species 342. In either instance, the analysis failed.

Post analysis lateral flow device 362 represents the scenario when the verification species 342 is trapped by the streptavidin 355 present in the second visualization zone 350. The device 362 shows a color change in the second visualization zone 350 due to the arrival of the verification species 342. Thus, the analysis is successful, but the sample lacked the analyte required to activate the analysis chemistry.

Post analysis lateral flow device 360 represents the scenario when the visualization species 332 is hybridized by the second DNA present in the first visualization zone 340 and the verification species 342 is trapped in the second visualization zone 350. Thus, the analysis is successful and the sample included the analyte which activated the analysis chemistry to release the visualization species.

A variety of analysis chemistry, and hence analysis chemistry reagents, may be used, and may be selected based on the choice of analyte and label. For example, U.S. patent application Ser. No. 11/202,380 entitled "Aptamer-Based Colorimetric Sensor Systems" to Yi Lu et al., filed 11 Aug. 2005, describes an aptamer-based calorimetric sensor system, which produces a visualization species containing a nucleic acid attached to a nanoparticle (which serves as the label); the analysis chemistry reagents form an aggregate, containing the visualization species and the aptamer. When the analyte is present, it specifically binds to the aptamer, preventing the aptamer from binding to the visualization species, and causing the visualization species to be released from the aggregate. Since different aptamers which specifically bind different analyte may be designed which will all form an aggregate with the same visualization species, all parts of the analytical test may be the same for different analytes, as long as the analysis chemistry reagents contain an aptamer which specifically binds the analyte of interest.

Table I below lists analytes, the aptamer or aptamers that bind with and fold in response to that analyte, and the reference or references where the sequence of each aptamer is described.

TABLE I

| Analyte class | Example | Aptamer Motif Sequence (SEQ ID NO.) | Ref |
|---|---|---|---|
| Metal ions | K(I) | GGGTTAGGGTTAGGGTTAGGG<br>(SEQ ID NO. 1) | 1 |
| | Zn(II) | AGGCGAGGUGAAAUGAGCGGUAAU<br>AGCCU<br>(SEQ ID NO. 2) | 2 |
| | Ni(II) | GGGAGAGGAUACUACACGUGAUAG<br>UCAGGGAACAUGACAAACACAGGG<br>ACUUGCGAAAAUCAGUGUUUUGCC<br>AUUGCAUGUAGCAGAAGCUUCCG<br>(SEQ ID NO. 3) | 3 |
| Organic dyes | Cibacron blue | GGGAGAATTCCCGCGGCAGAAGCCC<br>ACCTGCCTTTGAACTCTATGTTATTGG<br>GTGGGGGAAACTTAAGAAAACTACC<br>ACCCTTCAACATTACCGCCCTTCAGCC<br>TGCCAGCGCCCTGCAGCCCGGGAAG<br>CTT<br>(SEQ ID NO. 4) | 4 |
| | Malachite green | GGAUCCCGACUGGCGAGAGCCAGG<br>UAACGAAUGGAUCC<br>(SEQ ID NO. 5) | 5 |
| | Sulforhodamine B | CCGGCCAAGGGUGGGAGGGAGGGG<br>GCCGG<br>(SEQ ID NO. 6) | 6 |
| Small organic molecules | Biotin | AUGGCACCGACCAUAGGCUCGGGU<br>UGCCAGAGGUUCCACACUUUCAUC<br>GAAAAGCCUAUGC<br>(SEQ ID NO. 7) | 7 |
| | Theophylline | GGCGAUACCAGCCGAAAGGCCCUU<br>GGCAGCGUC<br>(SEQ ID NO. 8) | 8 |
| | Adenine | GAUAGGACGAUUAUCGAAAAUCAC<br>CAGAUUGGACCCUGGUUAACGAUC<br>CAUU<br>(SEQ ID NO. 9) | 9 |
| | Cocaine | GGGAGACAAGGATAAATCCTTCAATG<br>AAGTGGGTCGACA<br>(SEQ ID NO. 10) | 10 |
| | Dopamine | GGGAAUUCCGCGUGUGCGCCGCG<br>GAAGAGGGAAUAUAGAGGCCAGCA<br>CAUAGUGAGGCCCUCCUCCC<br>(SEQ ID NO. 11) | 11 |
| Amino acids | Arginine | GGGAGCUCAGAAUAAACGCUCAAG<br>GAGGACCGUGCACUCCUCGAACAU<br>UUCGAGAUGAGACACGGAUCCUGC<br>(SEQ ID NO. 12) | 12 |
| | Citrulline | GACGAGAAGGAGUGCUGGUUAUAC<br>UAGCGGUUAGGUCACUCGUC<br>(SEQ ID NO. 13) | 13 |
| Nucleosides & nucleotides | ATP | ACCTGGGGGAGTATTGCGGAGGAAG<br>GT<br>(SEQ ID NO. 14) | 14 |
| | cAMP | GGAAGAGAUGGCGACUAAAACGAC | 15 |

TABLE I-continued

| Analyte class | Example | Aptamer Motif Sequence (SEQ ID NO.) | Ref |
|---|---|---|---|
| | | UUGUCGC<br>(SEQ ID NO. 15) | |
| | GTP | UCUAGCAGUUCAGGUAACCACGUA<br>AGAUACGGGUCUAGA<br>(SEQ ID NO. 16) | 16 |
| | Guanosine | GGGAGCUCAGAAUAAACGCUCAAC<br>CCGACAGAUCGGCAACGCCNUGUU<br>UUCGACANGAGACACCGAUCCUGC<br>ACCAAAGCUUCC<br>(SEQ ID NO. 17) | 17 |
| | Adenosine | ACCTGGGGGAGTATTGCGGAGGAAG<br>GT<br>(SEQ ID NO. 18) | 18 |
| RNA | TAR-RNA | GCAGTCTCGTCGACACCCAGCAGCG<br>CATGTAACTCCCATACATGTGTGCT<br>GGATCCGACGCAG<br>(SEQ ID NO. 19) | 19 |
| Biological cofactors | CoA | GGGCACGAGCGAAGGGCAUAAGCU<br>GACGAAAGUCAGACAAGACAUGGU<br>GCCC<br>(SEQ ID NO. 20) | 20 |
| | NMN | GGAACCCAACUAGGCGUUUGAGGG<br>GAUUCGGCCACGGUAACAACCCCU<br>C<br>(SEQ ID NO. 21) | 21 |
| | FAD | GGGCAUAAGGUAUUUAAUUCCAUA<br>CAAGUUUACAAGAAAGAUGCA<br>(SEQ ID NO. 22) | 22 |
| | Porphyrin | TAAACTAAATGTGGAGGGTGCGACG<br>GGAAGAAGTTTA<br>(SEQ ID NO. 23) | 23 |
| | Vitamin B12 | CCGGUGCGCAUAACCACCUCAGUG<br>CGAGCAA<br>(SEQ ID NO. 24) | 24 |
| Amino-glycosides | Tobramycin | GGGAGAAUUCCGACCAGAAGCUUU<br>GGUUGUCUUGUACGUUCACUGUU<br>ACGAUUGUGUUAGGUUUAACUACA<br>CUUUGCAAUCGCAUAUGUGCGUCU<br>ACAUGGAUCCUCA<br>(SEQ ID NO. 25) | 25 |
| Oligo-saccharides | Cellobiose | GCGGGGUUGGGCGGGUGGGUUCGC<br>TGGGCAGGGGGCGAGTG<br>(SEQ ID NO. 26) | 26 |
| Poly-saccharides | Sephadex | UACAGAAUGGGUUGGUAGGCAUAC<br>CUAAUCGAGAAUGAUA<br>(SEQ ID NO. 27) | 27 |
| Antibiotics | Viomycin | GGAGCUCAGCCUUCACUGCAAUGG<br>GCCGCUAGGUUGAUGUGCAGUGA<br>AGUCAGCUGAGGCCCAGGGCUGAA<br>AGGAUCGCCCUCCUCGACUCUGUGC<br>CACCACGGUCGGAUCCAC<br>(SEQ ID NO. 28) | 28 |
| | Streptomycin | GGAUCGCAUUUGGACUUCUGCCCA<br>GGGGGCACCACGGUCGGAUCC<br>(SEQ ID NO. 29) | 29 |
| | Tetracycline | GGCCUAAAACAUACCAGAUUUCGA<br>UCUGGACAGGUGAAGAAUUCGACC<br>ACCUAGGCCGGU<br>(SEQ ID NO. 30) | 30 |

TABLE I-continued

| Analyte class | Example | Aptamer Motif Sequence (SEQ ID NO.) | Ref |
|---|---|---|---|
| | Vasopressin | ACGTGAATGATAGACGTATGTCGAG1 31<br>TGCTGTGTGCGGATGAACGT<br>(SEQ ID NO. 31) | |
| Peptides | Substance P | GGGAGCUGAGAAUAAACGCUCAAG<br>GGCAACGCGGGCACCCCGACAGGU<br>GCAAAAACGCACCGACGCCCGGCCG<br>AAGAAGGGGAUUCGACAUGAGGCC<br>CGGAUCCGGC<br>(SEQ ID NO. 32) | 32 |
| Enzymes | HIV Rev Transcriptase | UCCGUUUUCAGUCGGGAAAAACUG<br>(SEQ ID NO. 33) | 33 |
| | Human thrombin | GGTTGGTGTGGTTGG<br>(SEQ ID NO. 34) | 34 |
| Growth factors | VEGF$_{165}$ | GCGGUAGGAAGAAUUGGAAGCGC<br>(SEQ ID NO. 35) | 35 |
| Transcription factors | NF-κB | GGGAUAUCCUCGAGACAUAAGAAA<br>CAAGAUAGAUCCUGAAACUGUUUU<br>AAGGUUGGCCGAUCUUCUGCUCGA<br>GAAUGCAUGAAGCGUUCCAUAUUU<br>UU<br>(SEQ ID NO. 36) | 36 |
| Antibodies | Human IgE | GGGGCACGTTTATCCGTCCCTCCTAG<br>TGGCGTGCCCC<br>(SEQ ID NO. 37) | 37 |
| Gene Regulatory factors | Elongation factor Tu | GGGGCUAUUGUGACUCAGCGGUU<br>CGACCCCGCUUAGCUCCACCA<br>(SEQ ID NO. 38) | 38 |
| Cell adhesion molecules | Human CD4 | UGACGUCCUUAGAAUUGCGCAUUC<br>CUCACACAGGAUCUU<br>(SEQ ID NO. 39) | 39 |
| cells | YPEN-1 endothelial | ATACCAGCTTATTCAATTAGGCGGTG<br>CATTGTGGTTGGTAGTATACATGAGC<br>TTTGGTTGAGACTAGTCGCAAGATAT<br>AGATAGTAAGTGCAATCT<br>(SEQ ID NO. 40) | 40 |
| Viral/bacterial components | Anthrax spores<br>Rous sarcoma virus | Sequences are not given<br>AGGACCCUCGAGGGAGGUUGCGCA<br>GGGU<br>(SEQ ID NO. 42) | 41<br>42 |

REFERENCE LISTING FOR TABLE I

1. Ueyama, H., Takagi, M. & Takenaka, S. A novel potassium sensing in aqueous media with a synthetic oligonucleotide derivative, fluorescence resonance energy transfer associated with guanine quartet-potassium ion complex formation. J. Am. Chem. Soc. 124, 14286-14287 (2002).
2. Ciesiolka, J. & Yarus, M. Small RNA-divalent domains. RNA 2, 785-793 (1996)
3. Hofmann, H. P., Limmer, S., Hornung, V. & Sprinzl, M. Ni2+-binding RNA motifs with an asymmetric purine-rich internal loop and a G-A base pair. RNA 3, 1289-300. (1997).
4. Ellington, A. D. & Szostak, J. W. In vitro selection of RNA molecules that bind specific ligands. Nature (London) 346, 818-22 (1990).
5. Grate, D. & Wilson, C. Laser-mediated, site-specific inactivation of RNA transcripts. Proc. Natl. Acad. Sci. U.S.A. 96, 6131-6136 (1999).
6. Wilson, C. & Szostak, J. W. Isolation of a fluorophore-specific DNA aptamer with weak redox activity. Chemistry & Biology 5, 609-617 (1998).
7. Wilson, C., Nix, J. & Szostak, J. Functional Requirements for Specific Ligand Recognition by a Biotin-Binding RNA Pseudoknot. Biochemistry 37, 14410-14419 (1998).

-continued

8. Zimmermann, G. R., Wick, C. L., Shields, T. P., Jenison, R. D. & Pardi, A. Molecular interactions and metal binding in the theophylline-binding core of an RNA aptamer. Rna 6, 659-667 (2000).
9. Meli, M., Vergne, J., Decout, J.-L. & Maurel, M.-C. Adenine-aptamer complexes. A bipartite RNA site that binds the adenine nucleic base. J. Biol. Chem. 277, 2104-2111 (2002).
10. Stojanovic, M. N.; Landry, D. W., Aptamer-Based Colorimetric Probe for Cocaine; J. Am. Chem. Soc.; 124(33); 9678-9679 (2002).
11. Mannironi, C., Di Nardo, A., Fruscoloni, P. & Tocchini-Valentini, G. P. In vitro selection of dopamine RNA ligands. Biochemistry 36, 9726-9734 (1997).
12. Connell, G. J., Illangesekare, M. & Yarus, M. Three small ribooligonucleotides with specific arginine sites. Biochemistry 32, 5497-502 (1993).
13. Famulok, M. Molecular Recognition of Amino Acids by RNA-Aptamers: An L-Citrulline Binding RNA Motif and Its Evolution into an L-Arginine Binder. J. Am. Chem. Soc. 116, 1698-706 (1994).
14. Sassanfar, M. & Szostak, J. W. An RNA motif that binds ATP. Nature (London) 364, 550-3 (1993).
15. Koizumi, M. & Breaker, R. R. Molecular Recognition of cAMP by an RNA Aptamer. Biochemistry 39, 8983-8992 (2000).
16. Davis, J. H. & Szostak, J. W. Isolation of high-affinity GTP aptamers from partially structured RNA libraries. Proc. Natl. Acad. Sci. U.S.A. 99, 11616-11621 (2002).
17. Connell, G. J. & Yarus, M. RNAs with dual specificity and dual RNAs with similar specificity. Science (Washington, D. C.) 264, 1137-41 (1994).
18. Huizenga D. E. and Szostak J. W., A DNA aptamer that binds adenosine and ATP. Biochemistry, 34, 656-65 (1995).
19. Boiziau, C., Dausse, E., Yurchenko, L. & Toulme, J.-J. DNA aptamers selected against the HIV-1 trans-activation-responsive RNA element form RNA-DNA kissing complexes. J. Biol. Chem. 274, 12730-12737 (1999).
20. Burke, D. & Hoffman, D. A Novel Acidophilic RNA Motif That Recognizes Coenzyme A. Biochemistry 37, 4653-4663 (1998).
21. Lauhon, C. T. & Szostak, J. W. RNA aptamers that bind flavin and nicotinamide redox cofactors. J. Am. Chem. Soc. 117, 1246-57 (1995).
22. Roychowdhury-Saha, M., Lato, S. M., Shank, E. D. & Burke, D. H. Flavin Recognition by an RNA Aptamer Targeted toward FAD. Biochemistry 41, 2492-2499 (2002).
23. Chinnapen, D. J. F. & Sen, D. Hemin-Stimulated Docking of Cytochrome c to a Hemin-DNA Aptamer Complex. Biochemistry 41, 5202-5212 (2002).
24. Lorsch, J. R. & Szostak, J. W. In vitro selection of RNA aptamers specific for cyanocobalamin. Biochemistry 33, 973-82 (1994).
25. Wang, Y., Killian, J., Hamasaki, K. & Rando, R. R. RNA Molecules That Specifically and Stoichiometrically Bind Aminoglycoside Antibiotics with High Affinities. Biochemistry 35, 12338-12346 (1996).
26. Yang, Q., Goldstein, I. J., Mei, H.-Y. & Engelke, D. R. DNA ligands that bind tightly and selectively to cellobiose. Proc. Natl. Acad. Sci. U.S.A. 95, 5462-5467 (1998).
27. Srisawat, C., Goldstein, I. J. & Engelke, D. R. Sephadex-binding RNA ligands: rapid affinity purification of RNA from complex RNA mixtures. Nucleic Acids Res. 29, E4/1-E4/5 (2001).
28. Wallis, M. G. et al. In vitro selection of a viomycin-binding RNA pseudoknot. Chem. Biol. 4, 357-366 (1997).
29. Wallace, S. T. & Schroeder, R. In vitro selection and characterization of streptomycin-binding RNAs: recognition discrimination between antibiotics. Rna 4, 112-123 (1998).
30. Berens, C., Thain, A. & Schroeder, R. A tetracycline-binding RNA aptamer. Bioorganic & Medicinal Chemistry 9, 2549-2556 (2001).
31. Williams, K. P. et al. Bioactive and nuclease-resistant L-DNA ligand of vasopressin. Proc. Natl. Acad. Sci. U.S.A. 94, 11285-11290 (1997).
32. Nieuwlandt, D., Wecker, M. & Gold, L. In Vitro Selection of RNA Ligands to Substance P. Biochemistry 34, 5651-9 (1995).
33. Tuerk, C., MacDougal, S. & Gold, L. RNA pseudoknots that inhibit human immunodeficiency virus type 1 reverse transcriptase. Proc. Natl. Acad. Sci. U.S.A. 89, 6988-92 (1992).
34. Bock, L. C., Griffin, L. C., Latham, J. A., Vermaas, E. H. & Toole, J. J. Selection of single-stranded DNA molecules that bind and inhibit human thrombin. Nature (London) 355, 564-6 (1992).
35. Ruckman, J. et al. 2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain. J. Biol. Chem. 273, 20556-20567 (1998).
36. Lebruska, L. L. & Maher, L. J., III. Selection and Characterization of an RNA Decoy for Transcription Factor NF-kB. Biochemistry 38, 3168-3174 (1999).
37. Wiegand, T. W. et al. High-affinity oligonucleotide ligands to human IgE inhibit binding to Fc epsilon receptor I. J. Immunol. 157, 221-30 (1996).
38. Nazarenko, I. A. & Uhlenbeck, O. C. Defining a Smaller RNA Substrate for Elongation Factor Tu. Biochemistry 34, 2545-52 (1995).
39. Davis, K. A., Lin, Y., Abrams, B. & Jayasena, S. D. Staining of cell surface human CD4 with 2'-F-pyrimidine-containing RNA aptamers for flow cytometry. Nucleic Acids Res. 26, 3915-3924 (1998).

| | -continued |
|---|---|
| 40 | Blank, M., Weinschenk, T., Priemer, M. & Schluesener, H. Systematic evolution of a DNA aptamer binding to rat brain tumor microvessels. Selective targeting of endothelial regulatory protein pigpen. J. Biol. Chem. 276, 16464-16468 (2001). |
| 41 | Bruno, J. G. & Kiel, J. L. In vitro selection of DNA aptamers to anthrax spores with electrochemiluminescence detection. Biosensors & Bioelectronics 14, 457-464 (1999). |
| 42 | Pan, W. et al. Isolation of virus-neutralizing RNAs from a large pool of random sequences. Proc. Natl. Acad. Sci. U.S.A. 92, 11509-13 (1995). |

Another example of analysis chemistry is described in U.S. patent application Ser. No. 10/980,856 entitled "Nucleic Acid Enzyme Light-Up Sensor Utilizing Invasive DNA" to Yi Lu et al., filed 3 Nov. 2004, describes a colorimetric sensor system which uses a nucleic acid substrate to form an aggregate, by hybridization of the substrate with nucleic acid attached to a nanoparticle. This system also produces a visualization species containing a nucleic acid attached to a nanoparticle. The analysis chemistry reagents comprise a nucleic acid enzyme, which in the presence of the analyte (for example, a metal ion) will cleave the substrate, releasing the visualization species from the aggregate. Again, nucleic acid enzymes which will cleave the same substrate, but in the presence of different analytes, may be prepared. Similarly to the system described above, all parts of the analytical test may be the same for different analytes, as long as the analysis chemistry reagents contain a nucleic acid enzyme which will cleave the substrate in the presence of the analyte of interest.

In a variation of this system, the substrate may be attached to the base in the reaction area at one end, and the other end attached to a label, such as a fluorescent compound or a particle; when the analyte of interest is present, the nucleic acid enzyme will cleave the substrate, releasing the visualization species which contains the label and a portion of the substrate. The attachment may be covalent, for example through an amine, thio or carboxyl group, or may be through physical adsorption. For a more detailed treatment of how to prepare oligonucleotide functionalized particles, See U.S. Pat. No. 6,361,944; Mirkin, et al., *Nature* (London) 1996, 382, 607-609; Storhoff, et al., *J. Am. Chem. Soc.* 1998, 20, 1959-1064; and Storhoff, et al., *Chem. Rev.* (Washington, D.C.) 1999, 99, 1849-1862. In another variation of this system, the nucleic acid enzyme, which is mostly sensitive to the presence of metal ions, can be replaced with an allosteric nucleic acid enzyme (aptazyme). In this system, nucleic acid complementary to the portion of the substrate that is present in the visualization species may be used.

Other systems are possible. For example, an analytic test for protease could use a protein which is cleaved by the protease. One end of the protein is attached to the base in the reaction area, and the other end of the protein attached to a label. In the presence of the protease, the protein would be cleaved, and a portion of the protein attached to the label would be released, as the visualization species. A capture species, such as an antibody specific for the portion of the protein, may be used.

As another example, an analytic test for an esterase may be made. Here, biotin attached to the base with an ester linkage, and having a label attached to the biotin, would be present in the reaction area. If an esterase were present in the sample, then the ester linkage would be broken, releasing the labeled biotin as the visualization species. A capture species, such as streptavidin, may be used.

The label of the visualization species and verification species allows for detection. Examples of labels include nanocrystals and quantum dots such as semiconductor nanocrystals and quantum dots, dyes, fluorophores, raman dyes, radioactive isotopes, magnetic particles and colored particles. Detection may be by any means or system which can detect the visualization and/or verifications species, including by the human eye and instrumentation such as a spectrophotometer.

The particles, which may be used as labels, include metals such as gold, silver, copper, and platinum; semiconductors, such as CdSe, CdS, and CdS or CdSe coated with ZnS; and magnetic colloidal materials, such as those described in Josephson, Lee, et al., Angewandte Chemie, International Edition (2001), 40(17), 3204-3206. Specific useful particles may include ZnS, ZnO, TiO$_2$, AgI, AgBr, HgI$_2$, PbS, PbSe, ZnTe, CdTe, In$_2$S$_3$, In$_2$Se$_3$, Cd$_3$P$_2$, Cd$_3$AS$_2$, InAs, and GaAs. A specific example is gold (Au) nanoparticles that have an average diameter of 5 to 70 nanometers (nm) or 10 to 50 nm.

Figure 5:
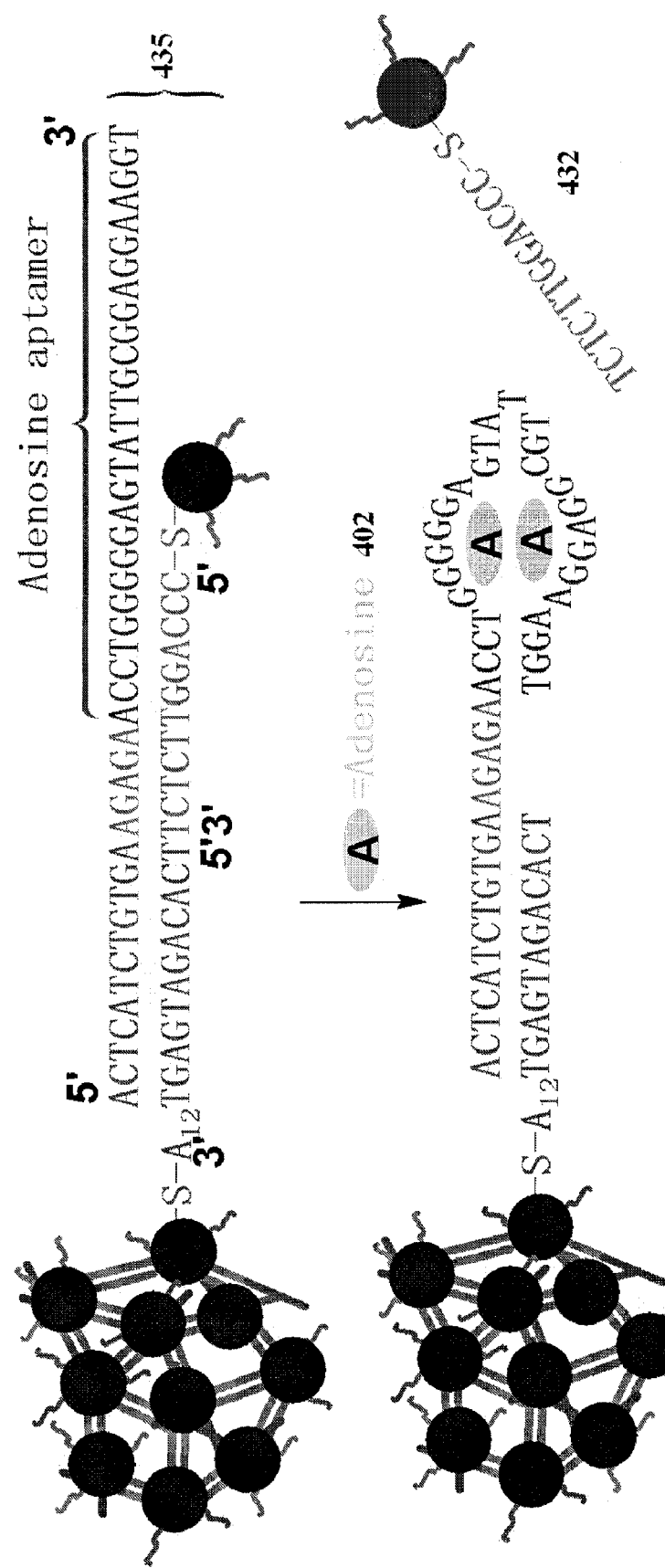
FIG. 5 depicts a lateral flow device adapted for use with aggregate analysis chemistry. Figure discloses SEQ ID NOS 47-51, respectively, in order of appearance.

FIG. 5 depicts aggregate analysis chemistry for use with the lateral flow device 100 (FIGS. 1A-1B) where an aggregate composed of analysis chemistry reagents 435 disaggregates in the presence of the analyte 402. In this manner, the disaggregated fragments of the aggregate serve as the visualization species 432 and travel from the reaction area 120 to the visualization area 130 (FIG. 1A). Due to the physical size of the aggregates, the aggregates do not substantially travel away from the conjugate pad 170 (FIG. 1B) until disaggregation.

Figure 4:
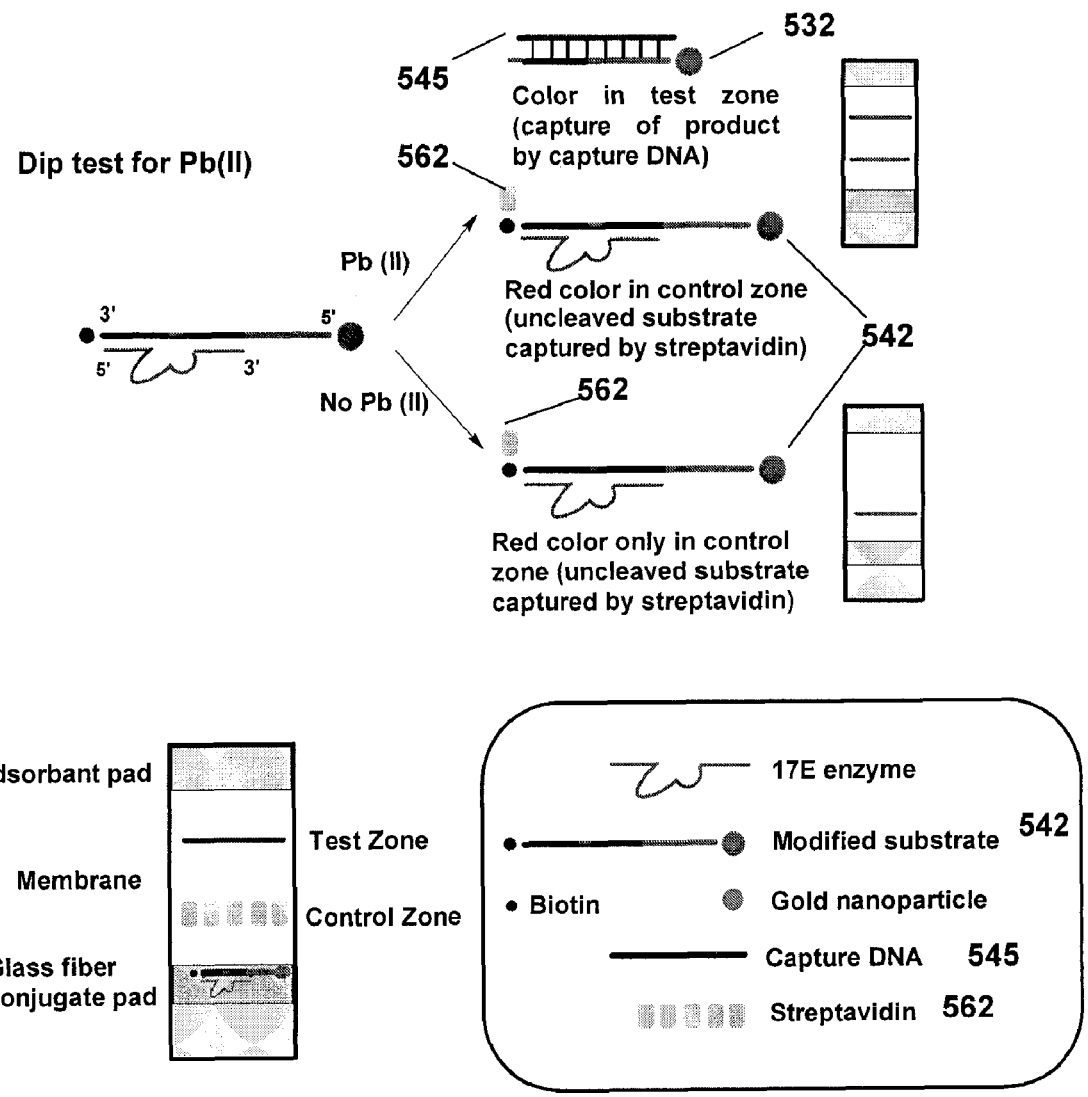
FIG. 4 depicts a lateral flow device adapted for use with cleavage analysis chemistry.

FIG. 4 depicts analysis chemistry reagents 535 for use with the lateral flow device 100 (FIGS. 1A-1B) where a nucleic acid substrate having a gold nanoparticle attached at the 5' end and a biotin moiety attached at the 3' end, is cleaved by a NAE that relies on the analyte as a co-factor. The substrate and the NAE, which together form the analysis chemistry reagents 535, is on the conjugate pad 170 (for example, a glass fiber conjugate pad) (FIG. 1B) of the device 100; this forms the reaction area 120. When cleaved by the NAE, the portion of the substrate functionalized to the nanoparticle becomes the visualization species 532 and travels from the reaction area 120 to the visualization area 130 (FIG. 1A). In this example, the first visualization zone 140 contains the trapping species (streptavidin) 562, and the second visualization zone 150 contains the capture species (DNA complementary to the portion of the substrate present in the visualization species) 545. In this example, all species containing biotin are stopped at the first visualization zone. Therefore, if the analyte is not present, then the substrate is not cleaved and the verification species 542 is trapped at the first visualization zone and no visualization species 532 is produced. If the analyte is present, the at least some of the substrate is cleaved producing visualization species 532 which passes through the first visualization zone (since it does not contain biotin) and is captured by capture species 545 in the second visualization zone, and verification species 542 (present because an excess of the analysis chemistry reagents 535 is present) is trapped by the trapping species. Additional visualization zones containing the trapping species, streptavidin, may be included to reduce leakage of uncleaved substrate to reduce false positive results. Furthermore, the particles may be functionalized with a mixture of substrate and non-substrate nucleic acid, to reduce the density of the substrate with biotin moiety.

Figure 8:
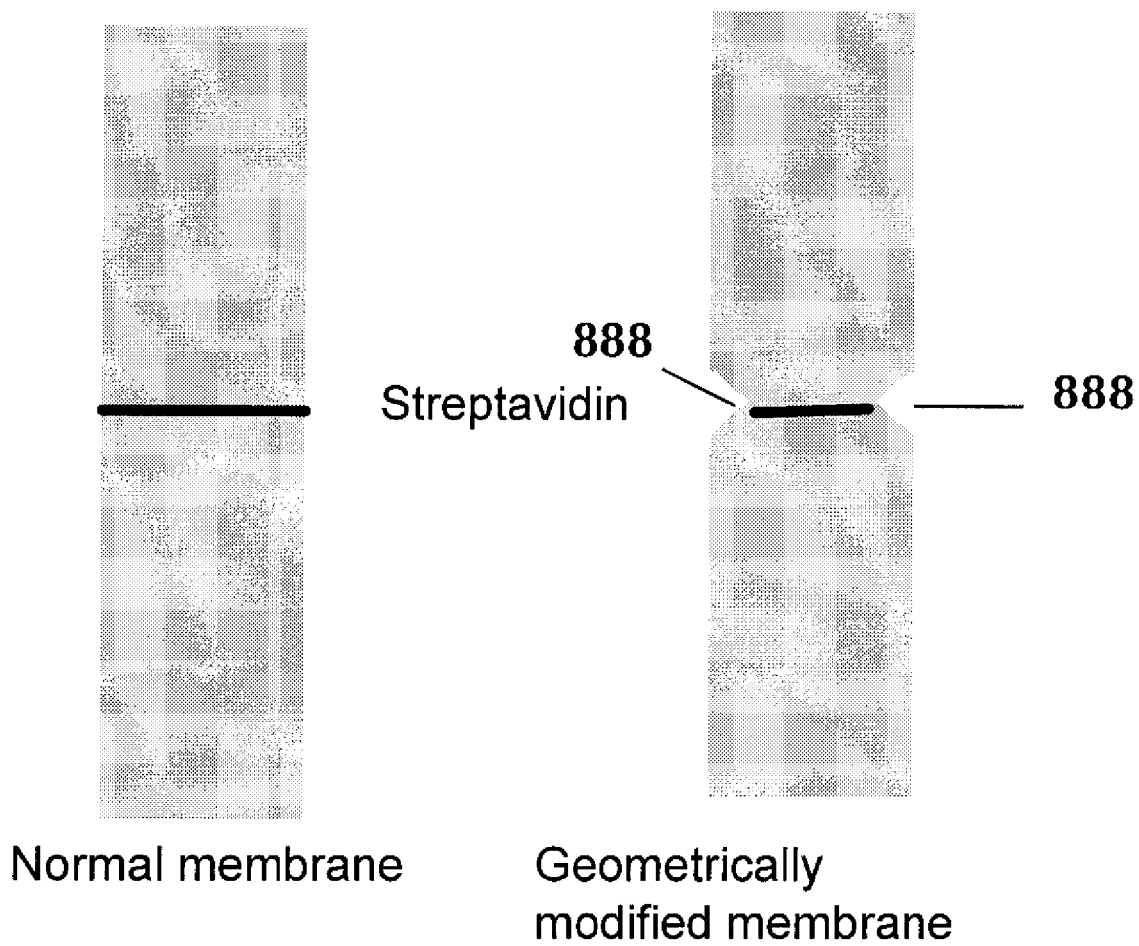
FIG. 8 is a geometrically confined membrane; streptavidin is denoted as a black line.

Different shapes of the membrane, other than a rectangle, may be used to guide the flow so that the capture can be concentrated, or other beneficial effects can be generated. Shown in FIG. 8 are a normal rectangular membrane and a geometrically modified membrane. By cutting the membrane, the capture nanoparticles will be concentrated with a shorter width. The modification cuts 888 are illustrated in the figure.

The following examples are provided to illustrate one or more preferred embodiments of the invention. Numerous variations can be made to the following examples that lie within the scope of the invention.

EXAMPLES

All DNA samples were purchased from Integrated DNA Technology Inc., Coralville, Iowa. The aptamer linkers, substrates, and enzyme portions of the DNAzyme were purified by HPLC prior to use. Gold nanoparticles having an average diameter of 13 nm were prepared and functionalized with 12-mer thiol-modified DNA following literature procedures, such as those disclosed in Storhoff, J., et al., "One-pot calorimetric differentiation of polynucleotides with single base imperfections using gold particle probes," *JACS* 120: 1959-1964 (1998), for example. The average diameter of the functionalized gold nanoparticles was verified by transmission electronic microscope (JEOL 2010).

Example 1

Preparation of A Lateral Flow Device

A Millipore "Assembly Kit" (Cat#HF090AK020, Millipore, Billerica, Mass.) was used to assemble a lateral flow device. The kit contains a membrane on plastic backing (Hi-Flow Plus Cellulose Ester Membrane with capillary flow time of 90 sec/4 cm and a nominal thickness of 135 microns, HF 090 Type 60 mm×300 mm, directly cast onto a 2 mil polyester backing). The absorption pad (Sample pads (AP22) 20 mm×300 mm), conjugate pad (glass fiber conjugate pads 10 mm×300 mm), and wicking pad (adsorption pad) were assembled as shown in FIG. 1A. The membrane was placed at the center of a plastic adhesive backing. The glass fiber conjugate pad was placed on one side of the membrane with part of the conjugate pad overlapping the membrane. Adsorbent pads were placed on each end of the adhesive strip. The 35 cm wide backing including the assembled components was then cut into 1 cm wide lateral flow devices for use. In this manner, the adsorbent pads were on each longitudinal end of the lateral flow devices.

Example 2

Preparation of Lateral Flow Device for Aggregate Based Analysis Chemistry

Ten μL of a prepared aggregate was dropped on the conjugate pad (10 mm width) of the lateral flow device of Example 1 and was allowed to dry. Four μL of 200 μM capture DNA having the sequence 3'-AGAGAAC-CTGGGTTTTTTTTTTTT-5' (SEQ ID NO: 43) was applied on the membrane portion of the device to form a capture zone. The capture DNA was complementary to the 5'-thiol-modified DNA functionalized nanoparticle described below with regard to Example 3. The device was allowed to dry at room temperature.

Example 3

Preparation of Aggregate Based Analysis Chemistry

Figure 6:
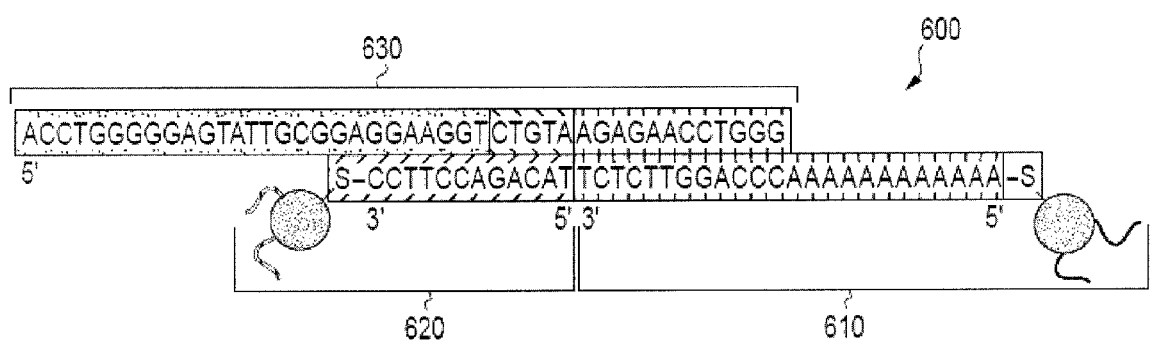
FIG. 6 represents aggregate units that aggregate to form analysis chemistry. Figure discloses SEQ ID NOS 52-53, respectively, in order of appearance.

Aggregate based analysis chemistry for application to a lateral flow device, such as the device of Example 2, was prepared by forming gold nanoparticle aggregates. FIG. 6 represents aggregate units 600 that aggregate to form the analysis chemistry. The units 600 were prepared by combining 6 nM of DNA functionalized nanoparticles 610 and 6 nM of DNA functionalized nanoparticles 620 with linker 630. The linker 630 included an aptamer portion that folds in response to adenosine, the analyte. The functionalized nanoparticles 610, 620 and the linker 630 were combined in an aqueous solution including 300 mM NaCl and 25 mM Tris acetate buffer, pH 8.2. The total volume of the sample was 500 μL. After combination, the mixture was stored at 4° C. for 1.5 hours as aggregates having a deep purple color formed. The mixture was centrifuged and the supernatant removed. The remaining aggregates were re-dispersed in 100 μL of an aqueous buffer solution containing 100% sucrose, 150 mM NaCl, and 25 mM Tris acetate, pH 8.2.

Example 4

Analysis and Detection of an Adenosine Analyte

A lateral flow device was prepared as described in Example 2 and equipped with the analysis chemistry from Example 3 to detect adenosine as an analyte in a sample. For detection, the device was dropped into a water solution containing either 5 mM adenosine or 5 mM uridine with various NaCl concentrations. For the samples containing adenosine, a red color was observed in the absorption pad of each device. However, no red color was observed for samples dipped in uridine. When the sample lacked NaCl, functionalized nanoparticle capture was substantially reduced. Capture was observed when either 100 or 200 mM of NaCl was added to the sample. Because capture was based on DNA hybridization, increasing the NaCl concentration increased capture. The experiment demonstrated that the lateral flow device can be used for the calorimetric detection of an analyte, such as adenosine.

Example 5

Preparation of Lateral Flow Device for Cleavage Based Analysis Chemistry

The lateral flow device was assembled as described in Example 1. Four μL of 10 mg/mL streptavidin (Promega Corp.) was applied on the membrane close to the conjugate pad of a lateral flow device. Further away from the conjugate pad, 4 μL of 1 mM capture DNA (capture-SH-mem-biotin-2) was applied on the membrane. The device was allowed to dry overnight.

FIG. 4 shows the scheme for a dip test for Pb(II). The substrate modified with gold nanoparticles is pre-hybridized with the DNA enzyme and then dried onto the conjugate pad. There are two capture areas on the membrane, called the control zone (with streptavidin) and the test zone (with DNA complementary to the 5' cleavage product, called capture DNA). When the test strip is dipped in a flow buffer the DNAzyme-gold nanoparticles are rehydrated. Any uncleaved substrate will be captured by streptavidin in the control zone, producing a red colored line. If the flow buffer contains Pb(II), cleavage reaction can occur and the 5' product of the substrate (containing the gold nanoparticles) can move further on the membrane and be captured by a complementary DNA strand in the test zone. Thus two red bands on the membrane indicates the presence of Pb(II).

Example 6

Preparation of Cleavage Based Analysis Chemistry

Gold nanoparticles with an average diameter of 13 nm were functionalized with the chimeric substrate SH-mem-biotin-2 which has a thiol group on the 5' end and a biotin moiety on the 3' end. DNA was activated by adding tris-carboxy ethyl phosphine (TCEP) in the ratio of 1:2 (DNA: TCEP) and incubating at room temperature for 2 hours. The gold nanoparticles were functionalized by adding the activated DNA to the as prepared nanoparticles to a final DNA concentration of 3 µM (Typically 15 µL of 1 mM DNA is added to 5 mL of nanoparticles). After incubation for approximately 24 h, NaCl was added to a final concentration of 100 mM and the solution was incubated for one day.

The functionalized nanoparticles were then centrifuged at 13000 rpm for 20 minutes. The nanoparticles settled to the bottom and the supernatant containing free DNA was removed. The nanoparticles were then re-dispersed in an aqueous solution including 25 mM Tris-HCl, 100 mM NaCl, at a pH of 8.0 and the centrifugation step was repeated 2 more times. The nanoparticles were finally dispersed in a 50 mM Tris-HCl buffer solution (pH 8.0) containing 100% sucrose (weight/weight), 0.25% sodium dodecyl sulfate (weight/weight), and 100 mM NaCl to a nanoparticle concentration of ~30-50 nM (~400-600 µL total volume).

Table 1, below, provides the base sequences for the analysis chemistry reagents and the visualization area of a lateral flow device where Pb(II) (analyte), serves as the co-factor for the NAE.

| Moiety | SEQ ID NO | Sequence 5'→3' |
|---|---|---|
| SH-mem-biotin-2 | 44 | SSH-C6-AAGAAGAAGAAGAAGAAG CACTA T rAGGAAGAGATGTC-C6-Biotin |
| 17E + 2-3 | 45 | GACATCTCTTCTCCGAGCCGGTCGAAATAG TG |
| Capture-SH-mem-biotin-2 | 46 | ATAGTGCTTCTTCTTCTTCTTCTT |

Example 7

Figure 7:
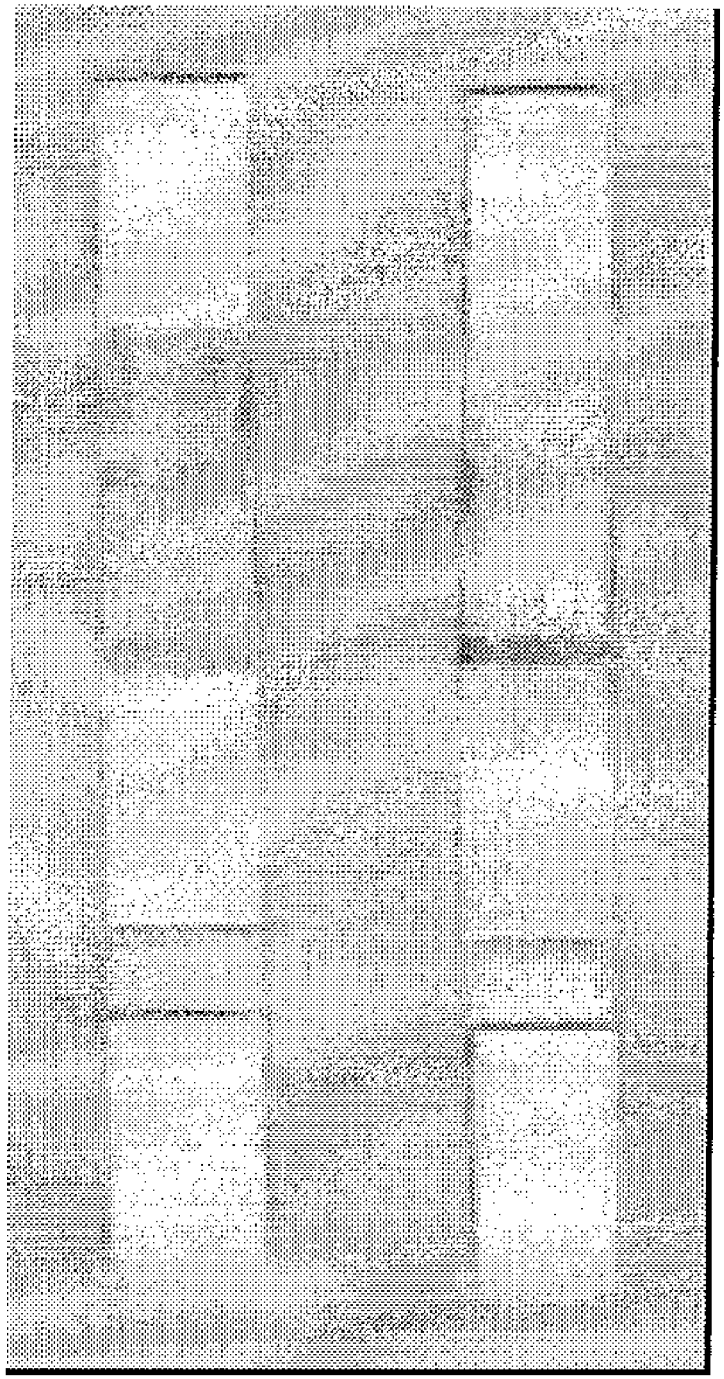
FIG. 7 is a photograph of lateral flow devices.

Analysis and Detection of a Lead Analyte: Synthesizing the Reaction Chemistry on the Device A lateral flow device was prepared as described in Example 5 and equipped with the analysis chemistry from Example 6 to detect lead as an analyte in a sample. Eight µL of substrate functionalized gold nanoparticles and 1 µL of 1 mM enzyme 17E+2-3 in 25 mM Tris-HCl buffer, pH 8.0 was hybridized and applied on the conjugate pad. This was allowed to dry for at least 3 h. Ten µL of 4 mM Pb(II), was added on the adsorbent pad (reaction area) next to the conjugate pad. The control (no Pb(II)) was prepared by substituting the Pb(II) with water. The pad was dipped in a liquid flow buffer including 25 mM Tris-HCl (pH 8.0), 100 mM NaCl, 4% glycerol, and 0.1% SDS. After a few minutes, when the buffer had migrated completely to the top of the membrane, the pad was laid horizontally on a flat surface. Analyses were performed for multiple enzyme and lead concentrations. FIG. 7 is a photograph of the lateral flow devices tested in the presence and absence of the analyte, Pb(II).

Example 8

Figure 9:
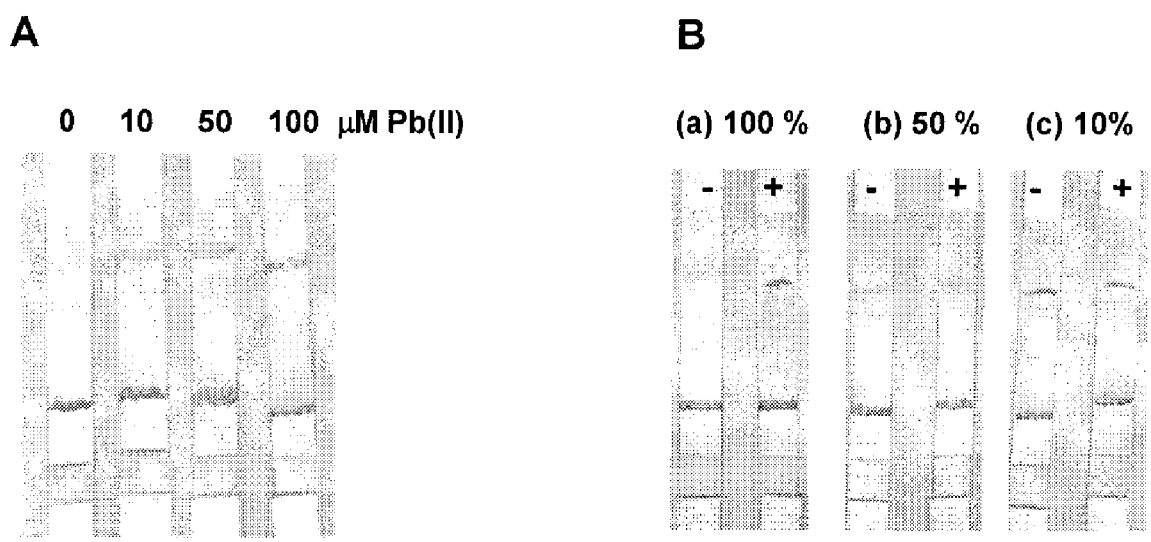
FIG. 9 is a scanned images of lateral flow test for Pb(II), devices: (A) Tests done with different concentration of Pb(II); (B) Effect of varying the percentage of biotinylated substrate on the performance of the test.

Analysis and Detection of a Lead Analyte: Synthesizing the Reaction Chemistry off the Device FIG. 9a shows the result from an experiment carried out with different concentrations of Pb(II) in the flow buffer. In the absence of Pb(II), there is only one red line at the control zone. As the Pb(II) concentration is increased a red line of increasing intensity appears at the test zone. This test can be semi-quantitative as the ratio of intensity of color at the test zone versus intensity of color at the control zone will increase with increasing concentration of Pb(II).

The effect of using varying fractions of the biotinylated substrate to modify the gold nanoparticles was also investigated (FIG. 9b). Unlike in the case of the aptamer based lateral flow device, it is best to use 100% biotinylated substrate to modify the gold nanoparticles. Using a mixture of biotinylated substrate and non-biotinylated DNA leads to inefficient capture of uncleaved substrate at the streptavidin zone. Thus, as the fraction of biotinylated DNA is decreased, no difference can be seen between the Pb and no Pb case because the gold nanoparticles with uncleaved substrate can escape capture at the control zone and are non-specifically captured by DNA at the test zone.

Example 9

Analysis and Detection of a Lead Analyte: Synthesizing the Reaction Chemistry off the Device Eight µL of substrate functionalized gold nanoparticles, 1 µL of 1 mM enzyme, and 1 µL of 500 µM Pb(II) (water used for the no Pb(II) control) was incubated in a tube at 37° C. for 10 minutes. The mixture was then applied to the conjugate pad and allowed to dry. The pad was then dipped in the flow liquid allowing the cleaved visualization species to migrate toward the visualization area of the device. In this example, the lateral flow device is simply being used to observe the reaction result, whereas the Pb(II) catalyzed cleavage reaction is performed off the device.

Example 10

Adenosine-Responsive Nanoparticle Aggregates Containing Two Kinds of DNA-Functionalized Gold Nanoparticles and an Aptamer DNA a. Lateral Flow Device Approximately 50% of the nanoparticles were functionalized with biotinylated thiol-modified DNA and the other 50% with thiol-modified DNA lacking the biotin group. The biotin group is denoted as a black star in FIG. 14A. The biotin modification allows the nanoparticle to be captured by streptavidin. We chose to use 50% biotinylated DNA because 100% biotinylated DNA led to low nanoparticle aggregate yield (<20%), while 100% biotinylated DNA led to inadequate streptavidin capture (data not shown).

Figure 10:
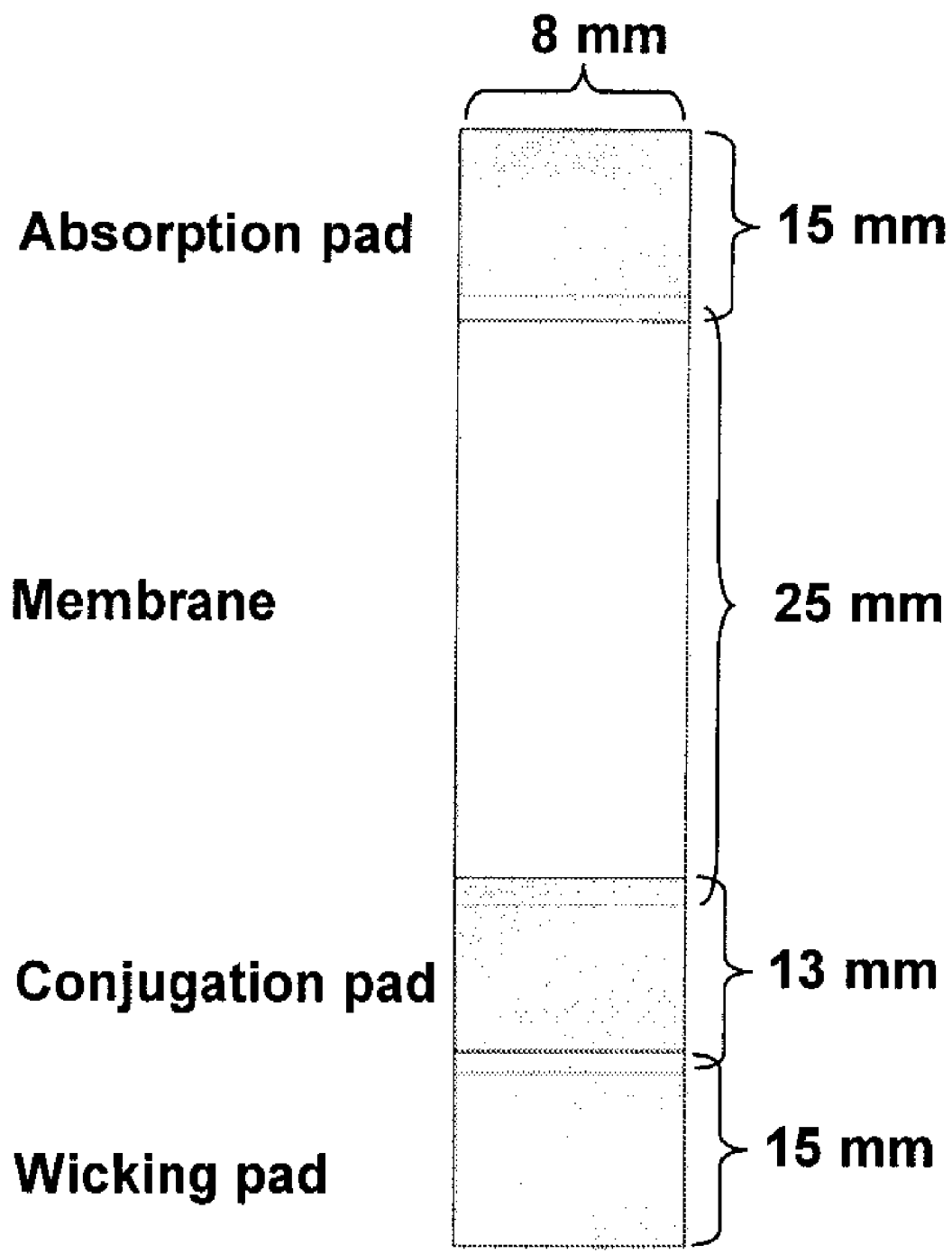
FIG. 10 is a lateral flow device.

The Millipore Hi-Flow™ Plus Assembly Kit (Millipore Corporation, Bedford, Mass.) was used. The kit contains a Hi-Flow Plus Cellulose Ester Membrane with a nominal capillary flow time of 90 seconds/4 cm and a nominal membrane thickness of 135 μm directly cast onto 2 mil polyester backing and placed on an adhesive card. The length of the membrane along the flow direction is 2.5 cm on the backing. The absorption pad and wicking pad were cut from Millipore cellulose fiber sample pads, and the conjugation pad was cut from the Millipore glass fiber conjugate pad. The absorption pad, wicking pad, and conjugation pad were attached to the adhesive card of the membrane in a way as shown in FIG. 10. The overlap for each pad was ~2 mm, and the width was ~8 mm cut by a paper cutter.

Figure 14:
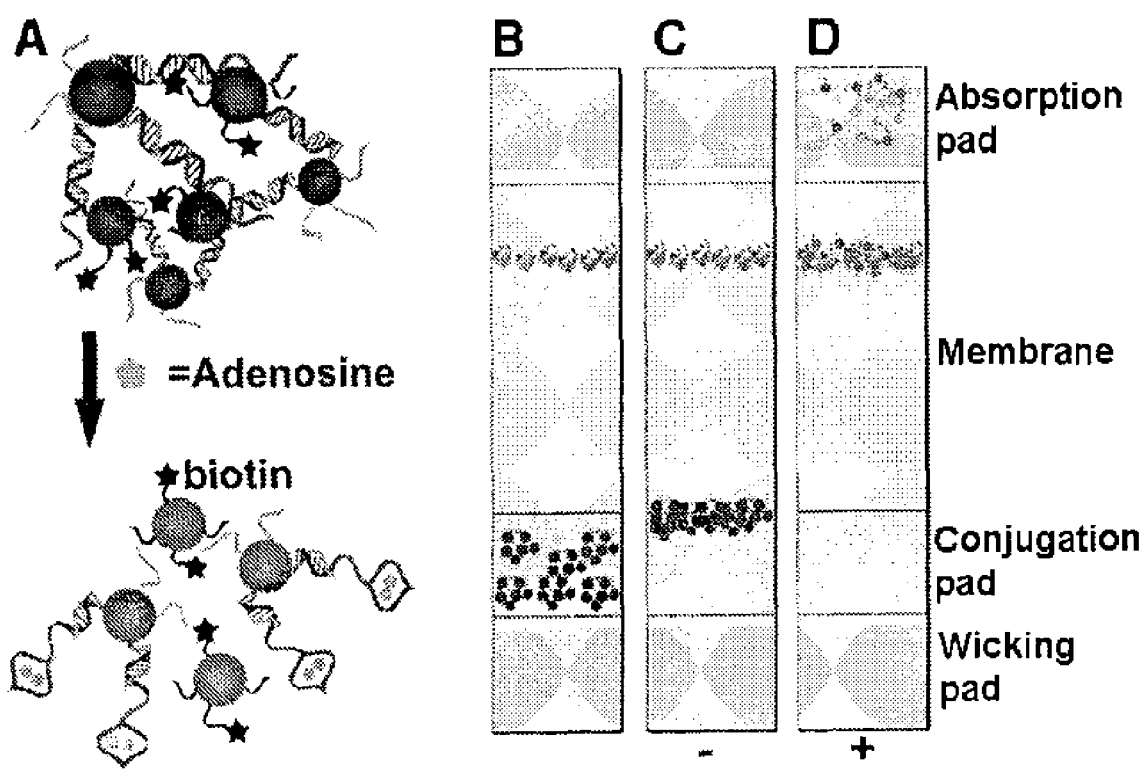
FIG. 14 illustrates an aptamer/nanoparticle-based lateral flow device: (A) Adenosine induced disassembly of nanoparticles into red-colored dispersed nanoparticles—biotin is denoted as a black star; lateral flow devices loaded with the aggregates (on the conjugation pad) and streptavidin (on the membrane) before use (B), in a negative (C), or positive (D) test.

The device included four overlapping pads placed on a backing with the overlaps being 2 mm (FIG. 14B). The four pads are (from top to bottom): an absorption pad (15 mm), a membrane (25 mm), a conjugation pad (13 mm), and a wicking pad (15 mm). The nanoparticle aggregates were spotted on the conjugation pad while streptavidin (2 μL of 10 mg/mL) was applied on the membrane (FIG. 14B), after which the whole device was dried overnight at room temperature before use. Nanoparticle aggregates are too large to migrate along the membrane, while dispersed nanoparticles can migrate. If the device is dipped into a solution without adenosine, the aggregates would be re-hydrated and would migrate to the bottom of the membrane where it would stop because of its large micrometer size (FIG. 14C). In the presence of adenosine, the nanoparticles would be disassembled due to binding of adenosine by the aptamer (FIG. 14A). The smaller dispersed nanoparticles can now migrate along the membrane and be captured by streptavidin to form a red line (FIG. 14D).

b. Aptamer-Assembled Nanoparticle Aggregates

Figure 11:
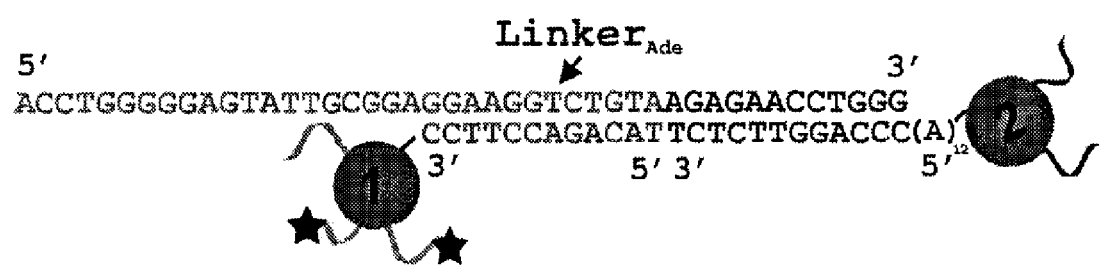
FIG. 11 shows DNA linkages in aptamer-assembled gold nanoparticle aggregates. Figure discloses SEQ ID NOS 52-53, respectively, in order of appearance.

Gold nanoparticles (13 nm diameter) were synthesized by citrate reduction method following literature procedures. Thiol-modified DNA was activated with two equivalents of Tris(2-carboxyethyl)phosphine hydrochloride (TCEP). After mixing TCEP activated thiol-modified DNA (3 μM) and gold nanoparticles (~8 nM) at room temperature for 16 hours or longer, the solution was brought to 100 mM NaCl and 5 mM Tris acetate, pH 8.2. DNA-functionalized nanoparticles were purified by centrifugation and removal of supernatant before use. It needs to be noted that particle 1 (FIG. 11) was functionalized with 2 kinds of 3'-thiol modified DNA with equal molar ratio. One DNA contained a biotin moiety at the 5'-end, and the other one did not contain a biotin; for functionalization, 1.5 μM of each DNA was added to the nanoparticles. Particle 2 was functionalized with only a 5'-thiol modified DNA. To prepare aggregates, 500 μL of each kind of nanoparticle was centrifuged to replace with a buffer containing 300 mM NaCl, 25 mM Tris acetate, pH 8.2 to a final total volume of 500 μL. One μL of 100 μM of the linking DNA was added and the mixture was placed at 4° C. for 6 hours. Dark purple precipitants were formed at the bottom of the tube. After very brief centrifugation, the supernatant was removed and the nanoparticle aggregates were dispersed in designated buffers (in most experiments: 8% sucrose, 200 mM NaCl, 25 mM Tris acetate, pH 8.2). In the presence of adenosine, the aptamer part (FIG. 11, 5' to arrow) bound to adenosine and releases particle 1. As a result, particle 1 and 2 were separated and the color of the nanoparticles turned red.

c. Apply Reagents to Lateral Flow Devices

Six μL of nanoparticle aggregates were spotted on each conjugation pad, and 2 μL of 10 mg/mL streptavidin was applied on the membrane by a 2 μL pipet to form a line. The loaded devices were stored in a drawer overnight before use.

d. Detection

Various concentrations of nucleosides were dissolved in a buffer containing 100 mM NaCl, 25 mM Tris acetate, pH 8.2. The wicking pad of each device was dipped into the solutions for ~20 seconds when the conjugation pad was fully hydrated and the liquid started to migrate on the membrane. Then the device was placed flat on a plastic surface for the flow to continue. A digital camera was used to take the pictures of the devices after ~5 minutes.

e. Effect of NaCl Concentration During Drying

Figure 12:
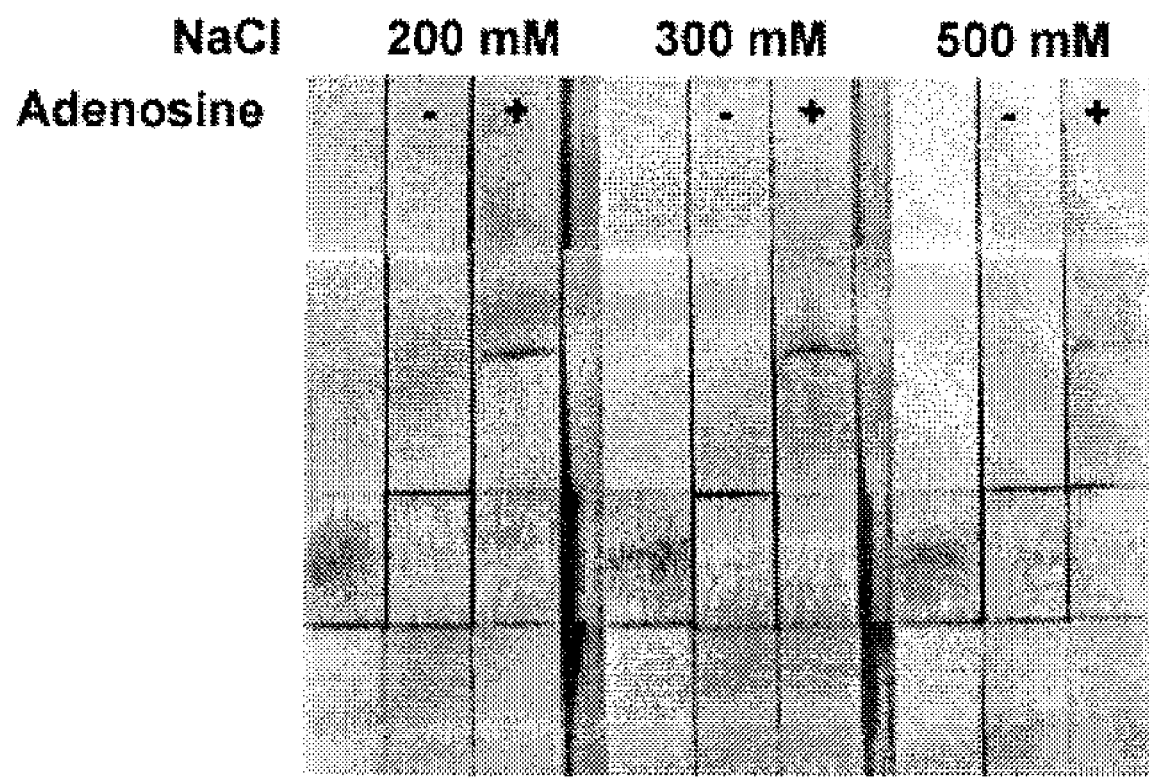
FIG. 12 shows the effect of NaCl concentration during drying of the nanoparticle aggregates on the conjugation pad.

Because the nanoparticle aggregates were stabilized by DNA base pairing interactions, NaCl concentration (ionic strength) played a very important role on the properties of the aggregates. The aggregates were dispersed in various concentration of NaCl: 200, 300, and 500 mM (all with 8% sucrose). The devices were tested with either no adenosine or 500 μM adenosine, and an untested device is also presented in FIG. 12 for comparison. At all the three salt concentrations, adenosine induced a red band; while no band was observed in the absence of adenosine. Five hundred mM NaCl gave the lowest band intensity, and therefore all future experiments used 200 mM NaCl.

f. Stability Studies on the Device

Figure 13:
FIG. 13 shows the effect of NaCl concentration during drying of the nanoparticle aggregates on the conjugation pad.

Preliminary studies on the stability of the devices were tested. After sitting at room temperature and unprotected conditions for a week, the devices were tested with solutions containing 0 or 500 μM adenosine (FIG. 13). The device has retained its function because no red band was observed in the absence of adenosine (left panel, FIG. 13), and a clear red band was observed in the presence of adenosine (right panel, FIG. 13).

Figure 15:
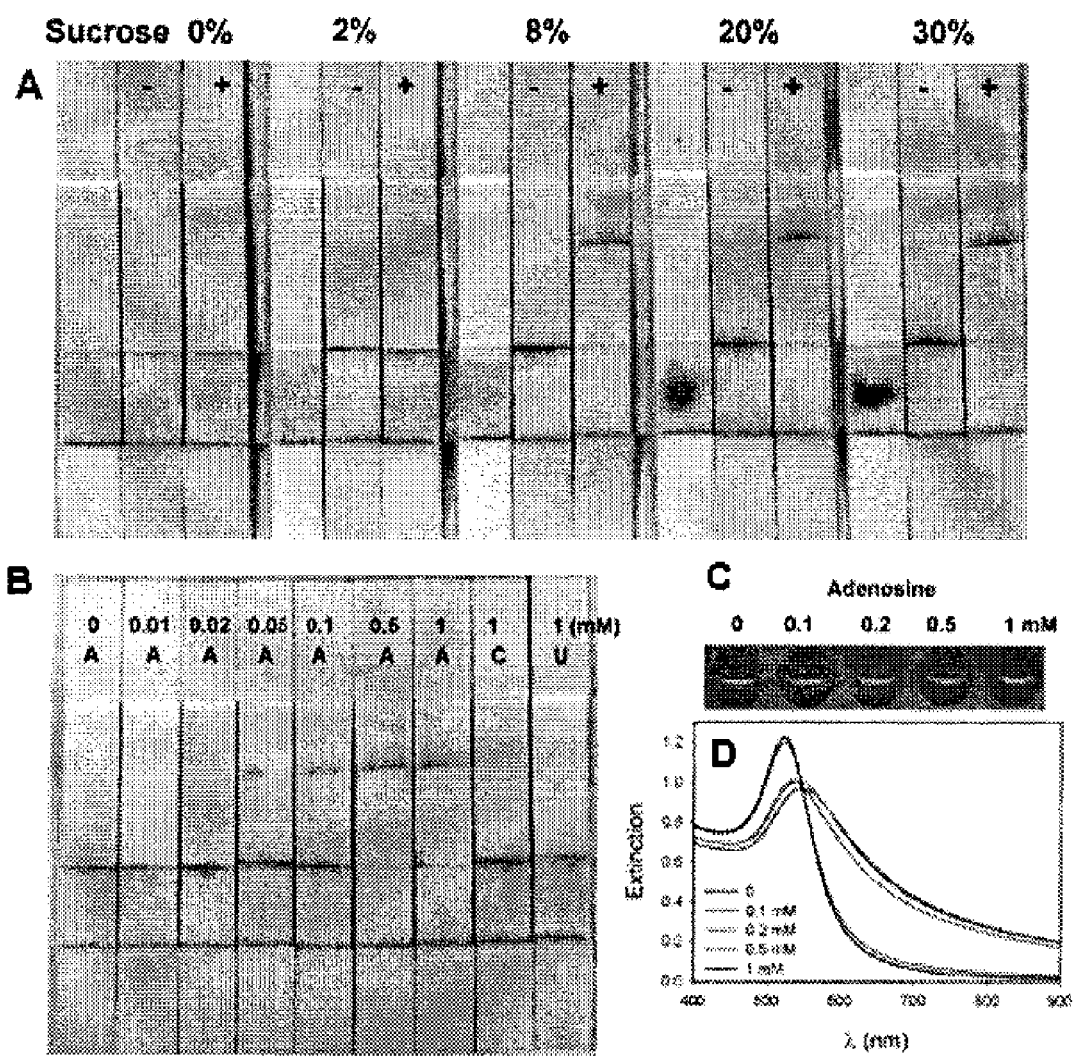
FIG. 15 shows a test for adenosine: (A) Performance of the test after drying with different sucrose concentrations; (B) Test of the lateral flow device with varying concentrations of nucleosides; (C) Scanned color of adenosine-dependent color change in solution phase; (D) UV-vis spectra of the solution samples in (C).

To successfully carry out the detection, the first challenge is to preserve the aptamer activity and the connections between nanoparticles in the dry state. Each aggregate contained thousands of DNA-linked nanoparticles. Directly drying the aggregates in buffer could lead to the loss of hydrogen bonds in the DNA. Sucrose is a commonly used additive to keep DNA in its native state, and the effect of sucrose on drying was first studied. Five conditions with varying sucrose concentrations were tested (FIG. 15A). At each concentration, three devices were tested, with the first one being an unused device, the second one being a negative test (without adenosine), and the third one being a positive test (with 0.5 mM adenosine). Direct drying of aggregates on the conjugation pads deactivated the aggregates, and no red bands were observed in the presence of adenosine (FIG. 15A, 0% sucrose). Interestingly, inclusion of 2% sucrose helped preserve the aggregates and a slight red band was observed on the membrane. With 8% sucrose, an intense red band was observed in the positive test, while no band was observed in the negative test. Instead, a dark band at the boundary between the conjugation pad and the membrane was observed. This observation supported the hypothesis that the aggregates cannot migrate along the membrane. The presence of unreacted aggregates on the boundary provides a useful control; if no such line is observed for a negative sample, the test is invalid, indicating poor re-hydration or flow of the device. Further increase of sucrose concentration up to 30% also showed intense red bands, but a slight band in the background could also be observed. Therefore, 8% sucrose during drying was chosen for further experiments. If the untested strips are compared (i.e., the first strip in each group), increasing the sucrose concentration led to a more intense color on the conjugation pads, even though the same amount of aggregates were applied to each pad. This result indicated that the nanoparticles were still in their native states; that strong individual and coupled surface plasmons still exist and that the nanoparticles had not collapsed due to drying.

Under the optimized drying conditions, the sensitivity and selectivity of the devices were tested. After drying overnight, the devices were dipped into buffers containing various nucleoside species at different concentrations (FIG. 15B). No red band was observed in the absence of adenosine. With increasing adenosine concentrations, more intense red bands were observed, and the detection limit was estimated to be ~20 µM. No red bands were observed with 1 mM cytidine or uridine, suggesting that the high selectivity of the aptamer had been maintained. For comparison, a solution phase reaction was carried out. Under optimized conditions, 500 µM of adenosine was needed to observe a red color (FIG. 15C). The extinction spectra of the solution phase samples were also recorded on spectrophotometer (FIG. 15D), and a small shift was observable with only 100 µM adenosine. This difference, however, cannot be distinguished by the naked eye. When the test results from solution phase and from lateral flow devices were compared, the flow device had at least 10-fold higher sensitivity if the naked eye was used as a detector.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. An analytical test for an analyte, comprising:
   (a) a base, having a reaction area and a visualization area,
   (b) a capture species, on the base in the visualization area, comprising nucleic acid, and
   (c) analysis chemistry reagents, on the base in the reaction area, comprising
      (i) a substrate comprising nucleic acid and a first label, and
      (ii) a reactor comprising nucleic acid,
   wherein the analysis chemistry reagents can react with a sample comprising the analyte and water, to produce a visualization species comprising nucleic acid and the first label, and
   the capture species can bind the visualization species,
   wherein the reactor comprises a nucleic acid enzyme, and the substrate can be cleaved by the nucleic acid enzyme in the presence of the analyte.

2. An analytical test for an analyte, comprising:
   (a) a base, having a reaction area and a visualization area,
   (b) a capture species, on the base in the visualization area, comprising nucleic acid, and
   (c) analysis chemistry reagents, on the base in the reaction area, comprising
      (i) a substrate comprising nucleic acid and a first label, and
      (ii) a reactor comprising nucleic acid,
   wherein the analysis chemistry reagents can react with a sample comprising the analyte and water, to produce a visualization species comprising nucleic acid and the first label, and
   the capture species can bind the visualization species,
   wherein
      the reactor comprises an aptamer,
      the aptamer can bind the substrate,
      the aptamer can bind the analyte, and
      the aptamer cannot simultaneously bind both the analyte and the substrate.

3. The analytical test of claim 1, wherein the reactor comprises an aptazyme.

4. An analytical test for an analyte, comprising:
   (a) a base, having a reaction area and a visualization area,
   (b) a capture species, on the base in the visualization area, comprising nucleic acid, and
   (c) analysis chemistry reagents, on the base in the reaction area, comprising
      (i) a substrate comprising nucleic acid and a first label, and
      (ii) a reactor comprising nucleic acid,
   wherein the analysis chemistry reagents can react with a sample comprising the analyte and water, to produce a visualization species comprising nucleic acid and the first label, and
   the capture species can bind the visualization species,
   wherein the analyte is a metal ion.

5. An analytical test for an analyte, comprising:
   (a) a base, having a reaction area and a visualization area,
   (b) a capture species, on the base in the visualization area, comprising nucleic acid, and
   (c) analysis chemistry reagents, on the base in the reaction area, comprising
      (i) a substrate comprising nucleic acid and a first label, and
      (ii) a reactor comprising nucleic acid,
   wherein the analysis chemistry reagents can react with a sample comprising the analyte and water, to produce a visualization species comprising nucleic acid and the first label, and
   the capture species can bind the visualization species,
   wherein the analyte is a lead ion.

6. An analytical test for an analyte, comprising:
   (a) a base, having a reaction area and a visualization area,
   (b) a capture species, on the base in the visualization area, comprising nucleic acid, and
   (c) analysis chemistry reagents, on the base in the reaction area, comprising
      (i) a substrate comprising nucleic acid and a first label, and
      (ii) a reactor comprising nucleic acid, wherein the analysis chemistry reagents can react with a sample comprising the analyte and water, to produce a visualization species comprising nucleic acid and the first label, and the capture species can bind the visualization species, (d) a trapping species, on the base in the visualization area, wherein the analysis chemistry reagents can react with a sample comprising water, to produce a verification species comprising a second label, and the trapping species can bind the verification species, wherein the reactor comprises a nucleic acid enzyme, and the substrate can be cleaved by the nucleic acid enzyme in the presence of the analyte the first and second labels comprise colored labels, or the first and second labels comprise fluorescent labels, and the analyte is a metal ion.

7. An analytical test for an analyte, comprising:

(a) a base, having a reaction area and a visualization area, (b) a capture species, on the base in the visualization area, and (c) a trapping species, on the base in the visualization area, and (d) analysis chemistry reagents, on the base in the reaction area, wherein the analysis chemistry reagents can react with a sample comprising the analyte and water, to produce a visualization species comprising a first label, the analysis chemistry reagents can react with a sample comprising water, to produce a verification species comprising a second label, the capture species can bind the visualization species, the trapping species can bind the verification species, and the visualization species does not comprise the analyte.

8. The analytical test of claim 7, wherein the capture species specifically binds the visualization species.

9. The analytical test of claim 7, wherein the first label comprises at least one member selected from the group consisting of a colored label, a fluorescent label, a radioactive label and a magnetic label.

10. The analytical test of claim 7, wherein the capture species specifically binds the visualization species, and the trapping species specifically binds the verification species.

11. The analytical test of claim 7, wherein the first and second labels comprise colored labels, or the first and second labels comprise fluorescent labels.

* * * * *

```
SEQUENCE LISTING

<160> NUMBER OF SEQ ID NOS: 53

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gggttagggt tagggttagg g                                             21

<210> SEQ ID NO 2
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aggcgaggug aaaugagcgg uaauagccu                                     29

<210> SEQ ID NO 3
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gggagaggau acuacacgug auagucaggg aacaugacaa acacagggac uugcgaaaau   60
caguguuuug ccauugcaug uagcagaagc uuccg                              95

<210> SEQ ID NO 4
<211> LENGTH: 132
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gggagaattc ccgcggcaga agcccacctg gctttgaact ctatgttatt gggtggggga   60
aacttaagaa aactaccacc cttcaacatt accgcccttc agcctgccag cgccctgcag  120
cccgggaagc tt                                                      132

<210> SEQ ID NO 5
```

```
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ggaucccgac uggcgagagc cagguaacga auggaucc                                  38

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccggccaagg gtgggaggga gggggccgg                                            29

<210> SEQ ID NO 7
<211> LENGTH: 61
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
auggcaccga ccauaggcuc ggguugccag agguuccaca cuuucaucga aaagccuaug          60
c                                                                          61

<210> SEQ ID NO 8
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ggcgauacca gccgaaaggc ccuuggcagc guc                                       33

<210> SEQ ID NO 9
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gauaggacga uuaucgaaaa ucaccagauu ggacccuggu uaacgaucca uu                  52

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gggagacaag gataaatcct tcaatgaagt gggtcgaca                                 39
```

<210> SEQ ID NO 11
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gggaauuccg cgugugcgcc gcggaagagg gaauauagag gccagcacau agugaggccc     60
uccuccc                                                              67

<210> SEQ ID NO 12
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gggagcucag aauaaacgcu caaggaggac cgugcacucc ucgaacauuu cgagaugaga     60
cacggauccu gc                                                        72

<210> SEQ ID NO 13
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gacgagaagg agugcugguu auacuagcgg uuaggucacu cguc                     44

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
acctggggga gtattgcgga ggaaggt                                        27

<210> SEQ ID NO 15
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ggaagagaug gcgacuaaaa cgacuugucg c                                   31

<210> SEQ ID NO 16
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ucuagcaguu cagguaacca cguaagauac ggucuaga 39

<210> SEQ ID NO 17
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (44)
<223> OTHER INFORMATION: a, c, g, u, unknown or other
<220> FEATURE:
<221> NAME/KEY: modified_base
<222> LOCATION: (56)
<223> OTHER INFORMATION: a, c, g, u, unknown or other

<400> SEQUENCE: 17
gggagcucag aauaaacgcu caacccgaca gaucggcaac gccnuguuuu cgacangaga    60
caccgauccu gcaccaaagc uucc    84

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
acctggggga gtattgcgga ggaaggt    27

<210> SEQ ID NO 19
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcagtctcgt cgacacccag cagcgcatgt aactcccata catgtgtgtg ctggatccga    60
cgcag    65

<210> SEQ ID NO 20
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gggcacgagc gaagggcaua agcugacgaa agucagacaa gacauggugc cc    52

<210> SEQ ID NO 21
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ggaacccaac uaggcguuug aggggauucg gccacgguaa caaccccuc    49

<210> SEQ ID NO 22
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gggcauaagg uauuuaauuc cauacaaguu uacaagaaag augca              45

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
taaactaaat gtggagggtg ggacgggaag aagttta                      37

<210> SEQ ID NO 24
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ccggugcgca uaaccaccuc agugcgagca a                            31

<210> SEQ ID NO 25
<211> LENGTH: 108
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gggagaauuc cgaccagaag cuuggvuugu cuuguacguu cacguuacg auuguguuag     60 guuuaacuac acuuugcaau cgcauaugug cgcuacaug gauccuca                108

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcggggttgg gcgggtgggt tcgctgggca gggggcgagt g                 41

<210> SEQ ID NO 27
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uacagaaugg guugguaggc auaccuaauc gagaaugaua              40

<210> SEQ ID NO 28
<211> LENGTH: 113
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 28

```
ggagcucagc uucacugca augggccgcu agguugaugu gcagugaagu cagcugaggc      60
ccagggcuga aaggaucgcc cuccucgacu cguggcacca ggucggauc cac            113
```

<210> SEQ ID NO 29
<211> LENGTH: 45
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 29

```
ggaucgcauu uggacuucug cccaggggc accacggucg gaucc                      45
```

<210> SEQ ID NO 30
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 30

```
ggccuaaaac auaccagauu ucgaucugga gaggugaaga auucgaccac cuaggccggu      60
```

<210> SEQ ID NO 31
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31

```
acgtgaatga tagacgtatg tcgagttgct gtgtgcggat gaacgt                     46
```

<210> SEQ ID NO 32
<211> LENGTH: 107
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 32

```
gggagcugag aauaaacgcu caagggcaac gcgggcaccc cgacaggugc aaaaacgcac      60
cgacgcccgg ccgaagaagg ggauucgaca ugaggcccgg auccggc                   107
```

<210> SEQ ID NO 33
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

```
<400> SEQUENCE: 33
uccguuuuca gucgggaaaa acug                                          24

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggttggtgtg gttgg                                                    15

<210> SEQ ID NO 35
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
gcgguaggaa gaauuggaag cgc                                           23

<210> SEQ ID NO 36
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
gggauauccu cgagacauaa gaaacaagau agauccugaa acuguuuaa gguuggccga    60 ucuucugcuc gagaaugcau gaagcguucc auauuuuu                           98

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ggggcacgtt tatccgtccc tcctagtggc gtgcccc                            37

<210> SEQ ID NO 38
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ggggcuauug ugacucagcg guucgacccc gcuuagcucc acca                    44

<210> SEQ ID NO 39
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 39
ugacguccuu agaauugcgc auuccucaca caggaucuu                             39

<210> SEQ ID NO 40
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ataccagctt attcaattag gcggtgcatt gtggttggta gtatacatga ggtttggttg      60
agactagtcg caagatatag atagtaagtg caatct                               96

<210> SEQ ID NO 41

<400> SEQUENCE: 41

000

<210> SEQ ID NO 42
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
aggacccucg agggagguug cgcagggu                                         28

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tttttttttt ttgggtccaa gaga                                             24

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aagaagaaga agaagaagca ctatraggaa gagatgtc                              38

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gacatctctt ctccgagccg gtcgaaatag tg                                    32
```

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 46
atagtgcttc ttcttcttct tctt                                          24

<210> SEQ ID NO 47
<211> LENGTH: 44
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 47
actcatctgt gaagagaacc tgggggagta ttgcggagga aggt                    44

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 48
cccaggttct cttcacagat gagtaaaaaa aaaaaa                             36

<210> SEQ ID NO 49
<211> LENGTH: 44
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 49
actcatctgt gaagagaacc tgggggagta ttgcggagga aggt                    44

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 50
tcacagatga gtaaaaaaaa aaaa                                          24

<210> SEQ ID NO 51
<211> LENGTH: 12
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 51
tctcttggac cc                                                       12

```
<210> SEQ ID NO 52
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
acctggggga gtattgcgga ggaaggtctg taagagaacc tggg                    44

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
aaaaaaaaaa aacccaggtt ctcttacaga ccttcc                             36
```